United States Patent [19]

Sharma

[11] Patent Number: 5,891,418
[45] Date of Patent: Apr. 6, 1999

[54] PEPTIDE-METAL ION PHARMACEUTICAL CONSTRUCTS AND APPLICATIONS

[75] Inventor: Shubh D. Sharma, Albuquerque, N. Mex.

[73] Assignee: Rhomed Incorporated, Albuquerque, N. Mex.

[21] Appl. No.: 476,652

[22] Filed: Jun. 7, 1995

[51] Int. Cl.⁶ .......................... A61K 51/08; A61K 38/00; A61B 5/055
[52] U.S. Cl. ........................ 424/1.69; 424/9.34; 530/300; 530/330; 530/334; 530/338; 530/333
[58] Field of Search .................................. 424/1.11, 1.65, 424/1.69, 9.1, 9.34, 9.341; 534/7, 10–16; 530/300, 324–330, 333, 334, 338

[56] References Cited

U.S. PATENT DOCUMENTS

| | | | |
|---|---|---|---|
| 4,390,528 | 6/1983 | Najjar | 424/177 |
| 4,427,646 | 1/1984 | Olexa et al. | 424/1.1 |
| 4,479,930 | 10/1984 | Hnatowich | 424/1.1 |
| 4,578,079 | 3/1986 | Ruoslahti et al. | 623/11 |
| 4,650,787 | 3/1987 | Schally et al. | 514/11 |
| 4,668,503 | 5/1987 | Hnatowich | 424/1.1 |
| 4,680,276 | 7/1987 | Bach et al. | 436/542 |
| 4,732,864 | 3/1988 | Tolman | 436/547 |
| 4,849,505 | 7/1989 | Stavrianopoulos | 530/300 |
| 4,859,765 | 8/1989 | Nester et al. | 530/333 |
| 4,863,898 | 9/1989 | Ashmead et al. | 514/6 |
| 4,883,861 | 11/1989 | Grill et al. | 530/326 |
| 4,986,979 | 1/1991 | Morgan et al. | 424/1.1 |
| 5,023,237 | 6/1991 | Pickart | 514/18 |
| 5,028,593 | 7/1991 | Nishioka | 514/18 |
| 5,053,393 | 10/1991 | Tjoeng et al. | 514/18 |
| 5,059,588 | 10/1991 | Pickart | 514/12 |
| 5,091,176 | 2/1992 | Braatz et al. | 424/78.17 |
| 5,118,665 | 6/1992 | Pickart | 514/6 |
| 5,157,023 | 10/1992 | Lipton | 514/18 |
| 5,196,510 | 3/1993 | Rodwell et al. | 530/324 |
| 5,200,504 | 4/1993 | Ghadiri | 530/304 |
| 5,214,131 | 5/1993 | Maeda et al. | 530/345 |
| 5,225,180 | 7/1993 | Dean et al. | 424/1.1 |
| 5,266,327 | 11/1993 | Agrez | 424/426 |
| 5,323,840 | 6/1994 | Coller | 435/240.2 |
| 5,371,184 | 12/1994 | Rajagopalan et al. | 530/324 |
| 5,382,654 | 1/1995 | Lyle et al. | 530/311 |
| 5,395,609 | 3/1995 | Stuttle | 424/1.69 |
| 5,408,036 | 4/1995 | Ghadiri | 530/304 |
| 5,410,020 | 4/1995 | Ghadiri | 530/333 |
| 5,438,119 | 8/1995 | Rutter et al. | 530/333 |
| 5,440,013 | 8/1995 | Kahn | 530/317 |
| 5,443,815 | 8/1995 | Dean et al. | 424/1.41 |
| 5,443,816 | 8/1995 | Zamora et al. | 424/1.69 |
| 5,464,934 | 11/1995 | Dunn et al. | 530/326 |
| 5,470,753 | 11/1995 | Sepetov et al. | 436/89 |
| 5,475,085 | 12/1995 | Kahn | 530/317 |
| 5,480,970 | 1/1996 | Pollak et al. | 530/328 |
| 5,556,609 | 9/1996 | Zamora | 424/1.69 |
| 5,567,408 | 10/1996 | Zamora | 424/1.69 |
| 5,569,745 | 10/1996 | Goodbody et al. | 530/328 |
| 5,659,041 | 8/1997 | Pollak et al. | 546/306 |
| 5,670,133 | 9/1997 | Zamora | 424/9.1 |
| 5,679,642 | 10/1997 | Goodbody et al. | 514/16 |

FOREIGN PATENT DOCUMENTS

| | | | |
|---|---|---|---|
| 2016235 | 11/1990 | Canada | C07K 7/06 |
| 607103 | 7/1994 | European Pat. Off. | C07K 7/26 |
| WO9015818 | 12/1990 | WIPO | C07K 5/08 |
| WO9213572 | 8/1992 | WIPO | A61K 49/02 |
| WO9310747 | 6/1993 | WIPO . | |
| WO9317719 | 9/1993 | WIPO | A61K 49/02 |
| WO9321962 | 11/1993 | WIPO | A61K 49/02 |
| WO9323085 | 11/1993 | WIPO | A61K 49/02 |
| WO9325244 | 12/1993 | WIPO | A61K 49/02 |
| WO9400489 | 1/1994 | WIPO | C07K 7/26 |
| WO9500553 | 1/1995 | WIPO | C07K 14/655 |
| WO9503330 | 2/1995 | WIPO | C07K 14/655 |

OTHER PUBLICATIONS

Fischman AJ, Babich JW, Strauss HW: A Ticket to Ride: Peptide Radiopharmaceuticals. *J Nucl Med* 34:2253–2263, 1993.

Fischman AJ, Pike MC, Kroon D, Fucello AJ, Rexinger D, tenKate C, Wilkinson R, Rubin RH and Strauss HW: Imaging focal sites of bacterial infection in rats with indium–111–labeled chemotactic peptide analogs. *J Nucl Med* 32:483–491, 1991.

Janeczek AH, Marasco WA, Van Alten PJ and Walter RB: Autoradiographic analysis of formylpeptide chemoattractant binding, uptaking and intracellular processing by neutrophils, *J Cell Sci* 94:155–168, 1989.

Babich JW, Graham W, Barrow SA, Dragotakes SC, Tompkins RG, Rubin RH and Fischman AJ: Technetium–99m–labeled chemotactic peptides: comparison with Indium–111–labeled white blood cells for localizing acute bacterial infection in the rabbit. *J Nucl Med* 34:2176–2181, 1993.

(List continued on next page.)

*Primary Examiner*—Jose' G. Dees
*Assistant Examiner*—Michael G. Hartley

[57] ABSTRACT

A peptide is provided for use as a diagnostic imaging, radiotherapeutic, or therapeutic agent, which peptide has a conformationally constrained global secondary structure obtained upon complexing with a metal ion. The peptide is of the general formula:

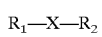

$$R_1-X-R_2$$

where X is a plurality of amino acids and includes a complexing backbone for complexing metal ions, so that substantially all of the valances of the metal ion are satisfied upon complexation of the metal ion with X, resulting in a specific regional secondary structure forming a part of the global secondary structure; and where $R_1$ and $R_2$ each include from 0 to about 20 amino acids, the amino acids being selected so that upon complexing the metal ion with X at least a portion of either $R_1$ or $R_2$, or both, have a structure forming the balance of the conformationally constrained global secondary structure. All or a portion of the global secondary structure, which may be sychnologic or rhegnylogic, may form a ligand or mimic a known biological-function domain. The peptide has substantially higher affinity when labeled with a metal ion. The peptide may be labeled with radioisotopes of technetium or rhenium for radiopharmaceutical applications.

44 Claims, 12 Drawing Sheets

OTHER PUBLICATIONS

Imura Y, Stassen J–M, Dunting S, Stockmans F, and Collen D: Antithrombotic properties of L–cysteine, N–(mercaptoacetyl)–D–Tyr–Arg–Gly–Asp–sulfoxide (G4120) in hamster platelet–rich femoral vein thrombosis model, *Blood* 80:1247–1253, 1992.

Knight LC, Radcliffe R, Maurer AH, Rodwell JD and Alvarez VL: Thrombus imaging with Tc–99m synthetic peptides based upon the binding domain of a monoclonal antibody to activated platelets. *J Nucl Med* 35:282–288, 1994.

Swanson D, Epperly M, Brown ML et al: In–111 laminin peptide fragments for malignant tumor detection. *J Nucl Med* 34:231P, 1993 (Abstract).

Wraight EP, Bard DR, Maughan TS et al: The Use of A Chelating Derivative of Alpha Melanocyte Stimulating Hormone for the Clinical Imaging of Malignant Melanoma, *Br J Radiology* 65:112–118, 1992.

Bard DR, Wraight EP, Knight CG: BisMSH–DTPA: a potential imaging agent for malignant melanoma, *Ann NY Acad Sci* 680:451–453, 1993.

Chou PY and Fasman GD: Prediction of the secondary structure of proteins from their amino acid sequence. In *Advances in Enzymology*, vol. 47 (1978) pp. 45–145, John Wiley & Sons, New York.

Hruby VJ: Conformational restrictions of biologically active peptides via amino acid side chain groups. *Life Sciences* 31:189–199, 1981.

Hruby VJ, Sharma SD, Collins N, Matsunaga TO and Russel KC: Synthetic Peptides, A *User's Guide* (selected portions), Grant GA, editor, W.H. Freedman and Company, 1992, pp. 259–345, 11–24, 24–33, 39–41, and 58–67.

Vallee BL and Auld DS: Zinc coordination, function, and structure of zinc enzymes and other proteins, *Biochemistry* 29:5648–5659, 1990.

Rhodes D and Klug A: Zinc fingers. *Scientific American* 268(2):56–65, 1993.

Krizek BA, Amann BT, Kilfoil VJ, Merkle DL, and Berg JM: A consensus zinc finger peptide: Design, high affinity metal binding, a pH–dependent structure, and a His to Cys sequence variant. *J. Amer. Chem Soc.* 113:4518–4523, 1991.

Shaw GS, Hodges RS, Sykes BD: Calcium–induced peptide association to form an intact protein domain: 1H NMR structural evidence. *Science* 249:280–283, 1990.

Reid RE, Gariepy J, Saund AK, Hodges RS: Calcium–Induced Protein Folding, *J. Biol. Chem.* 256:2742, 1981.

Lieberman M, Sasaki T: Iron(II) Organizes a Synthetic Peptide into Three–Helix Bundles, *J. Am. Chem. Soc.* 113:1470–1471, 1991.

Hruby VJ, Al–obeidi F and Kazmierski W: Emerging approaches in the molecular design of receptor–selective peptide ligands; conformational, topographical and dynamic consideration, *Biochem. J.* 268:249–262, 1990.

Toniolo C: Conformationally restricted peptides through short–range cyclization, *Int. J. Peptide Protein Res.* 35:287–300, 1990.

Ozeki E, Kimura S, and Imanishi Y: Conformation and Complexation with Metal Ions of Cyclic Hexapeptides: Cyclo (L–Lue–L–Phe–L–Pro)$_2$ and Cyclo [L–Cys(Acm)–L–Phe–L–Pro]$_2$. *Int. J. Peptide Protein Research* 34:111, 1989.

Garcia–Escheverria C, Albericio F, Giralt E and Pons M: *J. Amer. Chem. Soc.*, 115:11663–11670, 1992.

Chi DY, O'Neil JP, Anderson CJ, Welch MJ, and Katzenellenbogen JA: Homodimeric and heterodimeric bis(amino thiol) oxometal complexes with rhenium(V) and technetium(V): Control of heterodimeric complex formation and an approach to metal complexes that mimic steroid hormones. *J. Med. Chem.* 37:928–937, 1994.

Schwyzer R: Peptide–membrane interactions and a new principle in quantitative structure–activity relationships, *Biopolymers* 31:875–792, 1991.

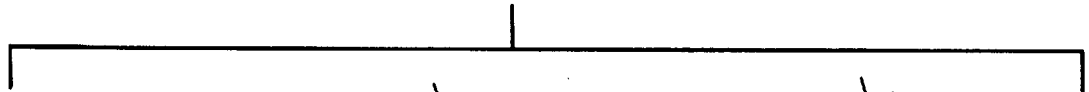
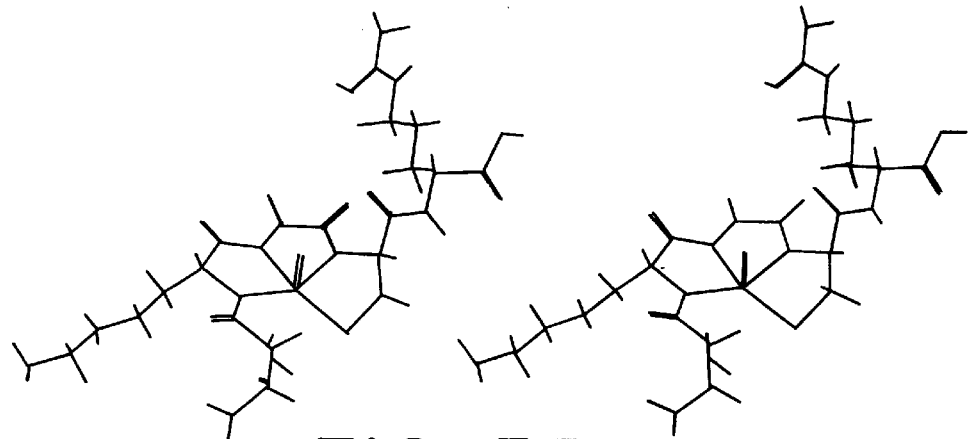
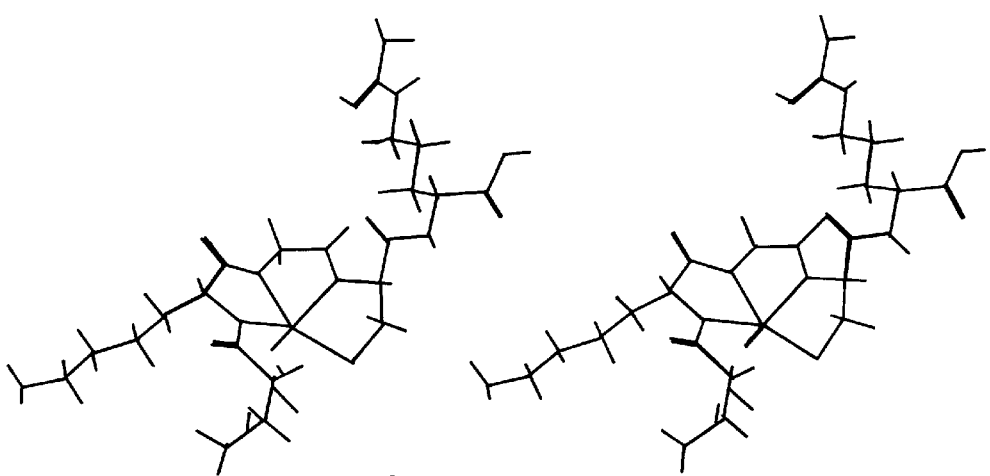
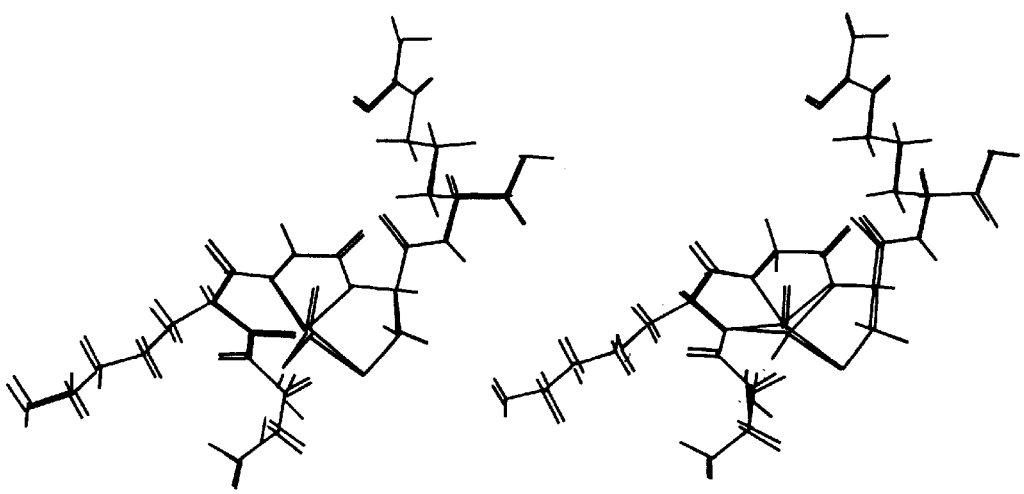

PEPTIDE-METAL ION PHARMACEUTICAL CONSTRUCTS AND APPLICATIONS

BACKGROUND OF THE INVENTION

1. Field of the Invention (Technical Field)

The present invention relates to peptide and peptidomimetic constructs, particularly for use in peptide receptor-based compositions for pharmaceutical and radiopharmaceutical applications, in which the peptide is conformationally fixed, with the biological-function domain having increased affinity for its target, upon labeling of the metal ion-binding backbone with a metal ion.

2. Background Art

Peptide Drugs. In recent years, a significant number of peptides have been discovered with various biological effects. These peptides are being explored for use as drugs, in treatment or prevention of a variety of diseases. There are significant limitations with use of peptide drugs, including extremely rapid clearance from the circulatory system, low affinity with some peptides, immunogenicity of larger peptide constructs, and lack of stability against proteolytic enzymes. However, there are peptides in use or under investigation as therapeutic agents for a number of conditions, including somatostatin analogues, arginine vasopression, oxytocin, luteinizing hormone releasing hormone, angiotensin converting enzyme, renin and elastase inhibitors, a variety of antagonists, including fibrinogen receptor antagonists, and the like. In addition, peptidomimetic antibiotics and peptide-based vaccines are also in use or development as human drugs.

The problems of immunogenicity and short circulatory half-life are well known, and various modifications to peptide-based drugs have been proposed in attempts to solve these problems. These include the modification of peptides or proteins with a variety of polymers, such as polyethylene glycol (PEG) and polypropylene glycol (PPG). Thus, in Braatz J A and Heifetz A H, U.S. Pat. No. 5,091,176, Polymer-Modified Peptide Drugs Having Enhanced Biological and Pharmacological Activities, a method is set forth for making polymer-modified drugs, with reduced immunogenicity, increased circulation half-life, and enhanced potency. A different method is disclosed in Sano A, Maeda H, Kai Y and One K, U.S. Pat. No. 5,214,131, Polyethylene Glycol Derivatives, Modified Peptides and Production Thereof.

Peptide-Based Radiopharmaceutical Drugs. The use of biologically active peptides, which are peptides which bind to specific cell surface receptors, has received some consideration as radiopharmaceuticals. Canadian Patent Application 2,016,235, Labeled Chemotactic Peptides to Image Focal Sites of Infection or Inflammation, teaches a method of detecting a site of infection or inflammation, and a method for treating such infection or inflammation, by administration of a labeled or therapeutically-conjugated chemotactic peptide. In this application, the chemotactic peptides are chemically conjugated to DTPA and subsequently labeled with [111]In. The utility of DTPA chelates covalently coupled to polypeptides and similar substances is well known in the art. Hnatowich D J, U.S. Pat. Nos. 4,479,930 and 4,668,503. Other bifunctional chelates for radiolabeling peptides, polypeptides and proteins are well known in the art. Biologically active peptides described include Olexa S A, Knight L C and Budzynski A Z, U.S. Pat. No. 4,427,646, Use of Radiolabeled Peptide Derived From Crosslinked Fibrin to Locate Thrombi In Vivo, in which iodination is discussed as a means of radiolabeling. In Rajagopalan R, Lyle L R and Dunn T J, U.S. Pat. No. 5,371,184, Radiolabelled Peptide Compounds, hirudin receptor-specific peptides, radiolabeled via a chelate ligand, are disclosed. In Morgan C A Jr and Anderson D C, U.S. Pat. No. 4,986,979, Imaging Tissue Sites of Inflammation, use of chelates and direct iodination is disclosed. In Tolman G L, U.S. Pat. No. 4,732,864, Trace-Labeled Conjugates of Metallothionein and Target-Seeking Biologically Active Molecules, the use of metallothionein or metallothionein fragments conjugated to a biologically active molecule, including peptides, is disclosed. In Dean R T and Lister-James J, International Application No. PCT/US93/05372, Technetium-99m Labeled Peptides for Imaging; Dean R T and Lister-James J, International Application No. PCT/US93/04794, Technetium-99m Labeled Peptides for Thrombus Imaging; Dean R T, Buttram S, McBride W, Lister-James J, and Civitello E R, International Application No. PCT/US93/03687, Technetium-99m Labeled Peptides for Imaging; Dean R T, Lees R S, Buttram S and Lister-James J, International Application No. PCT/US93/02320, Technetium-99m Labeled Peptides for Imaging Inflammation; and Dean R T, McBride W and Buttram S, International Application No. PCT/US92/10716, Technetium-99m Labeled Peptides for Imaging a variety of peptide constructs are disclosed, all involving a Tc-99m binding moiety covalently or otherwise linked to the peptide, or to a polyvalent linker moiety, which is itself linked to one or more peptides. These previous methods all employ some conjugation means with a chelator in order to effectuate labeling with a radionuclide or other medically useful metal ion, such as a paramagnetic contrast agent. The only exception involves direct radioiodination; the iodine labeling of proteins or peptides containing tyrosine or histidine residues is well known, for example, by the chloramine-T, iodine monochloride, lodogen or lactoperoxidase methods.

In Dean R T, Lister-James J and Buttram S, U.S. Pat. No. 5,225,180, Technetium-99m Labeled Somatostatin-Derived Peptides for Imaging, technetium-99m labeling of peptides containing at least two cysteine residues capable of forming a disulfide bond through reduction of the disulfide is disclosed. Other somatostatin-based radiopharmaceuticals are disclosed in Lyle L R, Rajagopalan R, Deutsch K, U.S. Pat. No. 5,382,654, Radiolabelled Peptide Compounds; Albert R and Mäcke H, International Application No. EP94810008.6, Somatostatin Analogs Containing Chelating Groups and Their Radiolabeled Compositions; Dean R T, McBride W and Lister-James J, International Application No. PCT/US94/06274, Radiolabeled Somatostatin-Derived Peptides for Imaging and Therapeutic Uses; and McBride W and Dean R T, International Application No. PCT/US94/08335, Somatostatin Derivatives and Their Radiolabelled Products. Use of peptide radiopharmaceuticals in general, not limited to somatostatin analogues, and various examples thereof, are given in Fischman A J, Babich J W, Strauss H W: A Ticket to Ride: Peptide Radiopharmaceuticals. *J Nucl Med* 34:2253–2263, 1993.

Other biologically active peptides include analogues of formyl peptide chemoattractants which bind to neutrophils. These peptides are based on the sequence N-formyl-Met-Leu-Phe (SEQ. ID NO. 1). The clinical and diagnostic imaging potential of formylated chemotactic peptides has been demonstrated by Fischman et al. (Fischman A J, Pike M C, Kroon D, Fucello A J, Rexinger D, tenKate C, Wilkinson R, Rubin R H and Strauss H W: Imaging focal sites of bacterial infection in rats with indium-111-labeled chemotactic peptide analogs. *J Nucl Med* 32:483–491, 1991) using chemotactic peptides chemically conjugated to DTPA and subsequently labeled with [111]In. Chemotactic peptides have also been radioiodinated by synthesizing formylated peptides containing tyrosine amino acids. These peptides have been used in vitro and have the same biological function as unlabeled formylated peptides (Janeczek A H, Marasco W A, Van Alten P J and Walter R B: Autoradiographic analysis of formylpeptide chemoattractant binding, uptake and intracellular processing by neutrophils. *J Cell Sci* 94:155–168, 1989). Finally, chemotactic peptides have also been labeled with $^{99m}$Tc using a nicotinyl hydrazine bifunctional chelate approach (Babich J W, Graham W, Barrow S A, Dragotakes S C, Tompkins R G, Rubin R H and Fischman A J: Technetium-99m-labeled chemotactic peptides: comparison with Indium-111-labeled white blood cells for localizing acute bacterial infection in the rabbit. *J Nucl Med* 34:2176–2181, 1993).

Peptides containing the adhesive sequence RGD are under active investigation as anti-thrombotic agents (Imura Y, Stassen J-M, Dunting S, Stockmans F, and Collen D: Antithrombotic properties of L-cysteine, N-(mercaptoacetyl)-D-Tyr-Arg-Gly-Asp-sulfoxide (G4120) in hamster platelet-rich femoral vein thrombosis model, *Blood* 80:1247–1253, 1992). Knight et al. (Knight L C, Radcliffe R, Maurer A H, Rodwell J D and Alvarez V L: Thrombus imaging with Tc-99m synthetic peptides based upon the binding domain of a monoclonal antibody to activated platelets. *J Nucl Med* 35:282–288, 1994) have reported on the use of $^{99m}$Tc-synthetic peptide-metallothionein complexes, containing the radiometal binding sequence Lys-Cys-Thr-Cys-Cys-Ala (SEQ. ID NO. 2), which bind to the platelet glycoprotein IIb/IIIa complex to image fresh thrombi in jugular and femoral veins. Other RGD-containing sequences are disclosed in Stuttle A W J, U.S. Pat. No. 5,395,609, Synthetic Peptides for Use in Tumor Detection.

Radiolabeled peptide constructs, with two binding sequences coupled to DTPA, have been reported. A dimer $^{111}$In-DTPA-labeled laminin sequence was prepared for tumor imaging, in which the dimer was formed by reacting a peptide sequence containing a single YIGSR with DTPA dianhydride, yielding a dimer represented by the formula DTPA-(GYIGSR-NH$_2$)$_2$ (derived from SEQ. ID NO. 3). In preliminary studies the dimer was more potent than a peptide with a single YIGSR (SEQ. ID NO. 3) sequence. Swanson D, Epperly M, Brown M L et al: In-111 laminin peptide fragments for malignant tumor detection. *J Nucl Med* 34:231P, 1993 (Abstract). A dimer of a melanotropin analogue linked to $^{111}$In-DTPA in a similar fashion has also been reported as an imaging agent for metastatic melanoma. Wraight E P, Bard D R, Maughan T S et al, *Br J Radiology* 65:112–118, 1992; and Bard D R, Wraight E P, Knight C G: BisMSH-DTPA: a potential imaging agent for malignant melanoma. *Ann NY Acad Sci* 680:451–453, 1993.

Structure of Peptides. The folding of linear chain amino acids in peptides and proteins in a very distinctive manner is responsible for their unique three dimensional structure. It is now clear that the side chains of individual amino acids have preferential propensity to nucleate a particular secondary structure (Chou P Y and Fasman G D: Prediction of the secondary structure of proteins from their amino acid sequence. In *Advances in Enzymology*, Vol. 47 (1978) pp. 45–145, John Wiley & Sons, New York). The properties of these side chains, such as steric bulk and inherent hydropathicity, cause the peptide chain to fold as a helix, sheet, or a reversed turn. In addition to these local effects, both covalent as well as noncovalent interactions between distant as well as adjacent amino acids in the chain also play a very important role in determining, stabilizing and biasing a particular three dimensional structure. Examples of non-covalent interactions include hydrophobic interactions, van der Waals' forces, and hydrogen bonds. Electrostatic interactions in the form of a salt bridge between a positively charged side chain and a negatively charged side chain are common, and stabilize a peptide or protein in a particular configuration. The most important type of covalent interaction between two amino acids in a chain is the formation of a disulfide linkage between two Cys residues that nucleates a particular conformational preference in the molecules. These interactions can be short range (local or regional) or long range (global).

Most of the elements for inducing and stabilizing a conformational preference in naturally occurring proteins and peptides have been used to design and synthesize a wide variety of peptide analogues with preferred or biased conformational characteristics. Examples of structural changes in peptides to cause conformational biasness and restriction have been discussed in the literature (Hruby V J: Conformational restrictions of biologically active peptides via amino acid side chain groups. *Life Sciences* 31:189–199, 1981). The incorporation of modified amino acids, such as N$^\alpha$-Methyl or C$^\alpha$-Methyl amino acids or other designer amino acids with conformationally restricted side chains, cause a strong local conformational effect. In synthetic peptides long range or global conformational restriction can routinely be achieved by cyclizing a peptide through appropriate amino acid end groups or side chains. The types of cyclic bridges commonly employed are disulfide bridges between two Cys residues in the peptide chain, and related thioester and thioether bridges, and formation of a lactam or lactone bridge between appropriate chemical groups in the amino acid side chains. Numerous highly potent analogues of many biologically active peptides have been designed using these approaches. Examples include peptide hormones such as somatostatin, opioid peptide, melanotropin, neurokinins, glucagon, and ACTH analogues. Hruby V J, Sharma S D, Collins N, Matsunaga T O and Russel K C: Applications of synthetic peptides, in *Synthetic Peptides, A User's Guide*, Grant G A, editor, W. H. Freedman and Company, 1992, pp. 259–345.

Peptide—Metal Ion Interaction. Metal ion complexation within a given amino acid sequence, such as encountered in certain proteins, also appears to effect conformational restriction. Specific structures, called Zinc fingers, in various DNA transcription factors result from complexation of Zn ion to a specific amino acid sequence in the protein. In Vallee B L and Auld D S: Zinc coordination, function, and structure of zinc enzymes and other proteins, *Biochemistry* 29:5648–5659, 1990, the general characteristics of non-metallothionein proteins which contain zinc binding sites are described. Similarly, a family of calcium binding proteins, including calmodulin and related proteins, have highly conserved domains for complexation of Ca ions. These metal binding proteins have unique functional roles in the body that are displayed after the metal ion has complexed to them. The complexation process is known to cause a switch in conformational characteristics which in turn triggers the functional response exerted by the protein.

The area of peptide-metal ion complex receiving the most interest involves zinc fingers, natural sequences with specific Zn binding domains in transcription proteins that mediate gene regulation (Rhodes D and Klug A: Zinc fingers. *Scientific American* 268(2):56–65, 1993. The reported zinc fingers which have been synthesized and studied for metal binding characteristics in respect to conformational restriction and peptide folding are not of biological relevance, since they are not capable of establishing site-specific interactions with DNA in a manner similar to the transcription proteins that incorporate these zinc fingers. Krizek B A, Amann B T, Kilfoil V J, Merkle D L, and Berg J M: A consensus zinc finger peptide: Design, high affinity metal binding, a pH-dependent structure, and a His to Cys sequence variant. *J. Amer. Chem Soc.* 113:4518–4523, 1991.

Metal ion induced switches in the tertiary structure of synthetic peptides have been shown in some model studies. Reid, Hodges and co-workers (Shaw G S, Hodges R S, Sykes B D: Calcium-induced peptide association to form an intact protein domain: 1H NMR structural evidence. *Science* 249:280, 1990; and Reid R E, Gariepy J, Saund A K, Hodges R S: *J. Biol. Chem.* 256:2742, 1981) showed that a peptide fragment related to a natural calcium binding protein exhibits enhanced α-helical structure upon binding to calcium. This is due to dimerization of two helical peptide segments located at each end, which is induced by complexation of a calcium ion in the middle peptide segment. Sasaki and co-workers (Lieberman M, Sasaki T: *J. Am. Chem. Soc.* 113:1470, 1991) have attached a metal binding chelator to one end of a peptide with a low propensity to form an α-helical structure. Upon complexation with iron ion three peptide-chelator molecules complex with one metal ion to form a helix bundle. Formation of three-dimensional arrays of the existing secondary structure in these examples, although caused by the complexing metal ion, is not entirely stabilized by it. The helical segments involved in forming a bundle of two or three helices are amphiphilic. The main role of complexing metal ion in these cases has been to bring these amphiphilic helices close enough so that they interact with each other through amphiphilic interactions, thereby stabilizing the helical bundle.

SUMMARY OF THE INVENTION (DISCLOSURE OF THE INVENTION)

In accordance with the present invention, there is provided a manufactured peptide and pharmaceutically acceptable salts thereof that has a conformationally constrained secondary or three-dimensional structure, including a global structure, obtained upon complexing with a metal ion, the peptide being of the general formula:

$$R_1-X-R_2$$

wherein X is a complexing backbone for complexing metal ions including a plurality of amino acids, so that substantially all of the valances of the metal ion are satisfied upon complexation of the metal ion with X;

wherein X has, upon complexing with the metal ion, a specific regional secondary structure forming a part of the global secondary structure; and wherein $R_1$ and $R_2$ each comprise from 0 to about 20 amino acids, the amino acids being selected so that upon complexing the metal ion with X at least a portion of either $R_1$ or $R_2$ or both have a structure forming the balance of the conformationally constrained global secondary structure.

In this peptide, X includes amino acids containing at least one nitrogen (also called an "N"), sulfur (also called an "S") or oxygen (also called an "O") atom available for complexing with the available valences of the metal ion. If less than all of the valances of the metal ion are satisfied upon complexation of the metal ion with the amino acids included in X, then X may also include a derivatized peptide or spacer sequence, which derivatized peptide or spacer sequence itself includes at least one nitrogen, sulfur or oxygen atom available for complexing with the available valences of the metal ion, so that all of the valences of the metal ion are satisfied upon complexation of the metal ion with X. Particularly with metal ions with a coordination number of 4, a preferred global secondary structure is achieved only if all the valences of the metal ion are satisfied, either through amino acids or through a combination of amino acids and either derivatized amino acids or spacer sequences. However, if at least two of the four valences of the metal ion are satisfied, it is possible to obtain a sufficient secondary or three-dimensional structure. For metal ions with a coordination number of 5 or 6, it is possible to achieve the desired global secondary structure even though less than all the valences of the metal ion are satisfied.

In the peptide, all or a portion of the conformationally constrained global secondary structure may be a ligand capable of forming a member of a ligand and receptor pair. In general, the affinity of the ligand portion of the conformationally constrained global secondary structure for its receptor upon complexing with a metal ion is substantially higher than the affinity of the peptide which is not conformationally constrained in a global secondary structure with a metal ion. Similarly, at least a portion of the conformationally constrained global secondary structure may mimic a known biological-function domain.

The peptide may also be defined so as to include a metal ion complexed to X. The metal ion may be an ionic form of the element iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium or astatine. The metal ion may also be a medically useful metal ion, which may be radioactive or paramagnetic.

The peptide may be a cyclic peptide of the formula:

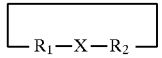

wherein $R_1$ and $R_2$ are covalently linked together.

In this cyclic peptide, $R_1$ and $R_2$ may be covalently linked together through an amide, disulfide, thioether, thioester or ester linkages. Similarly, the covalent linkage between $R_1$ and $R_2$ may be a linkage through the end groups of $R_1$ and $R_2$, a linkage through side chain functionalities of any amino acid within $R_1$ and $R_2$, a linkage through the end group of $R_1$ and a side chain functionality of any amino acid in $R_2$, or a linkage through the end group of $R_2$ and a side chain functionality of any amino acid in $R_1$. The cyclic peptide may also be of the formula:

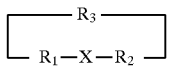

wherein $R_3$ includes from 1 to about 20 amino acids.

In this configuration, $R_3$ may form a part of the conformationally constrained global conformation. In this event, $R_3$ may be either sychnological or rhegnylogical with either $R_1$ and $R_2$ or both $R_1$ and $R_2$.

In accordance with the present invention, there is also provided a method of making a peptide and pharmaceutically acceptable salts thereof that has a conformationally constrained global secondary structure obtained upon complexing with a metal ion, which method includes the steps of:

a) providing a peptide of the general formula:

wherein X is a complexing backbone for complexing metal ion including a plurality of amino acids, so that substantially all of said valances of the metal ion are satisfied upon complexation of the metal ion with X, wherein X has, upon complexing with the metal ion, a specific regional secondary structure forming a part of the global secondary structure, and wherein $R_1$ and $R_2$ each comprise from 0 to about 20 amino acids, the amino acids being selected so that upon complexing the metal ion with X at least a portion of either $R_1$ or $R_2$ or both have a structure forming the balance of the conformationally constrained global secondary structure; and b) complexing a metal ion to the peptide.

In this method, X may be amino acids containing at least one nitrogen, sulfur or oxygen atom available for complexing with the available valences of the metal ion. If less than all of the valances of the metal ion are satisfied upon complexation of the metal ion with the amino acids included in X, then X may also include a derivatized peptide or spacer sequence, which derivatized peptide or spacer sequence itself includes at least one nitrogen, sulfur or oxygen atom available for complexing with the available valences of the metal ion, so that all of the valences of the metal ion are satisfied upon complexation of the metal ion with X.

The invention also provides a method of making a peptide or pharmaceutically acceptable salts thereof in which a conformationally constrained global secondary structure includes a ligand capable of forming a member of a ligand and receptor pair, the method consisting of the steps of:

a) providing a peptide of the general formula:

wherein X is a complexing backbone for complexing metal ion including a plurality of amino acids, so that substantially all of said valances of the metal ion are satisfied upon complexation of the metal ion with X, wherein X has, upon complexing with the metal ion, a specific regional secondary structure forming a part of the conformationally constrained global secondary structure, wherein $R_1$ and $R_2$ each comprise from 0 to about 20 amino acids, the amino acids being selected so that upon complexing the metal ion with X at least a portion of either $R_1$ or $R_2$ or both have a structure forming the balance of the conformationally constrained global secondary structure, and wherein the conformationally constrained global secondary structure made up of at least a part of X, $R_1$ and $R_2$ are a ligand capable of forming a member of a ligand and receptor pair; and b) complexing a metal ion to the peptide;

whereby the metal ion causes X to form a specific regional secondary structure, thereby causing the peptide to be configured as a conformationally constrained global secondary structure comprising a ligand capable of forming a member of a ligand and receptor pair.

The affinity for its receptor of the conformationally constrained global secondary structure constituting a ligand is substantially higher than the affinity of the peptide which is not conformationally constrained in a global secondary structure with a metal ion.

There is also provided a method of making a peptide or a pharmaceutically acceptable salt thereof that includes an amino acid sequence which mimics a known biological-function domain, the method including the steps of:

a) providing a complexing backbone for complexing metal ion, the backbone including a plurality of amino acids selected so that substantially all of the valances of the metal ion are satisfied upon complexation of the metal ion with the complexing backbone, the metal ion to be provided, and which complexing backbone is homologous with at least a portion of the biological-function domain upon labeling of the complexing backbone with the metal ion;

b) providing from 0 to about 20 amino acids linked to either end of the complexing backbone, which amino acids are selected so that the peptide is homologous with the remainder of the biological-function domain upon labeling of the complexing backbone with a metal ion; and c) complexing the complexing backbone with a metal ion.

In this method, the side chains of the amino acids included in the complexing backbone may be modified to increase the homology of the complexing backbone with at least a portion of the biological-function domain upon labeling of the complexing backbone with a metal ion. In general, upon labeling the complexing backbone with a metal ion, the complexing backbone forms a specific regional secondary structure. The complexing backbone forming a specific regional secondary structures then causes the peptide to be configured with a conformationally constrained global secondary structure.

In this method, the complexing backbone includes amino acids containing at least one nitrogen, sulfur or oxygen atom available for complexing with the available valences of the metal ion. If less than all of the valances of the metal ion are satisfied upon complexation of the metal ion with the amino acids comprising the complexing backbone, then the complexing backbone may also include a derivatized peptide or spacer sequence, which derivatized peptide or spacer sequence itself includes at least one nitrogen, sulfur or oxygen atom available for complexing with the available valences of the metal ion, so that all of the valences of the metal ion are satisfied upon complexation of the metal ion with the complexing backbone.

Also provided is a manufactured peptide and pharmaceutically acceptable salts thereof which include a metal ion-binding backbone and a determined biological-function domain, and in which the biological-function domain is conformationally constrained only upon labeling the metal ion-binding backbone with a metal ion. In this method, at least a portion of the peptide may be conformationally constrained in a secondary structure upon labeling the metal ion-binding backbone with a metal ion. Similarly, the peptide may have a conformationally constrained global secondary structure upon labeling the metal ion-binding backbone with a metal ion. In these peptides, the biological-function domain may be substantially inactive until the metal ion-binding backbone is labeled with a metal ion.

The metal ion-binding backbone of these peptides may include a plurality of amino acids, so that all of the valances of the metal ion are satisfied upon complexation of the metal ion. These amino acids may each contain at least one nitrogen, sulfur or oxygen atom available for complexing with the available valences of the metal ion. If less than all of the valances of the metal ion are satisfied upon complexation of the metal ion with the amino acids of the metal ion-binding backbone, then the metal ion-binding backbone may also include a derivatized peptide or spacer sequence, which derivatized peptide or spacer sequence itself includes at least one nitrogen, sulfur or oxygen atom available for complexing with the available valences of the metal ion, so that all of the valences of the metal ion are satisfied upon complexation of the metal ion.

The biological-function domain of the peptide may include a ligand capable of forming a member of a ligand and receptor pair. The affinity of this ligand for its receptor is substantially higher when the metal ion-binding backbone of the peptide is labeled with a metal ion than is the affinity of the peptide when the metal ion-binding backbone is not labeled with a metal ion. Upon labeling the metal ion-binding backbone with a metal ion the biological-function domain may be either sychnological or rhegnylogical.

This peptide also may include a metal ion, so that there is a metal ion labeled binding backbone forming a part of the peptide. The metal ion may be an ionic form of the element iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium or astatine. Similarly, the metal ion may be a medically useful metal ion, which may be radioactive or paramagnetic.

The peptide may be a cyclic peptide, which may be cyclicized through an amide, disulfide, thioether, thioester, or ester linkages. Cyclicization may be through a covalent linkage through the end groups of the peptide, covalent linkage through side chain functionalities of any two amino acids within the peptide, or covalent linkage through one end group of the peptide and a side chain functionality of any amino acid in the peptide.

The peptide may have a determined biological-function domain, upon becoming conformationally constrained in a secondary structure by labeling the metal ion-binding backbone with a metal ion, which is specific for receptors to the tripeptide sequence Arg-Gly-Asp. This includes peptides of the formula:

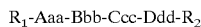

wherein
  Aaa is an amino acid with a positively charged side chain, and containing a N which can be available for binding a metal ion;
  Bbb is an amino acid with one or more uncharged side chains;
  Ccc is an amino acid containing a S and a N which can be available for binding a metal ion;
  Ddd is Gly, Ala or an amino acid with a negatively charged functional group;
  $R_1$ is H, alkyl, aryl, alkylcarbonyl, arylcarbonyl, alkyloxycarbonyl, aryloxycarbonyl, or a polymer attached directly or through a carbonyl group; and
  $R_2$ is, if Ddd is other than Gly, Ala, β-Ala, N-Me-β-Ala, or a higher homologue of β-Ala, an amide or substituted amide.

For peptides of this formula, Aaa may be a L- or D-isomer of Arg, N-Me-Arg, N-Me-Arg, alkylated or arylated Arg, Orn, homoArg, S-(2-aminoethyl)Cys, O-(2-aminoethyl)Ser, or N-alkylated or arylated derivatives thereof. Bbb may be an amino acid such as L- or D-isomers of Gly, Ala, Aib, Val, Nle, and Leu. Ccc may be a L- or D-isomer of Cys, HomoCys, or Pen. Ddd may be a L- or D-isomer of β-Ala, N-Me-β-Ala, higher homologue of β-Ala, Asp, N-Me-Asp, Glu, or N-Me-Glu. Peptides of this formula include peptides with the primary sequence D-Arg-Gly-D-Cys-β-Ala. This peptide may be labeled with a gamma emitting metal ion, and used for imaging of thrombosis, cancer or acute renal failure, including detection of tubular obstruction, or labeled with an alpha or beta emitting metal ion, and used for myocardial infarction therapy.

The peptide may also have a determined biological-function domain, upon becoming conformnationally constrained in a secondary structure upon labeling the metal ion-binding backbone with a metal ion, that is specific for the tuftsin receptor. This peptide may have the formula:

wherein
  Aaa is a L- or D-isomer of Thr, Cys, Pen, or Ser and corresponding des-amino derivatives;
  Bbb is an amino acid with a positively charged side chain and containing a N which can be available for binding a metal ion;
  Ccc is an amino acid with an un-charged side chain and containing a N which can be available for binding a metal ion;
  Ddd is an amino acid containing a S or a S and a N which can be available for binding a metal ion;
  Eee is an amino acid with a positively charged side chain;
  $R_1$ is H, alkyl, aryl, alkylcarbonyl, arylcarbonyl, alkyloxycarbonyl, aryloxycarbonyl, or a polymer attached directly or through a carbonyl group, unless Aaa is a des-amino amino acid, in which case $R_1$ does not exist; and
  $R_2$ is, an amide, substituted amide, ester, or a polymer unless Eee is a des-carboxyl amino acid, in which case $R_2$ does not exist.

For peptides of this formula, Aaa may be a L- or D-isomer of Thr, Cys, Pen, or Ser or corresponding des-amino derivatives. Bbb may be an L- or D-isomers of Arg, Lys, Orn, homoArg, S-(2-aminoethyl)Cys, O-(2-aminoethyl)Ser or derivatives thereof. Ccc may be an L- or D-isomer of Gly, Ala, Aib, Val, Nle, or Leu. Ddd may be an L- or D-isomer of Cys, HomoCys, or Pen. Eee may be an L- or D-isomer of L- or D-isomers of Arg, Lys, Orn, homoArg, S-(2-aminoethyl)Cys, O-(2-aminoethyl)Ser or corresponding des-carboxyl derivatives. Peptides of this formula thus include Thr-D-Lys-Gly-D-Cys-Arg. These peptides may be labeled with a gamma emitting metal ion for diagnostic imaging of sites of infection or inflammation.

This invention also includes cyclic peptides, and pharmaceutically acceptable salts thereof, with a metal ion-binding backbone for isosteric replacement of a disulfide, thioether, thioester, lactam, or a lactone bridge. These cyclic peptide are of the general formula:

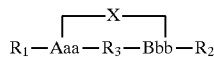

wherein X is a complexing backbone for complexing metal ion including a plurality of amino acids, so that substantially all of said valances of the metal ion are satisfied upon complexation of the metal ion with X,
wherein $R_1$ and $R_2$ each comprise from 0 to about 20 amino acids,
wherein $R_3$ comprises from 1 to about 20 amino acids, and
wherein Aaa and Bbb each comprise an amino acid connected to X through an amide, thioether, thioester or ester bond.

Cyclic peptides of this formula include those in which X includes amino acids containing at least one nitrogen, sulfur or oxygen atom available for complexing with the available valences of the metal ion. If less than all of the valances of the metal ion are satisfied upon complexation of the metal ion with the amino acids of X, then X may also include a derivatized peptide or spacer sequence, which derivatized peptide or spacer sequence itself includes at least one nitrogen, sulfur or oxygen atom available for complexing with the available valences of the metal ion, so that all of said valences of the metal ion are satisfied upon complexation of the metal ion with X. In any event, X may be an amino acid sequence of the formula Ccc-Ddd-Eee, in which each of Ccc and Ddd is an amino acid or dipeptide with uncharged side chains, and Eee is an L- or D-isomer of Cys, HomoCys, or Pen. Ccc and Ddd may be L- or D-isomers of Gly, Ala, Aib, Val, Nle, or Leu. Aaa may be L- or D-isomer of an amino acid terminating in a carboxyl group or in an amine group. Generally Bbb is a L- or D-isomer of an amino acids terminating in a carboxyl group or in an amino group, such that if Bbb has a side chain terminating in a carboxyl group, Eee has a side chain terminating in an amino group, and if Bbb has a side chain terminating in an amino group, Eee has a side chain terminating in a carboxyl group. Also provided are cyclic peptides in which Aaa terminates in a carboxyl group and is a L- or D-isomer of Asp or Glu, and also in which Ddd terminates in an amine group and is an L- or D-isomer of Orn or Lys.

This cyclic peptide may also include a metal ion complexed to X. The metal ion may be an ionic form of the element iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium or astatine. Similarly, the metal ion may be a medically useful metal ion. This metal ion may be radioactive or paramagnetic.

This cyclic peptide includes somatostatin analogues of the formula:

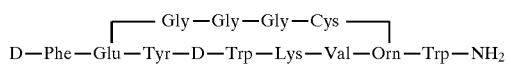

melanotropin analogues of the formula:

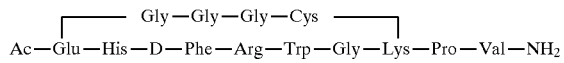

and melanotropin analogues of the formula:

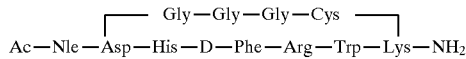

In accordance with the present invention, there is also provided a peptide-based pharmaceutical composition suitable for administration to a patient, which composition includes:

a peptide which includes a metal ion-binding backbone and a determined biological-function domain, which biological-function domain is conformationally constrained only upon labeling the metal ion-binding backbone with a metal ion; and a metal ion labeling agent.

In one embodiment, at least a portion of the peptide is conformationally constrained in a secondary structure upon labeling the metal ion-binding backbone with a metal ion. Similarly, the biological-function domain may be substantially inactive until the metal ion-binding backbone is labeled with a metal ion. The metal ion-binding backbone may include a complexing backbone for complexing metal ion composed of a plurality of amino acids, so that all of the valances of the metal ion are satisfied upon complexation of the metal ion. The amino acids may each contain at least one nitrogen, sulfur or oxygen atom available for complexing with the available valences of the metal ion. If less than all of the valances of the metal ion are satisfied upon complexation of the metal ion with the amino acids of the metal ion-binding backbone, then the metal ion-binding backbone may also include a derivatized peptide or spacer sequence, which derivatized peptide or spacer sequence itself includes at least one nitrogen, sulfur or oxygen atom available for complexing with the available valences of the metal ion, so that all of the valences of the metal ion are satisfied upon complexation of the metal ion.

The peptide-based pharmaceutical composition includes metal ion labeling agents which include a stannous ion agent. Representative stannous ion agents include stannous tartrate, stannous glucoheptonate, stannous gluconate, stannous phosphonate, stannous chloride, stannous sulfate, stannous acetate, and stannous fluoride. The peptide-based pharmaceutical composition may include a stannous ion agent present in a solution including alkali metal tartrate as well as a dicarboxylic acid, such as phthalate, tartrate or citrate.

It is one objective of this invention to device, demonstrate and illustrate making and using highly specific conformational restrictions in peptides, peptoids, related pseudopeptides, and peptidomimetics by complexing sequences thereof to a desired metal ion so that the topography of the side chains in the resulting complex is a biologically active three-dimensional structure which binds to a known biological receptor.

Another objective of the invention is to employ this approach to obtain radiolabeled molecules in a carrier-free state, so that only metal ion complexed molecules are biologically active, for radioimaging, radiation therapy, positron emission tomography (PET) and the like.

Another objective of the invention is to provide a method for designing a series of molecular moieties, each capable of complexing metal ion in a specific manner as replacement for a disulfide, a lactam, or a lactone bridge in a peptide, whereby there is conformational restriction in a peptide-related segment upon complexation with the metal ion. The topography of the side chains in the metal ion complexed molecule resemble that of the corresponding disulfide, lactam, or lactone congener.

Another objective of the invention is to provide peptide-metal ion complexes such that the peptide-metal ion complex displays a higher level of stability and is less susceptible to proteolysis than is the peptide not complexed to a metal ion.

Yet another objective of the invention is to provide for peptide analogues which lack conformational restriction if not complexed with a metal ion, so that the uncomplexed peptide analogue is either inactive or demonstrates low potency, but which demonstrates high potency, and concomitant conformational restriction, upon complexation with a metal ion, including a radiometal ion.

It is yet another objective of the invention to provide conformationally constrained peptide-metal ion complexes as surrogates for reverse turn structures, such as beta turns and gamma turns commonly found in naturally occurring peptides and proteins, whereby the turns formed as a consequence of metal ion complexation are more stable than the naturally occurring turn structures which are stabilized only by weaker interactions such as van der Waals' interactions and hydrogen bonds.

Another objective of the invention is to utilize metal complexation in a peptide to cause specific regional conformational restrictions in the peptide so that the peptide conformation at the metal binding site is conformationally fixed upon metal complexation.

Yet another objective of the invention is to utilize metal ion complexation in a peptide to effect specific global conformational restrictions in the peptide so that the regional conformational restrictions caused by complexing metal ion to a sequence including amino acid residues in turn cause conformational restriction on distal regions of the peptide.

Yet another objective of the invention is to utilize metal ion complexation in a linear peptide to fold and conformationally restrict the peptide to obtain conformational restriction comparable to that obtainable by cyclizing the peptide through a disulfide, lactam or similar group.

It is yet another objective of the invention to complex peptide to a metal ion so as to alter the in vivo biodistribution profile, rate and mode of clearance from the body, bioavailability and pharmacokinetics in mammalian animals.

Another objective of the invention is to design and develop a molecule which, upon complexing with a metal ion, includes a biological-function domain which is specific for platelet fibronectin receptor (RGD receptor) for use in diagnostics and therapeutic modalities such as thrombus imaging, imaging kidney damage, imaging and therapy of tumor lesions and imaging and therapy of myocardial infarction.

Yet another objective of this invention is to design and develop a molecule which, upon complexing with a metal ion, includes a biological-function domain which is specific for tuftsin receptors, and which stimulates polymorphonuclear granulocytes, monocytes and macrophages towards phagocytosis and may be used in diagnostic modalities for abscess and infection imaging.

Yet another objective of the invention is to provide a peptide-metal ion complex with a region specific for the tuftsin receptor on polymorphonuclear granulocytes and macrophages, the presence of which complex increases the antigenic profile of antigens presented to such polymorphonuclear granulocytes and macrophages, thereby resulting in production of higher titer antibodies.

Yet another objective of this invention is to design and develop a somatostatin analogue wherein the disulfide bond in somatostatin is substituted by a specific metal ion-complexing moiety, so that after complexation of a metal ion to the moiety, the topography of the receptor binding region is fixed and is similar to that in the original disulfide-containing somatostatin molecule.

Yet another objective of the invention is to demonstrate the displacement of a lactam bridge in a potent melanotropin analogue containing a cyclic lactam bridge by a specific metal ion-binding moiety so that the molecule is potent, and binds to a designated receptor, only after complexation of the metal ion.

Yet another objective of the invention is to develop a peptide-metal ion ligand for the estrogen receptor by de novo design so that the ligand binds the estrogen receptor only after its complexation with a metal ion.

Yet another objective of the invention is to complex peptides with a radiometal ion for use in whole body imaging and radiotherapy so that the resulting peptide-metal complex is of higher affinity and specificity for the tissue target than the uncomplexed peptide molecule. The resulting radiolabeled species therefore is essentially carrier-free in terms of biological target recognition.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 1-A depicts a naturally occurring reverse turn structure, such as a portion of a larger peptide or protein wherein the reverse turn is located between two anti-parallel β-sheets. FIG. 1-B schematically depicts a peptide of this invention with random conformation, which is not complexed with a metal ion. FIG. 1-C depicts a peptide of this invention which is complexed with a metal ion. This complexation forms a reverse turn structure, yielding a highly constrained structure.

FIGS. 2-A and 2-B show the two isomers created by the isomerism in the metal oxo group. FIG. 2-C shows the figures of FIGS. 2-A and 2-B superimposed, demonstrating that there is no difference in topography of the biologically relevant amino acid side chains between the two isomers.

FIG. 3 shows a relaxed stereo view of a metal ion-labeled peptide of this invention with a primary unlabeled structure of Thr-D-Lys-Gly-D-Cys-Arg. FIGS. 3-A and 3-B show the two isomers created by the isomerism in the metal oxo group. FIG. 3-C shows the figures of FIGS. 3-A and 3-B superimposed, demonstrating that there is no difference in topography of the biologically relevant amino acid side chains between the two isomers.

DETAILED DESCRIPTION OF THE PREFERRED EMBODIMENTS OF THE INVENTION

(BEST MODES FOR CARRYING OUT THE INVENTION)

Figure 1A:
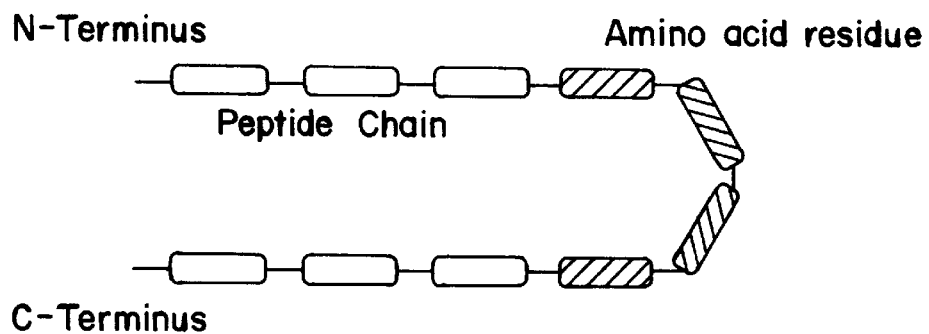
FIG. 1 schematically depicts a linear peptide made by this invention, both prior to complexing with a metal ion wherein it is not conformationally constrained, and after complexing with a metal ion wherein it is conformationally constrained.

Using the methods of this invention, peptide metal-ion complexes are designed by selecting a peptide chain which encompasses the groups that individually are necessary for providing a coordination site for complexation with a metal ion. Specific stereochemical features of this peptide-metal ion complex are due to the stereochemistry of the coordination sphere of the complexing metal ion. Thus the defined geometry of the coordination sphere of the incoming metal ion dictates and defines the nature and extent of the conformational restriction imposed on the peptide backbone.

While it is known that a complexing metal ion can nucleate a particular conformational preference in a peptide chain, and this approach has been demonstrated to cause the formation of a tertiary structure from the existing domains of the secondary structure, utilization of metal complexation to force conformational restriction so as to induce a preferential secondary structure that is relevant to a given biological receptor has heretofore remained unexplored. This approach presents significant advantages, because shorter peptides do not generally exhibit preferred solution conformation, and generally are characterized by substantial segmental flexibility. For peptides in which secondary structure is important, such as short peptides containing sequences which bind to biological receptors, some form of chemical modification is required to decrease conformational flexibility.

Definitions. Certain terms as used throughout the specification and claims are defined.

The terms "bind," "binding," "label", "labeling", "complex," and "complexing," as used throughout the specification and claims, are intended to cover all types of physical and chemical binding, reactions, complexing, attraction, chelating and the like.

The peptides of the invention can be:

a) naturally-occurring,
b) produced by chemical synthesis,
c) produced by recombinant DNA technology,
d) produced by biochemical or enzymatic fragmentation of larger molecules,
e) produced by methods resulting from a combination of a–d, or
f) produced by any other means for producing peptides.

By employing chemical synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like. The term "peptide" as used throughout the specification and claims is intended to include any structure comprised of two or more amino acids, including derivatives of amino acids. For the most part, the peptides of this invention comprise fewer than 100 amino acids, and preferably fewer than 60 amino acids, and most preferably ranging from about 2 to 20 amino acids. The amino acids forming all or a part of the peptide may be naturally occurring amino acids, isomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics. The term "peptide" also includes dimers or multimers of peptides.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. The term "amino acid" also includes isomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, G A Grant, editor, W. H. Freeman & Co., New York, 1992; Hruby V J, Al-obeidi F and Kazmierski W: Emerging approaches in the molecular design of receptor-selective peptide ligands; conformational, topographical and dynamic consideration, *Biochem. J.* 268:249–262, 1990; and Toniolo C: Conformationally restricted peptides through short-range cyclization, *Int. J. Peptide Protein Res.* 35:287–300, 1990; the teachings of all of which are incorporated herein by reference.

The peptide constructs of this invention also include a metal ion, and for medical embodiments a medically useful metal ion. The metal ion may be radioactive, paramagnetic or superparamagnetic. The metal ion can be an ionic form of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. The metal ion can also be an ionic radionuclide of indium, gold, silver, mercury, technetium, rhenium and copper.

A radioactive medically useful metal ion may generate gamma rays, beta particles, or positrons which are converted into gamma rays upon collision with electrons. The medically useful metal ion may used in diagnostic imaging procedures including gamma scintigraphy, specific photon emission computerized tomography, or positron emission tomography. The medically useful metal ion may also be used diagnostically in magnetic resonance imaging. Medically useful metal ions may also be used therapeutically.

The type of medically useful metal ion depends on the specific medical application. Particularly useful metal ions include elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi.

The biological-function domain of the peptide is defined in the specification and claims as a sequence of one or more amino acids which constitute a biologically active peptide sequence, exhibiting binding to a biological receptor found on cells, tissues, organs and other biological materials. The biological-function domain also includes that sequence, which may be consecutive amino acids (sychnological) or may be non-consecutive amino acids (rhegnylogical), of one or more amino acids which forms a ligand, which ligand is capable of forming a specific interaction with its acceptor or receptor. The term "receptor" is intended to include both acceptors and receptors. The receptor may be a biological receptor. The peptide or the biological-function domain may optionally transmit a signal to the cells, tissues or other materials associated with the biological receptor after binding, but such is not required. Examples include, but are not limited to, biological-function domains specific for hormone receptors, neurotransmitter receptors, cell surface receptors, enzyme receptors and antibody-antigen systems. The biological-function domain may thus be either an agonist or antagonist, or a mixed agonist-antagonist. The biological-function domain also includes a ligand for site specific RNA or DNA binding, such as sequences which may be employed as mimics of transcription and other gene regulatory proteins. The biological-function domain also includes a sequence of one or more amino acids which exhibit binding to a biological receptor found on other peptides, on enzymes, antibodies, or other compositions, including proteinaceous compositions, which may themselves exhibit binding to another biological receptor.

Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, G A Grant, editor, W. H. Freeman & Co., New York, 1992, the teachings of which are incorporated herein by reference.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, G A Grant, editor, W. H. Freeman & Co., New York, 1992, the teachings of which are incorporated herein by reference, including the text, figures and tables set forth at pages 24–33, 39–41 and 58–67. A global structure refers to a peptide structure which exhibits a preference for adopting a conformationally constrained three-dimensional shape.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

Coordination of Metal Ions. The coordination sphere of various common metal ions, in general, is tetradentate to hexadentate. According to this invention a peptide is designed so that, in addition to the required chemical groups that are required for receptor recognition, it also contains the desired number (e.g., four to six in most cases) of groups for forming a bond with the metal ion. The molecule is designed so that, upon labeling with a metal ion, its conformation is fixed so that affinity for the receptor is achieved. The molecules are conveniently designed de novo by the help of three-dimensional molecular modeling computer software, such as the program called ALCHEMY-III (Tripos Associates Inc., St. Louis, Mo.). One basic approach to design is to construct a peptide backbone complexed to the metal ion so that all its valency is satisfied while preserving the coordination geometry defined by that particular metal ion. This gives rise to a molecular scaffold of a metal-peptide backbone, which is then decorated with functional groups that are specific for the biological target. In particular, the amino acid side chains required for receptor recognition and binding are assigned to appropriate amino acid residues on the scaffold in a manner such that the spatial relationship between these side chains matches that which has been reported or proposed previously in the scientific literature for that class of ligands, or as is found on in databases, such as the protein data bank maintained by Brookhaven National Laboratory. In general, it is now possible to determine the influence and relative importance of specific amino acid residues on receptor or antigen binding, using such tools as magnetic resonance spectroscopy and molecular modeling, allowing the specific design and synthesis of peptides which bind a known antigen, antibody or receptor, or which mimic a known binding sequence or ligand.

Figure 1B:
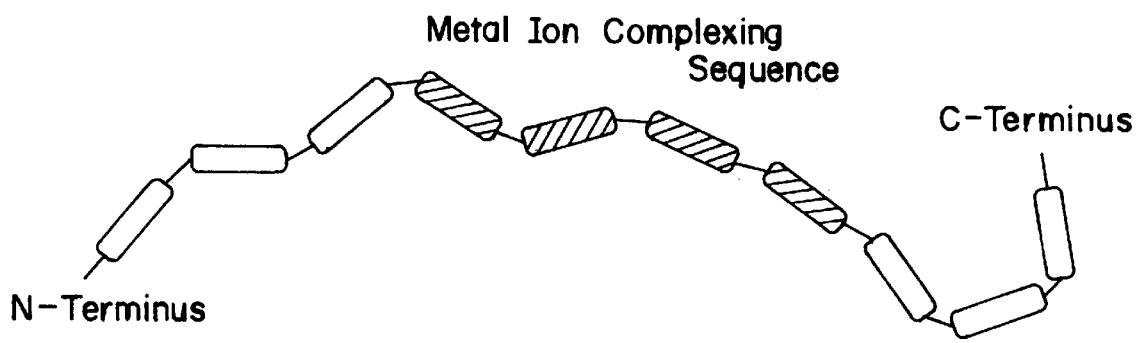
Figure 1C:
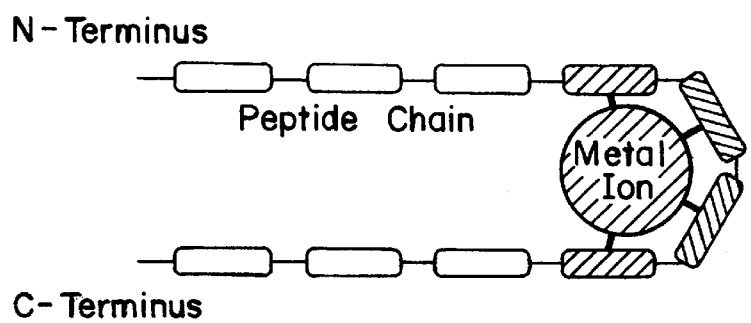

A metal ion with coordination number 4 to 6, and complexing respectively with a tetra, penta, or hexadentate ligand, will fold and constrain the ligand. A highly flexible molecule like a peptide, in other words, is folded to form a kind of reverse turn upon its complexation with a metal ion. This resulting turn is a highly constrained structure in the conformational sense. FIG. 1 schematically depicts a linear peptide made by this invention, both prior to complexing with a metal ion wherein it is not conformationally constrained, and after to complexing with a metal ion wherein it is conformationally constrained. FIG. 1-A depicts a naturally occurring reverse turn structure, such as a portion of a larger peptide or protein wherein the reverse turn is a stable structure located between two anti-parallel β-sheets. Thus in FIG. 1-A, additional amino acid sequences are joined to either terminus, but not included in the schematic depiction. FIG. 1-B schematically depicts a peptide of this invention, which is not complexed with a metal ion. Such a peptide is not structurally constrained, and thus each amino acid of the peptide has multiple, variable three-dimensional topology with respect to any other amino acid. FIG. 1-C depicts a peptide of this invention which is complexed with a metal ion. This complexation forms a reverse turn structure, yielding a highly constrained structure. The reverse turn is important to biological binding, since most biologically active peptides have been shown to display a folded structure or a reverse turn at the receptor binding site. Most peptide hormone receptors and antibody-binding epitopes have been shown to accept a folded conformer of a peptide. This invention can thus be applied to a wide variety of ligand systems, provided that the side chains forming the receptor contact are known and can be placed on a metal-peptide backbone scaffold resulting, after metal ion complexation, in the highly constrained topography required by the biological receptor.

Metal-Peptide Backbone. A variety of metal ion-complexing backbones may be utilized in this invention. The selection of backbone depends, in large part, on the biological receptor and the size and characteristics of the biological-function domain required for the biological receptor. The preferred metal-peptide backbone is based on the requisite number of particular coordinating groups required by the coordination sphere of a given complexing metal ion. In general, most of the metal ions that may prove useful in this invention have a coordination number of four to six, and rarely as high as eight, which implies that the putative metal ion-binding peptide chain must have sufficient groups placed in the peptide chain in a stereocompatible manner so as to establish bond with the metal ion of given geometry and coordination sphere. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however the linear construct is preferred. One example of a small linear peptide is Gly-Gly-Gly-Gly (SEQ. ID NO. 4) which has four nitrogens (a $N_4$ complexation system) in the back bone that can complex to a metal ion with a coordination number of four. Any similar suitable tetrapeptide could be employed; in addition, a tripeptide in which at least one of the amino acids has a side chain with a coordinating group can be employed with a metal ion with a coordination number of four. The side chain can have a nitrogen, oxygen or sulfur-based coordination group. Thus, a tetradendate peptide construct could be $N_4$, $N_3S$, $N_2S_2$, $NS_3$, $N_2SO$ or any similar combination yielding tetradendate coordination utilizing nitrogen, sulfur and oxygen atoms. Cyclic sequences may be employed; for example, cyclo[Gly-Gly-Gly-Gly] is a simple cyclic peptide which yields a $N_4$ tetradendate ligand suitable for complexing a metal ion with a coordination number of four. Other suitable modifications to this cyclic tetrapeptide template can be structurally engineered in a manner similar to that described above for a linear peptide to convert it to any of the other tetradendate ligand systems described above.

Both linear and cyclic systems can be further modified to incorporate additional coordinating groups so that the resulting peptide is penta- or hexa-dentate or higher to coordinate a metal ion with higher coordination numbers. The design of such metal ion-complexing peptide sequences has been described in the scientific literature (Ozeki E, Kimura S, and Imanishi Y, *Int. J. Peptide Protein Research* 34:111, 1989; and Garcia-Escheverria C, Albericio F, Giralt E and Pons M: *J. Amer. Chem. Soc.*, 115:11663–11670, 1992). Other examples of naturally occurring metal binding peptides include calmodulin and similar calcium binding peptides and valinomycin, a cyclic peptide antibiotic that binds potassium.

Other complexing backbones may include at least two amino acid residues and either a derivatized amino acid or a spacer sequence, which derivatized amino acid or a spacer sequence having a nitrogen, sulfur or oxygen atom available for complexing, with the valences of the metal ion. Examples of derivatized amino acids include amide, primary alkyl or aryl amide, 1,2,3,4-tetrahydroisoquinoline-2-carboxylic acid and its corresponding 7-hydroxy derivative, N-carboxymethylated amino acids, 2'-mercaptoTrp, $N^\beta$-(2 mercaptoethane)-$\alpha,\beta$-diaminopropionic acid and similar higher homologs of other homologous amino acids, $N^\beta$-(2 aminoethane)-$\alpha,\beta$-diaminopropionic acid and similar higher homologs of other homologous amino acids, $N^\beta$-(picolinoyl)-$\alpha,\beta$-diaminopropionic acid and similar higher homologs of other homologous amino acids, $\beta$-(picolylamide)-Asp and similar homologs of other homologous amino acids, $N^\beta$-(2-amino-benzoyl)-$\alpha,\beta$-diaminopropionic acid and similar higher homologs of other homologous amino acids, $\beta$-(2-amidomethylpyridine)-Asp and similar homologs of other homologous amino acids, N-benzyloxycarbonyl amino acid, N-tert. butyloxycarbonyl amino acid, N-fluorenylmethyloxycarbonyl amino acid and other similar urethane protected amino acid derivatives, and other derivatized or synthetic amino acids relating to any of the foregoing.

Examples of a spacer sequence which may be employed in this invention include 2-mercaptoethylamine, succinic acid, glutaric acid, 2-mercaptosuccinic acid, ethylenediamine, diethylenetriamnie, triethylenetetraamine, tetraethylenepentaamine, glycol, polyethyleneglycol, thioglycolic acid, mercaptopropionic acid, pyridine-2-carboxylate, picolylamine, 2-mercaptoaniline, 2-aminobenzoic acid, and 2-aminomethylpyridine. In general, any sequence which may be linked, directly or indirectly, to two amino acids so as to form a continuous sequence, and which has a nitrogen, sulfuir or oxygen atom available for complexing with the valences of the metal ion, may be employed.

For most applications, each peptide molecule will include a metal ion-complexing backbone which complexes a single metal ion. However, for certain applications, a peptide molecule may be designed with a metal ion-complexing backbone which will complex more than one metal ion. In one embodiment, the peptide sequence includes two discrete backbone segments, separated by one or more amino acid residues or other spacers, which residues or spacers may, but need not, form a part of the functional group or biological-function domain.

The metal ion-binding backbone is a peptide sequence that has a predefined stereochemistry at the chiral center, which in turn may be connected with additional residues and structural elements forming all or part of the biological-functional domain. Selection of a chiral center with pre-defined stereochemistry is of tremendous advantage in that it precludes the possibility of generating new chiral centers upon complexation of metal ion, that in turn may, and generally will, influence the biological activity profile of the biological-function domain. The generation of two new chiral centers, with no control on the resulting stereochemistries, is a major drawback of the heterodimeric rhenium and technetium complexes synthesized as mimetics of steroid hormone ligands by Katzenellenbogen and co-workers (Chi D Y, O'Neil J P, Anderson C J, Welch M J, and Katzenellenbogen J A: Homodimeric and heterodimeric bis(amino thiol) oxometal complexes with rhenium(V) and technetium(V): Control of heterodimeric complex formation and an approach to metal complexes that mimic steroid hormones. *J. Med. Chem.* 37:928–937, 1994).

Figure 2A:
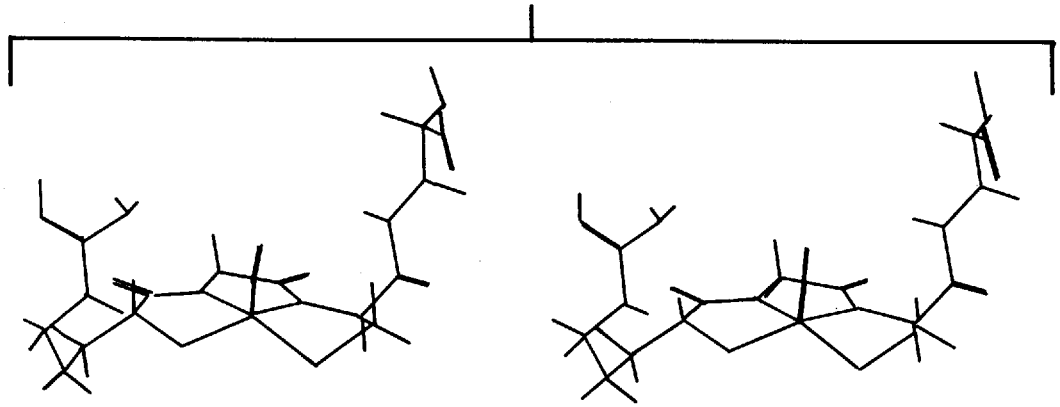
FIG. 2 shows a relaxed stereo view of a metal ion-labeled peptide of this invention with a primary unlabeled structure of D-Arg-Gly-D-Cys-β-Ala.
Figure 2B:
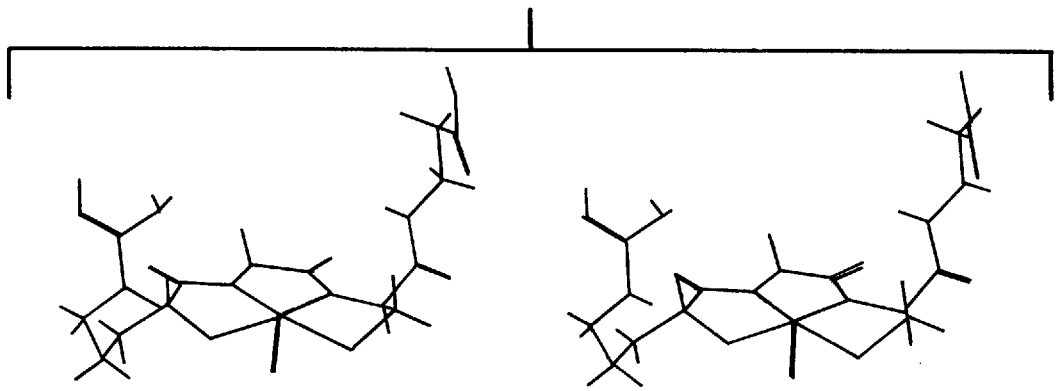
Figure 2C:
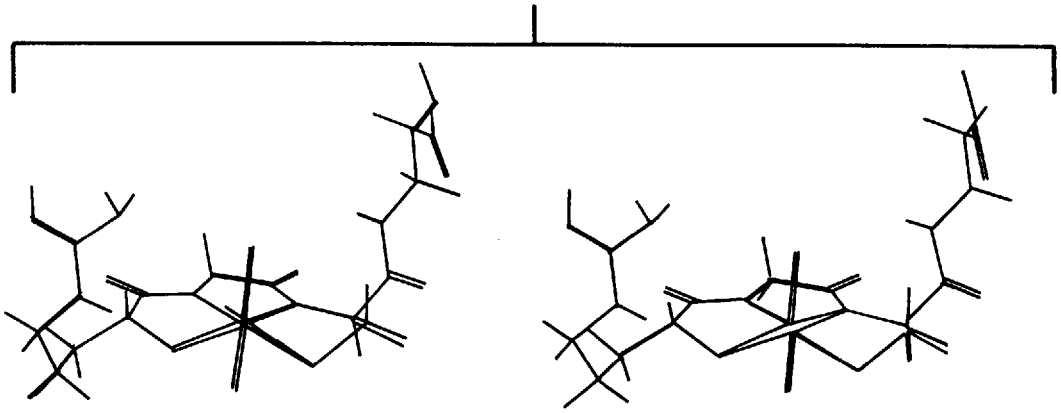

Complexation of a peptide to a metaloxo ion species, such as TcO[V] or ReO[V], can in theory lead to two isomers which differ in having either a syn- or anti-metal oxo group. The peptide-metaloxo complexes produced according to this invention may exhibit this type of syn- and anti-isomerism. These isomers are separable by HPLC and similar means in cases where an optically active amino acid also forms an integral part of the metaloxo ion complexing part of the molecule. The orientation of the metaloxo group in either syn- or the anti-configuration does not appear to have any effect on the conformational properties of the peptide backbone complexed to the metaloxo group, as is shown in FIGS. 2 and 3, which show the syn- and anti-configuration of a two different $^{99m}$Tc-labeled peptides of this invention. FIG. 2 shows a relaxed stereo view of a metal ion-labeled peptide with a primary unlabeled structure of D-Arg-Gly-D-Cys-β-Ala. FIGS. 2-A and 2-B show the two isomers created by the isomerism in the metal oxo group. FIG. 2-C shows the figures of FIGS. 2-A and 2-B superimposed, demonstrating that there is no difference in topography of the biologically relevant amino acid side chains between the two isomers. FIG. 3 shows a relaxed stereo view of a metal ion-labeled peptide with a primary unlabeled structure of Thr-D-Lys-Gly-D-Cys-Arg. FIGS. 3-A and 3-B show the two isomers created by the isomerism in the metal oxo group. FIG. 3-C shows the figures of FIGS. 3-A and 3-B superimposed, demonstrating that there is no difference in topography of the biologically relevant amino acid side chains between the two isomers. As a result, the biological activity of the two isomers is similar, unless the metal oxo group in one of the two isomers causes steric hindrance during interaction of the complex with the biological target. In these instances, one of the two isomers may have a higher biological activity profile.

Biological-function Domain. The biological-function domain of the constructs is a structural entity within the molecule that binds the biological target and may optionally either cause signal transduction or block the biological signal transduction. For peptides which can form a ligand and receptor pair, in which the receptor is not a biological target, the discussions pertaining to a biological-function domain apply unless expressly limited to biological systems. The biological-function domain of the peptide includes the various amino acid side chains, arranged so that the domain binds stereospecifically to the receptor and may optionally trigger or block a biological response. The biological-function domain may be either be sychnological (with structural elements placed in a continuous sequence) or rhegnylogical (with structural elements placed in a discontinuous sequence), as is described generally in Schwyzer R: Peptide-membrane interactions and a new principle in quantitative structure-activity relationships, *Biopolymers* 31:875–792, 1991, the teachings of which are incorporated herein by reference.

The design of a biological-function domain based upon a given complexing backbone for complexing metal ions may be carried out in at least two different ways. In one instance the metal ion-binding backbone and the biological-function domain are merged such that the biologically relevant functional groups are arranged directly on the metal binding domain, and the binding of the metal ion to the metal binding domain fixes the topography of the biological-function domain. Thus, the biological-function domain, upon fixing the conformation of the metal binding domain by binding of the metal ion, possesses relevant functional groups similar to the desired biologically active three-dimensional structure. Metal complexation by this approach therefore causes regional conformational changes that fix the topography of biologically relevant functional groups. This approach is well suited for, but not limited to, peptide ligands that fold as a reverse turn in their biologically active form. Examples of these ligands include opioid peptides, luteinizing hormone releasing hormone, somatostatin, melanotropin, tachykinins, and cholecystokinins, among many others.

In the other approach the biological-function domain is distinct from the metal binding backbone, and the complexation of the metal ion to the metal ion-binding backbone causes the peptide to have a conformationally constrained global secondary structure, resulting in topographic alignment of the biological-function domain in the desired biologically active three dimensional structure. This type of approach is well suited for, but not limited to, peptide ligands that incorporate a cyclic disulfide, lactam, lactone, thioether or similar bridge, and have a sychnological biological domain. It is also possible to incorporate both approaches in a given construct, so that all or a portion of the metal ion-binding backbone forms a part of the biological-function domain, with one or more distinct regions of the molecule forming the balance of the biological-function domain. In such cases, the biological-function domain may be either sychnological or may be rhegnylogical, but will most generally be rhegnylogical.

The biological potency, or affinity of the ligand for its receptor, of peptides of this invention is directly related to binding or complexation of a metal ion to the metal ion-binding backbone. The biological potency or affinity of peptides of this invention which are not bound or complexed with a metal ion is either negligible or significantly lower than that obtained with a metal ion complexed peptide. This feature is highly advantageous in case of constructs complexed with paramagnetic and radioactive metal ions, in that only the metal ion complexed molecules are biologically relevant; thus, if only 5% of the peptide molecules in a given preparation are metal ion complexed, then only that 5% will be biologically active. The remaining 95% of the peptide molecules, which are not metal ion complexed, will exhibit little or no biological activity. The metal ion labeled species is therefore essentially carrier-free, in that only peptide molecules carrying a metal ion are active. Thus, the entire mixture, include non-complexed peptide molecules, can be administered in vivo or used for in vitro assays without any requirement for purification to separate labeled molecules from unlabeled molecules. This presents significant advantages, in that the amount of biologically active peptide which is administered is substantially smaller than can be achieved by prior art methods. For example, in the case of a biologically active peptide which binds to a desired receptor but is toxic or has undesired biological activity, the toxicity or biological activity is minimized because only those peptide molecules which are labeled with a metal ion are biologically active. Those molecules which are not metal ion complexed, which in the case of radiopharmaceuticals will generally be a substantial majority of the total, will not be biologically active, and thus will not cause toxicity or undesired biological activity. Similarly, since only the peptides which are metal ion complexed are biologically active, the specific activity of the percentage of peptides which are metal ion complexed and hence biologically active is at or near the theoretical maximum possible.

Forming Complexes with Metal Ion. The complexation of the metal ions to the peptide, and specifically to the metal ion-complexing backbone of the peptide, is achieved by mixing appropriate amounts of the peptide with the metal ion. This is preferably done in solution, with the solution including an appropriate buffer. In one embodiment, the metal ion is, upon mixing with the peptide, in the oxidation state required for complexing to the metal ion-complexing backbone. Some metal ions are complexed in their most stable oxidation state, such as ionic forms of calcium, potassium, indium, manganese, copper, zinc, cobalt and other metals. In another embodiment, the metal ions must be reduced to a lower oxidation state in order to be complexed to the metal ion-complexing backbone. This is true of ferrous, ferric, stannous, stannic, technetiumoxo[V], pertechnetate, rheniumoxo[V], perrhenate and other similar metal ions. Thus, for example, both perrhenate and pertechnetate must be reduced to a lower oxidation state prior to complexing. Thus reduction may be performed prior to mixing with the peptide, simultaneous with mixing with the peptide, or subsequent to mixing with the peptide. Any means of reduction of metal ions to the desired oxidation state known to the art may be employed. For example, perrhenate or pertechnetate may be reduced by use of stannous ions, dithionite or other means. The stannous or dithionite metal ion reducing agent may be mixed with the metal ion to be reduced either prior or subsequent to addition of the metal ion to the peptide, or the reducing agent may be in solution with the peptide when the metal ion to be reduced, and subsequently complexed to the peptide, is added to the solution.

The stoichiometric ratios between the peptide and the metal ion in the labeling or complexing step can be varied depending on the application. For example, in the case of radiometal complexation, the ratio of radiometal ion to peptide molecule can be varied from at least 1:5 to 1:1000 or higher, without generating substantially radiochemical impurities. In other applications, the ratio of metal ion to peptide molecule can range from at least 1000:1 to 1:1000 or higher. When the concentration of metal ion is higher than the concentration of peptide molecule, all or virtually all of the peptide molecules will be complexed to a metal ion. The ratio of metal ion to peptide directly affects the percentage of peptides which will be conformationally constrained such that they have biological or other ligand activity, but otherwise there is no effect on receptor localization or targeting. For example, it is possible to complex metal ion to only 1% of the peptide molecules, by having a ratio of metal ion to peptide of 1:100, so that only 1% of the peptide molecules will have biological or other ligand activity.

Polymer Constructs. In order to alter the pharmacokinetic profile of the peptide-metal ion complexes of this invention, the complexes may be conjugated to various polymers, thereby altering the molecular size, charge, hydrophobicity and other characteristics of the molecule. Polymers which may be conjugated to peptide constructs include polyethylene glycol (PGA), polyvinyl alcohol (PVA), polyamino acids, fatty acids, lipid molecules and the like. The peptide-metal ion complexes may also be encapsulated into liposomes, thereby resulting in a marked difference in the pharmacokinetics and bioavailablity of the peptide-metal ion complexes within the liposomes.

Other Diagnostic Imaging Applications. The peptides and methods of this invention may also be applied to diagnostic agents for use in positron emission tomography (PET) and magnetic resonance imaging (MRI). For use as a PET agent a peptide is complexed with one of the various positron emitting metal ions, such as $^{51}$Mn, $^{52}$Fe, $^{60}$Cu, $^{68}$Ga, $^{72}$As, $^{94m}$Tc, or $^{110}$In. For MRI applications the complexing metal ion is paramagnetic, such as Mn, Gd, Fe, or Dy.

In both MRI and PET applications of the present invention only the fraction of the molecules that bind the relevant metal ion assume the receptor reactive three-dimensional structure, while the uncomplexed peptide molecule is devoid of or has limited biological potency. Thus the present invention affords an advantage in these diagnostic modalities in that the metal-labeled species can be administered without the need to separate the metal-labeled fraction from the un-complexed peptide molecules.

Use as Carrier of Therapeutic Agents. The products of this invention and the products made by the methods of this invention may also be used as vectors or carriers for target-specific delivery of other chemical species of therapeutic relevance, such as chemotherapy agents, gene regulation agents, enzyme function inhibition agents, target cell membrane disrupting agents, viral blocking agents, antibody blocking agents, and the like. The therapeutic payload can be conjugated to the peptide at sites other than those essential in either complexing the metal ion or binding the biological target. The therapeutic payload may be conjugate to the peptide either prior to or subsequent to complexing of the peptide to a metal ion, and thus activating the biological-function domain.

In Vivo Metal Ion Complexation. The peptide constructs of this invention may also be administered in vivo without complexation to a metal ion. Subsequent complexation of the peptide with a metal ion, which metal ion may be endogenous or may be separately administered, will cause the peptide to become conformationally constrained, thereby causing the biological-function domain to become specific for its target. Thus administration of a suitably designed peptide made by the methods of this invention, which complexes a metal ion present in the circulation, would convert the peptide into the biologically active form upon complexation with an endogenous or subsequently administered metal ion.

Radiopharmaceutical Applications. Products of this invention, and products made by the methods of this invention, may be employed as radiopharmaceutical agents. For example, when labeled with gamma emitting radioisotopes, such as $^{99m}$Tc, the products may be utilized for diagnostic nuclear medicine. Thus, the peptide of this invention includes a biological function-domain specific for a receptor which is characteristic of a particular disease state, or which is present on cells which are found in higher concentration at the sites of disease. For example, a peptide with a biological function-domain specific for platelets or fibrin or other blood clot components may be used for diagnostic imaging of thrombus. Similarly, a peptide with a biological function-domain specific for any of a number of white blood cells, including polymorphonuclear cells, may be used for diagnostic imaging of sites of infection or inflammation. The receptor may also be disease specific, such as tumor markers found in certain cancers.

Products of this invention, and products made by the methods of this invention, may also be used as therapeutic agents when labeled with alpha or beta emitting radioisotopes. For example, peptides labeled with alpha or beta emitting radioisotopes, such as Rhenium-186 ($^{186}$Re) or Rhenium-188 ($^{188}$Re), can be used for therapy of diseases, including specific cell surface receptor-associated diseases, such as various cancers.

The products of this invention, and products made by the methods of this invention, may be used for any radiopharmaceutical application for which a biologically active peptide or protein molecule may be employed. This includes, but is not limited to, products which are based on the binding site of antibody fragments, including F(ab')$_2$, Fab, Fv and Fc fragments of monoclonal antibodies, or otherwise based on the hypervariable region of monoclonal antibodies, including single-chain binding proteins. This also includes other antigen binding domain fragments and biologically active peptides. This allows the rational development of peptide-based imaging and therapeutic agents, by using the methods of this invention, to design and make a peptide, including a peptidomimetic or psuedopeptide, which upon labeling with a metal ion mimics the known binding characteristics of the parent molecule. Examples of suitable products which may be made by the methods of this invention include peptides which have biological-function domains, upon labeling with a metal ion, similar to those of somatostatin, RGD, YIGSR (SEQ. ID NO. 3), For-MLF, TGF-beta (tumor growth factor), FGF (fibroblast growth factor), PDGF (platelet-derived growth factor), EGF (epidermal growth factor), neuropeptide Y, cholecytokinin, tumor-related markers, hormones such as estrogen, tuftsin, melanotropin, somatostatin and the like. Over 300 receptors and their agonists are known, each of which is a potential candidate for a product of this invention.

For radiopharmaceutical applications, and other medical applications, the peptides of this invention, and products made by the methods of this invention, offer significant advantages over conventional linear or single-chain peptide constructs. For example, it is known that conformationally constrained and dimeric peptides derived from hypervariable loop sequences of antibodies can bind antigen with an affinity up to 40-fold higher than that obtained with linear sequence peptides. The peptides of this invention, in that they are by definition conformationally constrained upon labeling with a metal ion, have a similarly higher affinity than that obtained with conventional linear sequences.

For radiopharmaceutical applications, and other medical applications, the peptide may be delivered by any means known in the art. This includes intravenous injection, subcutaneous injection, administration through mucous membranes, oral administration, dermal administration, regional administration to an organ, cavity or region, and the like.

High Affinity Complexes. The products of this invention, and products made by the methods of this invention, exhibit extremely high affinity when labeled with a metal ion. This is particularly relevant for products which are small peptide constructs, on the order of three to about twenty amino acids. Prior art linear peptide sequences, which are not conformationally constrained, typically exhibit substantially lower affinity for their target than the parent molecule, such as an antibody hypervariable region, which is conformationally constrained. Thus, the products may be used directly as therapeutic agents, in which the metal ion serves to conformationally fix the biological function-domain, but in which the metal ion does not itself necessarily serve as a therapeutic component. For example, it is possible to design, using the methods of this invention, peptide-metal ion complexes that display biological activity profiles of a peptide hormone, neurotransmitter, steroid hormone, enzyme inhibitor and the like. The peptide-metal ion complexes of this invention bind biological receptors with high affinity in a stereospecific manner, thereby exerting a biological response as an agonist, antagonist or mixed agonist-antagonist. The peptide-metal ion complex can also be employed as a target-specific suicide substrate, by incorporating a reactive chemical group such as an isocyanate group, thiocyanate group, α-haloketone, mustard moiety or the like in the peptide so that after binding the target receptor or enzyme, the reactive group forms an irreversible bond with the target molecule rendering it ineffective to transduce further biological signals.

Use as Therapeutic Agent. The products of this invention, and products made by the methods of this invention, may be used, in general, for any application in which a peptide, including peptidomimetics or psuedopeptides, may be employed. The products are particularly useful for peptide drugs in which a conformationally constrained global structure, or a ligand or biological-function domain, is required. In these applications, the metal ion may serve only to conformationally constrain the peptide, or a portion thereof, or may itself be related to the therapeutic nature of the agent. Various peptide drug applications are disclosed elsewhere herein. In general, the products of this invention may find therapeutic uses similar to those of existing peptide- or peptidomimetic-based therapeutics, including (a) hormones such as: oxytocin, vasopressin, somatostatin, melanotropins, leutinizing hormone releasing hormone, insulin calcitonin, steroid hormones, etc.; (b) enzyme inhibitors such as: renin and angiotensin converting enzyme inhibitors, HIV protease, etc.; (c) antibiotics such as: valinomycin, penicillin, tetracycline, bleomycin, etc.; (d) ion channel blockers; (e) analgesics; (f) growth factors and many others. The development of peptide-based pharmaceuticals is described generally in Ward D J, Ed.: *Peptide Pharmaceuticals: Approaches to the Design of Novel Drugs*, Ward D J, editor, Open University Press, London, 1989, incorporated herein by reference.

Industrial and other Non-Pharmaceutical Applications. Peptides made by the methods of this invention, may be employed for a wide variety of industrial, agricultural and other non-medical applications. The peptides and methods of this invention apply to any use of peptides, including peptidomimetics and other peptide variants as disclosed herein, wherein it is desired that the peptide have a well-defined secondary structure. This necessarily includes peptides which bind to a particular recognition area or other actual or functional equivalent of a biological-function domain, such as peptides which form a specific interaction between a ligand and its acceptor. This method is particularly useful for small peptides, composed of less than about 20 amino acids, which it is desired will be conformationally constrained. Peptides of this invention may be used in any commercial or industrial process or application in which conformationally constrained peptides are desired or may be used. This includes such applications as waste remediation, catalytic peptides, enzymatic peptides, markers and detection systems, pesticides, animal drugs and vaccines, and the like. Peptides of this invention used in a commercial or industrial process or application may serve as carriers for any agent or reagent which may be conjugated or otherwise bound to a peptide, or may be designed so that the peptide has intrinsic biochemical properties, such as a catalytic or enzymatic peptide. Such peptides may also serve as blocking agents, which are designed to bind to a particular receptor, but which do not otherwise transmit any signal or participate in any biochemical reaction. In most applications, the metal ion will only serve to conformationally fix the peptide, and will not itself contribute to the effect of the peptide. However, possible applications include those in which the metal ion is an intrinsic part of a detection system, or in which the metal ion itself has some further effect. This includes, but is not limited to, use of metal ion peptides in which the metal ion is radioactive for commercial or industrial processes or applications.

General design considerations for two peptide constructs are given below. These design considerations, and modifications thereof, may be employed in any case in which a biological function-domain, or ligand structure, is known.

Platelet Fibrinonectin Receptor Construct. A peptide was constructed based upon an analogue to the tripeptide sequence Arg-Gly-Asp (RGD). The receptor for this peptide includes the integrin heterodimeric glycoproteins IIb/IIIa (GP IIb/IIIa), a transmembrane protein found on the surface of platelets. This heterodimeric complex changes conformation in response to platelet-stimulating agents, including peptides containing the RGD sequence. Many naturally occurring peptides of different origin, such as echistatin from snake venom and others, contain the RGD sequence as a common motif for binding to the GP IIb/IIIa receptor.

Binding of fibrinogen through RGD motif causes activation of the platelets. Mimics of RGD sequence that can block fibrinogen binding to the GP IIb/IIIa receptor, thereby inhibiting platelet aggregation, are being pursued as therapeutic modalities for myocardial infarction. In addition, radiolabeled forms of these agents show promise as in vivo imaging agents for various forms of thrombus.

To construct a peptide using the method of this invention, a peptide molecular construct to bind technetium (or rhenium) metal ion, with the ability after binding the metal ion to bind a platelet fibrinonectin receptor, was designed so that the four available valences of the core of reduced technetium (or rhenium) oxide [V] were coordinated to a suitable peptide sequence that is capable of complexing the metal. A tripeptide sequence providing a $N_3S_1$ metal ion-complexing backbone, which specifically binds technetium metal ion, was utilized as the starting material. To mimic the biological binding of the RGD sequence, it was determined that the two most important and primary structural aspects required for making receptor contact to the GP IIb/IIIa complex are a positively charged side chain and a negatively charged side chain analogous to the side chains of Arg and Asp residues in a typical fibrinonectin peptides containing the receptor active sequence Arg-Gly-Asp (RGD sequence). Decorating the metal-peptide scaffold with these two side chains gave the RGD mimic tetrapeptide Arg-Gly-Cys-β-Ala as a putative candidate for platelet fibrinonectin receptor. Further refinements in the structure were made in response to other considerations, including stereochemistry of the side chains of the optically active amino acids, higher in vivo stability of the resulting peptide, higher blood residence time in vivo, and the ease of complexing with the metal ion in the desired configuration. Based on these considerations, a peptide of the following general formula was designed:

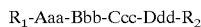

$R_1$-Aaa-Bbb-Ccc-Ddd-$R_2$

Where: Aaa=An amino acid with a positively charged side chain, and containing a N which can be available for binding a metal ion, such as Arg, D-Arg, N-Me-Arg, D-N-Me-Arg, N-alkylated or arylated Arg, S-(2-aminoethyl)Cys, O-(2-aminoethyl)-Ser and similar derivatives and isomers of Lys, Orn, homoArg, and other similar basic amino acids.

Bbb=An amino acid with an un-charged side chain, and containing a N which can be available for binding a metal ion, such as L- or D-isomers of Gly, Ala, Aib, Val, Nle, Leu and similar amino acids with uncharged side chains.

Ccc=L- Cys, D- Cys, L- HomoCys, D- HomoCys, L- Pen, D- Pen and other synthetic or derivatized amino acids containing a S, and preferably a S and a N, which can be available for binding a metal ion.

Ddd=An amino acid with a negatively charged side chain, such as L- or D-isomers of β-Ala, N-Me-β-Ala, higher homologues of β-Ala, Asp, N-Me-Asp, Glu, N-Me-Glu, and other synthetic or derivatized amino acids thereof, or an uncharged amino acid such as Gly or Ala.

$R_1$=H, Alkyl, aryl, alkylcarbonyl, arylcarbonyl, alkyloxycarbonyl, aryloxycarbonyl, or a polymer such as PEG, PVA, or polyamino acid attached directly or through a carbonyl group.

$R_2$=If Ddd is other than Gly, Ala, β-Ala, N-Me-β-Ala, or a higher homologue of β-Ala, then $R_2$ is an amide or substituted amide.

Representative peptides from this series include D-Arg-Gly-D-Cys-β-Ala and PEG-CO-D-Arg-Gly-D-Cys-β-Ala. These peptides display very high affinity ($K_D$=5–10 nM) for the GP IIb/IIIa platelet receptor in a clot binding assay after their binding to reduced Tc=O [V]. Peptides not complexed to the metal ion are either inactive or have very weak activity ($K_D$=>1 mM).

The structure of the D-Arg-Gly-D-Cys-β-Ala peptide, after binding to technetium, is as follows:

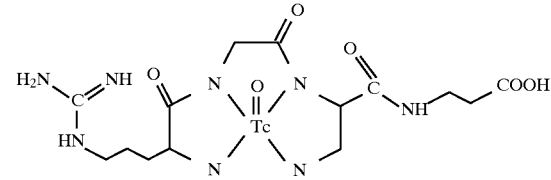

FIG. 2 shows the predicted three-dimensional backbone of the entire peptide, in a relaxed stereo view, after binding of the peptide to technetium. FIGS. 2-A and 2-B are two isomers created by the isomerism of the metal oxo group, while FIG. 2-C shows FIGS. 2-A and 2-B superimposed, demonstrating the topographic homology of biologically relevant amino acid side chains in the two isomers.

Tuftsin Receptor Peptide Construct. A peptide-metal complex for the Tuftsin receptor found on polymorphonuclear (PMN) granulocytes, monocytes and macrophages was designed using a similar route and approach. Native tuftsin is a tetrapeptide of the sequence Thr-Lys-Pro-Arg (SEQ. ID NO. 5), located as residues 289–292 of the Fc region of the heavy chain of leukokinin (a cytophilic γ-globulin). It is liberated by a combination of two cleavages. The C-terminal peptide bond is cleaved in the spleen by splenic enzyme and subsequent cleavage of the N-terminal peptide bond by enzyme leukokininase which occurs on the membranes of the granulocytes where it acts to stimulate phagocytosis. The tuftsin sequence stimulates macrophages and polymorphonuclear granulocytes towards phagocytosis. This sequence thus has a role in the immune system response for fighting infections and bacteria and other invasions. There are specific tuftsin receptors present on granulocytes and macrophages. The receptor density is approximately 50,000–100,000 per cell, with the receptor-tuftsin complex reported to internalize after binding. Thus a peptide specific for the tuftsin receptor may be used in the treatment of certain diseases, as is disclosed generally in U.S. Pat. Nos. 4,390,528 to V A Najjar and 5,028,593 to K Nishioka, the teachings of which are incorporated herein by reference. Such a peptide may also be radiolabeled with a diagnostic metal ion, such as $^{99m}$Tc, and used to determine sites of concentration of granulocytes and macrophages, such as infections and inflammations, or radiolabeled with a therapeutic metal ion, such as $^{186}$Re or $^{188}$Re, and used in the treatment of disease.

A precursor peptide of the following structure was designed, incorporating both a metal ion-binding backbone, and a biological-function domain, which biological-function domain is biologically active only upon labeling or complexing the metal ion-binding backbone with a metal ion:

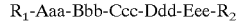

$R_1$-Aaa-Bbb-Ccc-Ddd-Eee-$R_2$

Where: Aaa=Thr, Cys, Pen, or Ser and corresponding des-amino derivatives. Both L- and D-amino acids can be substituted at this position.

Bbb=An amino acid with a positively charged side chain, and containing a N which can be available for binding a metal ion, including L- and D-isomers of Arg, Lys, Orn, homoArg, S-(2-aminoethyl)Cys, O-(2-aminoethyl)Ser and other similar basic amino acids, and derivatives thereof.

Ccc=An amino acid with an un-charged side chain, and containing a N which can be available for binding a metal ion, such as L- or D-isomers of Gly, Ala, Aib, Val, Nle, Leu and similar amino acids with uncharged side chains.

Ddd=L- Cys, D- Cys, L- HomoCys, D- HomoCys, L- Pen, D- Pen and other synthetic or derivatized amino acids containing a S, and preferably a S and a N, which can be available for binding a metal ion.

Eee=An amino acid with a positively charged side chain, such as L- or D-isomers of Arg, Lys, Orn, homoArg, S-(2-aminoethyl)Cys, O-(2-aminoethyl)Ser and other similar basic amino acids, and their corresponding des-carboxyl derivatives. A similar aliphatic or aromatic chain with a basic functional group can also be substituted.

$R_1$=H, Alkyl, aryl, alkylcarbonyl, arylcarbonyl, alkyloxycarbonyl, aryloxycarbonyl, or a polymer such as PEG, PVA, or polyamino acid, attached directly or through a carbonyl group. $R_1$ does not exist if Aaa is a des-amino amino acid.

$R_2$=Amide, substituted amide, ester, or a polymer such as PEG, PVA, or polyamino acid. $R_2$ does not exist if Eee is a des-carboxyl amino acid.

A representative peptide from this series includes Thr-D-Lys-Gly-D-Cys-Arg. This peptide displays very high affinity ($K_D$=~1–5 nM) for human leukocytes after its binding to reduced TcO[V]. This peptide, when complexed to radioactive $^{99m}$TcO[V], localizes to the site of inflammation or infection upon i.v. administration. The affinity of the peptide which is not complexed to a metal ion is on the order of $K_D$=~$10^{-4}$M.

The structure of the Thr-D-Lys-Gly-D-Cys-Arg peptide after binding to technetium is as follows:

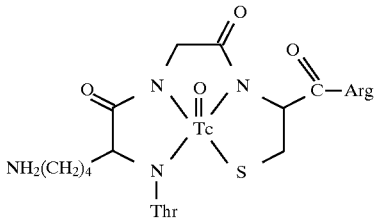

FIG. 3 shows the predicted three-dimensional backbone of the entire peptide, in a relaxed stereo view, after binding of the peptide to technetium. FIGS. 3-A and 3-B are two isomers created by the isomerism of the metal oxo group, while FIG. 3-C shows FIGS. 3-A and 3-B superimposed, demonstrating the topographic homology of biologically relevant amino acid side chains in the two isomers.

Formulation of Radiopharmaceutical Kits. One application of this invention is to provide peptides for use as radiopharmaceuticals, either diagnostic agents labeled with radioisotopes such as $^{99m}$Tc $^{111}$In, or therapeutic agents labeled with radioisotopes such as $^{188}$Re or $^{186}$Re. $^{99m}$Tc is generally obtained as sodium pertechnetate, and rhenium as perrhenate. In both instances, it is necessary to reduce the pertechnetate or perrhenate to a lower oxidation state so that the metal ion complexes with the peptide. Stannous (also referred to herein as "Sn (II)") may be effectively used for this purpose. Sources of Sn (II) include stannous tartrate, stannous glucoheptonate, stannous gluconate, stannous phosphonate, stannous chloride, stannous sulfate, stannous acetate, and stannous fluoride. The selection of the source of Sn (II) and its final concentration depends on the intended medical application of the peptide, the nature of the peptide, and the metal ion to be used. For example, a significantly higher stannous concentration is required to reduce perrhenate than to reduce pertechnetate. $^{188}$Re in the form of perrhenate may be labeled using kits with between about 2.5 to 15 mM stannous, with total tin correspondingly ranging from about 1 to 5 mg or higher if a larger volume kit is employed, all at a pH of between about 5 and 6. Generally speaking, lower stannous concentration kits require heating, such as for 30 to 60 minutes in a boiling bath, to effectively reduce all the available perrhenate, while high total tin kits have sufficient reduction capacity to reduce the perrhenate within about one hour when incubated at room temperature. Increasing the stannous concentration above about 15 mM has negligible effects on reduction capacity, and at higher concentrations it becomes increasingly difficult to keep the stannous in solution.

For either $^{186}$Re or $^{188}$Re labeling, approximately 5 mM of stannous tartrate, for a total tin concentration of approximately 1.2 mg, was employed with 200 μg of peptide. For labeling the same quantity of peptide with $^{99m}$Tc, approximately 0.5 mM of stannous tartrate was employed. The amount of Sn (II) in the preparation must be such as to be sufficient to completely reduce the metal ion to the desired redox state under the specified reaction conditions, without having such Sn (II) concentrations that the tin precipitates from the solution. Precipitation can be, in large part, controlled by the selection of appropriate buffers and complexing agents. The quantity of Sn (II) also varies with the reaction conditions; for example, with preparations which are incubated at temperatures in the range of 80° C. to 100° C., less Sn (II) is required than if incubation is effected at room temperature. The incubation time also varies depending on the incubation conditions, principally temperature, although pH and other conditions also affect incubation time. Generally speaking, incubation at temperatures in the range of 80° C. to 100° C. are substantially shorter than incubations at room temperature, requiring an incubation period from one-half to one-tenth or less in length.

For labeling with pertechnetate, it is possible to use between 0.2 and 1 mM of stannous, and preferably from 0.5 to 1 mM stannous, with total tin as low as 40 μg, depending upon the fill volume.

Regardless of the method employed, the form of stannous employed depends in part on the buffers utilized in the kits. For examples, in kits with buffers containing tartrate as a complexing agent, use of stannous tartrate salt is desirable. For kits containing complexing agents other than tartrate, such as kits containing EDTA, stannous chloride dihydrate may be employed. Generally speaking, all stannous is added in concentrated hydrochloric acid. This favors maintaining the tin in the Sn (II) oxidation state, as stannous ions, rather than the Sn (IV) state, as stannic ions. Sn (II) effectively reduces radiometals such as pertechnetate or perrhenate, while Sn (IV) does not. Complexing agents are generally used in a 2 to 20 molar excess over the total tin, to insure that all of the tin, including both stannous ion and any stannic ion, will be complexed. Uncomplexed tin at neutral pH readily forms an insoluble hydroxide. In the absence of complexing agents, above pH 5.5 colloidal tin species may be formed before the hydroxide precipitates. Complexing agents sequester tin from the hydrolysis reaction, but do not prevent tin from entering into redox reactions. pH titrations of stannous solutions have shown increasing complexing ability with EDTA>>citrate>>glucoheptonate>> tartrate>>malic acid. Though stannous tartrate exists as a 1:1 molar ratio of tin:tartrate as the dry salt, empirical evidence suggests that a minimum 2-fold excess of tartrate is necessary to stabilize stannous at neutral pH. However, EDTA, citrate and glucoheptonate can all stabilize stannous at approximately 1:1 molar ratios at neutral pH; a working formula of 1.2:1 molar ratio of complexing agent:stannous can be satisfactorily utilized.

Regardless of the method employed, high concentrations of tin may be stabilized through the use of appropriate buffers. For example, metal binding buffers, such as diglycine and triglycine at 50 to 100 mM, can increase the stability of high millimolar tin concentrations at neutral pH. For example, a buffer containing 50 mM diglycine or triglycine, with an appropriate complexing agent such as EDTA, citrate, glucoheptonate or tartrate, can be used to stabilize the tin, and prevent precipitation, when the total tin concentration is in the range of 5 to 10 mM. Suitable metal ion buffers include citrate and tartrate, polyaminocarboxcylic acids such as EDTA, DTPA and NTA (nitrilotriacetic acid), ACES (N-2-acetamido-2-aminoethanesulfonic acid, ADA (N-2-acetamidoiminodiacetic acid), bicine, tricine, glycylglycine, triglycine, tetraglycine, and MES (2-(N-morpholino)ethanesulfonic acid). For example, it is possible to stabilize a high millimolar stannous solution, comprising 5 mM stannous tartrate in 40 mM KH Phthalate and 10 mM NaK tartrate, at neutral pH and above by addition of a second metal binding buffer, such as glycylglycine, which has a pKa of 8.2, at concentrations from 50 to 100 mM. Generally speaking, the solubility of stannous is enhanced by addition of a second metal binding buffer which has a pKa at or close to the pH of the composition to be radiolabeled. For example, if a radiolabeling composition contains tartrate, which has a pKa of 4.3, and if the composition is to be radiolabeled at a pH significantly different from 4.3, then increased tin complexation, with resultant stability of the tin and protection from precipitation, can be achieved by addition of a second metal binding buffer with a pKa at or near the pH of the composition to be radiolabeled.

Depending on the peptide employed, formulation and reaction conditions must be altered, and can be determined empirically for any given peptide of this invention. For example, complexing or buffering agents will yield different results with different peptides. Thus, one peptide construct may be used with $SnCl_2$-tartrate-phthalate, at a ratio of 1-10-40 mM at pH 5.5, in a vial containing 5 µg of peptide in a fill volume of 400 µL, yielding good results when labeled with $^{99m}Tc$ as sodium pertechnetate. Another peptide may have radiochemical impurities, or not label completely, using this reducing and buffering solution, but may yield good results with $SnCl_2$-succinate-EDTA, at a ratio of 1-20-1.2 mM at pH 6.2, in a vial containing 5 µg of peptide in a fill volume of 400 µL. Other reducing and buffering solutions may similarly be employed, and determined for each particular peptide.

In a given case, the tartrate concentration can range from below 10 mM to over 50 mM. The buffer, such as potassium hydrogen phthalate, can range from over 40 mM to less then 10 mM. Potassium hydrogen phthalate at a lower 10 mM concentration is sufficient to yield acceptable radiolabeling results while affording a higher glass transition temperature for facile freeze drying.

A variety of excipients and other agents may be employed as needed. This include agents to increase solubility of certain peptides, lyophilization excipients, and the like. Maltose, inositol, manitol, and other sugars can be added as a freeze drying excipient.

In general, quantities as low as 1–5 µg of peptide of this invention may be labeled with $^{99m}Tc$ or rhenium using the methods described above. Since only radiolabeled peptide is biologically active, the amount required is, in part, dependent on the quantity of metal ions to be added. For most radiopharmaceutical applications, the peptide should be in a 5- to 20-fold excess over the quantity of metal ions, to insure that all metal ions are incorporated into a peptide molecule. However, for non-radiopharmaceutical applications, the metal ion can be in significant excess over the quantity of peptide, to insure that all peptide molecules have incorporated a metal ion. For such non-radiopharmaceuticals applications, the quantity of peptide labeled with metal ion may be as large as is desired.

Most prior art radiopharmaceutical methods involve peptide formulations of 100 µg and higher. The methods of this invention can be used in radiopharmaceutical preparations in formulations containing 5 µg or less, and in which the biologically active portion, based on the percentage of total peptide complexed with a metal ion, is from less than 1% to approximately 20% of the total peptide in the formulation. Thus, the amount of total peptide used in a formulation is very low, and the amount of biologically peptide in the formulation upon labeling with a metal ion is even lower still, by from roughly 5- to 100-fold or less. Use of very small amounts of peptide minimizes dimerization and other aggregation of the peptide; results in very high specific activity, at or near theoretical limits, and provides for much lower toxicity or undesired biological activity, by minimizing the amount of biologically active peptide in the formulation.

The products of this invention are conveniently radiolabeled by adding the radionuclide to a vial containing the peptide, Sn (II), buffers and other excipients. After addition of the radionuclide the solution is allowed to incubate for a period of from 15 min. to 4 hr., and at a temperature ranging from room temperature to 100° C. After radiolabeling, the product may be tested by HPLC, including reversed phase HPLC with a UV and radioisotope detector in series, thin layer chromatography or other means known in the art. The products of this invention will typically have less than 5% radiochemical impurities, and frequently less than 2% radiochemical impurities, the impurities consisting of uncomplexed or unreduced radionuclide, colloids and the like.

The invention is further illustrated by the following non-limiting examples.

EXAMPLE 1—DESIGN AND SYNTHESIS OF RGD RECEPTOR-SPECIFIC PEPTIDE

A molecule based on the receptor binding characteristics of Arg-Gly-Asp (RGD) was designed. Based on a peptide $N_3S_1$ metal ion-binding backbone, and modifying and decorating the backbone to arrive at a construct similar to the receptor binding region of RGD, the peptide D-Arg-Gly-D-Cys-β-Ala was designed, and was synthesized by conventional solid phase peptide synthesis. In brief, Fmoc-β-Ala was coupled to 4-alkoxybenzyl alcohol resin, a peptide synthesis resin. After the removal of the Fmoc group by treatment with piperidine, the peptide chain was elongated successively using Fmoc-D-Cys(Trt), Fmoc-Gly, and Fmoc-D-Arg(Pmc). The Fmoc group from the resulting peptide-resin, Fmoc-D-Arg(Pmc)-Gly-D-Cys(Trt)-β-Ala-Resin, was removed. Fully unprotected peptide was released from the resin by treatment with TFA. The peptide was purified by reversed phase HPLC and obtained as a lyophilized white powder. Fast atom mass spectrometric analysis gave the correct mass for the synthesized peptide.

EXAMPLE 2—ALTERNATE SYNTHESIS METHOD OF RGD RECEPTOR-SPECIFIC PEPTIDE

The peptide D-Arg-Gly-D-Cys-β-Ala is synthesized by alternate solid phase methods using Boc protected amino acids. In this approach, Boc-β-Ala is first coupled to Merrifield resin or PAM-resin. The Boc group is then removed by treatment with TFA and the peptide chain elongated using successive amino acids, Boc-D-Cys(MeBzl), Boc-Gly, and Boc-D-Arg(Tos). The fully synthesized protected peptide-resin, Boc-D-Arg(Tos)-Gly-D-Cys(MeBzl)-β-Ala-Resin, is then treated with HF to liberate the fully unprotected peptide. The peptide is then purified by reversed phase HPLC.

EXAMPLE 3—ALTERNATE SYNTHESIS METHOD OF RGD RECEPTOR-SPECIFIC PEPTIDE

The peptide D-Arg-Gly-D-Cys-β-Ala is also synthesized by conventional methods of solution-phase peptide synthesis. In brief, Boc-D-Cys(MeBzl) is coupled to β-Ala-OEt using a coupling agent such as DCC-HOBt. The Boc group is cleaved by treatment of the resulting dipeptide Boc-D-Cys(MeBzl)-β-Ala-OEt with TFA. It is then coupled to Boc-Gly using a similar approach. After the removal of the Boc group from the resulting tripeptide Boc-Gly-D-Cys(MeBzl)-β-Ala-OEt and subsequent coupling with Boc-D-Arg(Tos), a fully protected tetrapeptide is obtained. The C-terminal ester group is saponified and the resulting peptide treated with HF to result in fully unprotected peptide which is purified by reversed phase HPLC.

EXAMPLE 4—PREPARATION OF D-Arg-Gly-D-Cys-β-Ala CONJUGATED TO HIGHER MOLECULAR WEIGHT MOLECULES

The D-Arg-Gly-D-Cys-β-Ala peptide of Example 1 was conjugated to various forms of polyethylene glycol (PEG) to obtain higher molecular weight constructs for biodistribution studies. PEG of various molecular weights (100–8000) and mono-methoxy PEG of similar molecular weights was activated with disuccinimide carbonate according to the teachings of S. Zalipsky (*Bioconjugate Chemistry* 4:296–299, 1993). The activated PEG was then treated with the peptide D-Arg-Gly-D-Cys-β-Ala taken in phosphate buffer (125 mM, pH 6.5) in presence of 1 mM HOBt. After 1 hr. at room temperature, the reaction mixture was extracted several times with dichloromethane. The combined organic extract was washed once with water and evaporated to dryness. The product was then precipitated by the addition of anhydrous ether. The product was purified once by precipitation from an ethanol-ether system. The following constructs were synthesized in this manner: [$PEG_{8000(M/W)}$]-(D-Arg-Gly-D-Cys-β-Ala)$_2$, [Me-$PEG_{5000(M/W)}$]-D-Arg-Gly-D-Cys-β-Ala, and [Me-$PEG_{2000(M/W)}$]-D-Arg-Gly-D-Cys-β-Ala.

EXAMPLE 5—RADIOLABELING AND FORMULATION OF RADIOPHARMACEUTICAL KITS USING D-Arg-Gly-D-Cys-β-Ala AND STANNOUS-TARTRATE-PHTHALATE

Direct Labeling. The D-Arg-Gly-D-Cys-β-Ala peptide obtained as set forth in Example 1 was labeled with $^{99m}$Tc in the presence of stannous as a reducing agent in a tartrate-phthalate buffer. 100 μg of the peptide was mixed with generator eluted $^{99m}$Tc-sodium pertechnetate (1–35 mCi of radioactivity in up to 500 μL volume). To this was added a nitrogen purged solution (400 μL) of stannous-tartrate-phthalate (1 mM-10 mM-40 mM, pH 6.1). The head space of the vial was purged with nitrogen and the solution left at room temperature for 30 min. A small aliquot of this $^{99m}$Tc labeled peptide was analyzed by reversed phase HPLC on a C-18 column (VYDAC, Cat. No. 218TP104). A gradient of 0–20% acetonitrile completed in 30 min. at a flow rate of 1.5 mL/min was employed. The radioelution profile was generated by a radio-detection flow cell system attached to the HPLC. The profile indicated that the $^{99m}$Tc-labeled peptide eluted at 11.1 min. A small amount of radiolabeled fraction was also present that eluted at 13.8 min which might be a dimeric species composed of 2:1 peptide- $^{99m}$Tc complex. The profile also indicated that the detectable amount of reduced $^{99m}$Tc that elutes with the solvent peak (retention time 2.2 min.), if any, was no more than 4%. A 10 μCi sample of the labeled preparation was spotted on an instant thin layer chromatography (ITLC) strip (1.5×10 cm. silica gel impregnated strips, Gelman Science, Ann Arbor, Mich.) and developed with 150 mM NaCl. Radioactivity measurements on this strip revealed that the origin had only 2–4.5% of radioactivity, which corresponds to the amount of $^{99m}$Tc colloid present in the preparation. The labeled preparation, when stored at room temperature for up to 36 hrs., did not show any change in its HPLC and ITLC profiles. The HPLC and ITLC results together suggest a very good $^{99m}$Tc labeling profile for this peptide.

Kit Formulation. A radiopharmaceutical kit was formulated using the same buffer system. Each vial contained 100 μg of the D-Arg-Gly-D-Cys-β-Ala peptide of Example 1 and a nitrogen purged solution (200–400 μL) of stannous-tartrate-phthalate (1 mM-10 mM-40 mM, pH 6.1). The kits were stored under refrigeration, and some kits were lyophilized. The lyophilized vials were backfilled with nitrogen and sealed. To label either the refrigerated vials or the lyophilized vials, the contents of the vial were mixed with generator eluted $^{99m}$Tc-sodium pertechnetate (1–35 mCi of radioactivity in up to 500 μL volume), and the solution was left at room temperature for 30 min. Substantially similar radiochemical yields and profiles were obtained with these kits.

Kits were formulated with as little as 5 μg of the D-Arg-Gly-D-Cys-β-Ala peptide of Example 1 and a nitrogen purged solution (200–400 μL) of stannous-tartrate-phthalate (1 mM-10 mM-40 mM, pH 6.1). Kits with 5 μg of D-Arg-Gly-D-Cys-β-Ala were labeled with 2 mCi of $^{99m}$Tc and the equivalent of 50 mCi of $^{99m}$Tc as $^{99}$Tc, for a metal ion concentration equivalent to 52 mCi of $^{99m}$Tc, with no significant radiochemical impurities. The ratio of metal ion to peptide was 1:22 with 52 mCi equivalent of $^{99m}$Tc. By increasing the quantity of $^{99}$Tc, successful labeling was achieved at as low as a 1:8 metal ion to peptide ratio using 5 μg kits.

PEG Conjugated Product Labeling. The products of Example 4 were directly labeled by the method described above, with similar radiochemical yields and profiles obtained. The elution times necessarily varied depending on the form of PEG employed as a conjugate.

Alternate Synthesis Peptide. The method of radiolabeling is independent of the origin of the peptide, and may be employed as described above with peptides made using the methods of any of Examples 2 or 3.

EXAMPLE 6—RADIOLABELING AND FORMULATION OF RADIOPHARMACEUTICAL KITS USING D-Arg-Gly-D-Cys-β-Ala AND STANNOUS-TARTRATE-PHTHALATE-GLYCYLGLYCINE

Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in a tartrate-phthalate-glycylglycine buffer. The general methodology was similar to that of Example 5 except that a nitrogen purged solution (200–400 μL) of stannous-tartrate-phthalate-glycylglycine (1 mM-10 mM-40 mM-50 mM, pH 6.6) was used. Labeling efficiency results similar to those in Example 5 were obtained using the same HPLC and ITLC techniques.

Kit Formulation. A radiopharmaceutical kit is formulated using the same buffer system. Each vial contains from 1 to 100 μg of the D-Arg-Gly-D-Cys-β-Ala peptide of Example 1 and a nitrogen purged solution (200–400 μL) of stannous-tartrate-phthalate-glycylglycine as set forth above. For some kits, excipients are added, including maltose, manitol, and other sugars. The kits are stored under refrigeration, or are optionally lyophilized. The lyophilized vials are backfilled with nitrogen and sealed. To label either the refrigerated vials or the lyophilized vials, the contents of the vial are mixed with generator eluted $^{99m}$Tc-sodium pertechnetate (1–35 mCi of radioactivity in up to 500 μl volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 7—RADIOLABELING AND FORMULATION OF RADIOPHARMACEUTICAL KITS USING D-Arg-Gly-D-Cys-β-Ala AND STANNOUS-TARTRATE-SUCCINATE

Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in a tartrate-succinate buffer. The general methodology was similar to that of Example 5 except that a nitrogen purged solution (200–400 μL) of stannous-tartrate-succinate (1 mM-10 mM-20 mM, pH 6.2) was used. Labeling efficiency results similar to those in Example 5 were obtained using the same HPLC and ITLC techniques.

Kit Formulation. A radiopharmaceutical kit is formulated using the same buffer system. Each vial contains from 1 to 100 μg of the D-Arg-Gly-D-Cys-β-Ala peptide of Example 1 and a nitrogen purged solution (200–400 μL) of stannous-tartrate-succinate as set forth above. The kits may be lyophilized, with the lyophilized vials backfilled with nitrogen and sealed. To label, the contents of the vial are mixed with generator eluted $^{99m}$Tc-sodium pertechnetate (1–35 mCi of radioactivity in up to 500 μL volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 8—RADIOLABELING AND FORMULATION OF RADIOPHARMACEUTICAL KITS USING D-Arg-Gly-D-Cys-β-Ala AND STANNOUS-EDTA-SUCCINATE

Direct Labeling. The D-Arg-Gly-D-Cys-β-Ala peptide obtained as set forth in Example 1 was labeled using stannous as a reducing agent for $^{99m}$Tc-sodium pertechnetate, with the stannous stabilized in an EDTA-succinate buffer. The general methodology was similar to that of Example 5 except that a nitrogen purged solution (200–400 μL) of stannous-EDTA-succinate (1 mM-1.1 mM-20 mM, pH 6.2) was used. Labeling efficiency results similar to those in Example 5 were obtained using the same HPLC and ITLC techniques.

Kit Formulation. A radiopharmaceutical kit is formulated using the same buffer system. Each vial contains 1 to 100 μg of the D-Arg-Gly-D-Cys-β-Ala peptide of Example 1 and a nitrogen purged solution (200–400 μL) of stannous-EDTA-succinate as set forth above. Excipients may be added, and the kits lyophilized and backfilled with nitrogen and sealed. To label, the contents of the vial are mixed with generator eluted $^{99m}$Tc-sodium pertechnetate (1–35 mCi of radioactivity in up to 500 μL volume).

PEG Conjugated Product Labeling. The products of Example 4 are directly labeled by the methods described in this Example.

Alternate Synthesis Peptide. The method of radiolabeling of this Example is independent of the origin of the peptide, and may be employed as described above with peptides made using the methods of any of Examples 2 or 3.

EXAMPLE 9—RADIOLABELING AND FORMULATION OF RADIOPHARMACEUTICAL KITS USING D-Arg-Gly-D-Cys-β-Ala AND GLUCOHEPTONATE

The D-Arg-Gly-D-Cys-β-Ala peptide obtained as set forth in Example 1 was labeled using stannous as a reducing agent for $^{99m}$Tc-sodium pertechnetate, with the stannous stabilized in glucoheptonate, which also served as a transchelation agent. To label, a solution of the peptide (100 μg in 100 μL saline) was added to a GlucoScan (DuPont, Wilmington, Del.) kit freshly reconstituted with 1–35 mCi of $^{99m}$Tc-sodium pertechnetate (200–500 μL) for 10 min. at room temperature. The reaction mixture was allowed to stand at room temperature and was then analyzed by HPLC and ITLC techniques as described in Example 5. Labeling efficiency results similar to those in Example 5 were obtained using the same HPLC and ITLC techniques.

EXAMPLE 10—RADIOLABELING AND FORMULATION OF RADIOPHARMACEUTICAL KITS USING D-Arg-Gly-D-Cys-β-Ala AND STANNOUS-BORATE-TARTRATE

The D-Arg-Gly-D-Cys-β-Ala peptide obtained as set forth in Example 1 was labeled using stannous as a reducing agent for $^{99m}$Tc-sodium pertechnetate, with the stannous stabilized in borate-tartrate buffer. The general methodology was similar to that of Example 5 except that a nitrogen purged solution (200–400 μL) of stannous-borate-tartrate (1 mM-50 mM-20 mM, pH 9.3) was used. Labeling efficiency results similar to those in Example 5 were obtained using the same HPLC and ITLC techniques.

EXAMPLE 11—STABILITY OF RADIOPHARMACEUTICAL KITS USING D-Arg-Gly-D-Cys-β-Ala IN PLASMA

100 μL of $^{99m}$Tc-labeled D-Arg-Gly-D-Cys-β-Ala peptide labeled with 1 mCi of $^{99m}$Tc and prepared according to Example 5 was mixed with an equal volume of platelet poor plasma (PPP). This was then incubated for one hour at 37°

C. An aliquot of this mixture was then analyzed by HPLC under the same conditions described in Example 5. A comparison of the generated profile with that of sample not incubated with PPP revealed no difference in the two HPLC profiles. This thus indicates the high stability of the labeled peptide in plasma.

EXAMPLE 12—SATURATION BINDING OF $^{99m}$Tc-D-Arg-Gly-D-Cys-β-Ala TO PLATELETS

Saturation binding of $^{99m}$Tc-labeled D-Arg-Gly-D-Cys-β-Ala peptide to human platelets was demonstrated using a freshly prepared preparation of platelet rich plasma (PRP). The concentration of platelets in PRP was adjusted using PPP to a final value of $3 \times 10^8$ platelets/mL per each assay tube. Increasing amounts of $^{99m}$Tc-labeled peptide was added to constant amounts of PRP taken in different assay tubes. This was followed by the addition of ADP to a final concentration of 10 μM in order to activate the platelets. Similar volumes of PPP were used at each concentration of the $^{99m}$Tc-labeled peptide as a measure of the non-specific binding component under the experimental conditions. Binding was allowed to take place for 30 min. after which the tubes were transferred to an ice bath. A 200 μL aliquot corresponding to $0.6 \times 10^8$ platelets was filtered through a glass fiber filter that was presoaked in PPP for 30 min. The filters were then washed three times with 1 mL of PBS and counted in a gamma counter for the bound radioactivity. The data was normalized to account for the decay of $^{99m}$Tc and plotted. An analysis of the data gave a value for $K_D$ in the range of 5–10 nM for the $^{99m}$Tc-labeled D-Arg-Gly-D-Cys-β-Ala peptide.

EXAMPLE 13—SATURATION BINDING OF $^{99m}$Tc-D-Arg-Gly-D-Cys-β-Ala TO FIXED PLATELETS

Figure 4:
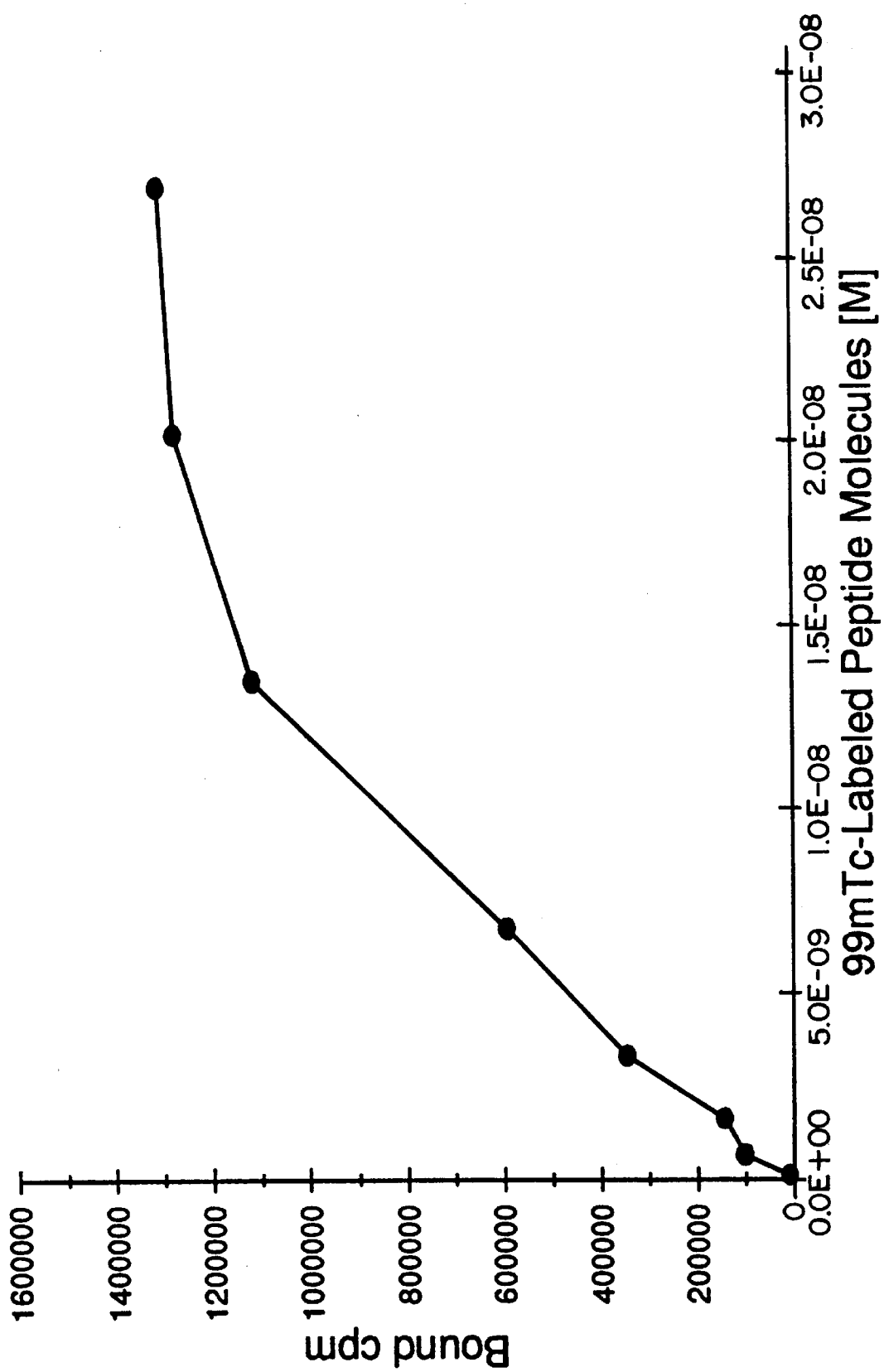
FIG. 4 shows saturation binding isotherm of binding of with $^{99m}$Tc-labeled D-Arg-Gly-D-Cys-β-Ala with human activated platelets.

Saturation binding of $^{99m}$Tc-labeled D-Arg-Gly-D-Cys-β-Ala peptide to ADP activated and formalin fixed human platelets was demonstrated using a preparation of platelet rich plasma (PRP) that was prepared according to the teachings of U.S. Pat. No. 5,332,726, incorporated herein by reference, except that ADP (10 μM final concentration) was used instead of thrombin to activate the platelets. The concentration of fixed platelets obtained in this manner was adjusted using PPP to a final value of $3 \times 10^8$ platelets/mL per each assay tube. Increasing amounts of $^{99m}$Tc-labeled peptide was added to these constant amounts of fixed platelets taken in different assay tubes. Similar volumes of PPP were used in respect to each concentration of the $^{99m}$Tc-labeled peptide as a measure of the non-specific binding component under the experimental conditions. The binding was allowed to take place for 30 min. and the assay subjected to the protocol as described in Example 12. The data obtained in this case was also normalized to account for the decay of $^{99m}$Tc and plotted. The results demonstrate saturation binding kinetics of the peptide for its activated platelet receptor as is shown in FIG. 4. The X-axis shows the actual fraction of $^{99m}$Tc-labeled molecules of the total peptide molecules, with only the $^{99m}$Tc-labeled molecules presumed to have biological activity. An analysis of the data gave a value for $K_D$ in the range of 5–10 nM for the $^{99m}$mTc-labeled D-Arg-Gly-D-Cys-β-Ala peptide, comparable to the results obtained in Example 12.

EXAMPLE 14—SATURATION BINDING OF $^{99m}$Tc-D-Arg-Gly-D-Cys-β-Ala TO CLOTS

Saturation binding of $^{99m}$Tc-labeled D-Arg-Gly-D-Cys-β-Ala peptide of Example 5 to blood clots was demonstrated using freshly prepared human blood clots. 100 μL aliquots of the freshly drawn human blood were placed in glass tubes and let to stand at room temperature for 1.5 hrs. After further 30 min. incubation at 4° C. the clots formed were washed three times with 1 mL of 1 mM EDTA in PBS. Increasing amounts of $^{99m}$Tc-labeled peptide was added to these clots in triplicates. Empty glass tubes were included in the assay as a measure of non-specific binding component under the experimental conditions. The binding was allowed to take place for 60 min. at room temperature. All the tubes were then transferred to an ice bath. 1 mL of ice cold PBS was added to each tube and the clots washed by aspirating off the PBS. The clots were further washed three more times with 1 mL of PBS in a similar manner and the tubes containing the clots counted for bound radioactivity in a gamma counter. The data obtained in this manner were normalized to account for the decay of $^{99m}$Tc and plotted. The results presented in two FIGURES below reveal saturation binding kinetics of the peptide for its activated platelet receptor on the platelets embedded in the clots. An analysis of the data gave a value for $K_D$ in the range of 5–10 nM for for the $^{99m}$Tc-labeled D-Arg-Gly-D-Cys-β-Ala peptide, comparable to the results obtained in Examples 12 and 13.

EXAMPLE 15—SATURATION BINDING OF $^{99m}$Tc-D-Arg-Gly-D-Cys-β-Ala TO CLOTS USING CARRIER FREE PREPARATION

Saturation binding of a carrier free preparation of $^{99m}$Tc-labeled D-Arg-Gly-D-Cys-β-Ala peptide to blood clots was demonstrated, using the methods of Example 14. The carrier free preparation of the $^{99m}$Tc-labeled peptide was prepared by passing a freshly labeled preparation of $^{99m}$Tc-labeled peptide of Example 5 through an affinity column composed of a solid phase (agarose or polystyrene beads) to which a thiol reacting group has been attached. Maleimide bound to polystyrene and bromoacetylated dextrose resins used for this purpose were obtained from commercial sources. These functionalities of the resin are reactive towards the thiol groups of the Cys residue in the peptide. As a consequence, the molecules of the peptide that were not bound to $^{99m}$Tc atom were irreversibly retained on the column. The effluent from the column therefore contained the pure $^{99m}$Tc-labeled molecules of the peptide. This preparation was used in a clot binding experiment as described in Example 14. An analysis of the data yielded a value for $K_D$ in the range of 5–10 nM. These results were very much comparable with those obtained in Examples 12 through 14, confirming that it was the $^{99m}$Tc-labeled fraction of the peptide that was biologically active, and exhibited receptor binding.

EXAMPLE 16—SATURATION BINDING OF PEG-$^{99m}$Tc-D-Arg-Gly-D-Cys-β-Ala TO CLOTS

Saturation binding of $^{99m}$Tc-labeled PEG$_{8000}$-D-Arg-Gly-D-Cys-β-Ala peptide of Example 4 to blood clots was demonstrated using freshly prepared human blood clots in a manner similar to that described in Example 14. The PEG-conjugated peptide was labeled with $^{99m}$Tc according to the methods described in Examples 4 and 5. The results gave a value for $K_D$ in the range of 5–20 nM for $^{99m}$Tc-labeled PEG$_{8000}$-D-Arg-Gly-D-Cys-β-Ala peptide, comparable to the results obtained in Examples 12–15.

EXAMPLE 17—COMPETITION OF COLD $^{99}$Tc-D-Arg-Gly-D-Cys-β-Ala WITH $^{99m}$Tc-D-Arg-Gly-D-Cys-β-Ala IN BINDING ASSAYS

Figure 5:
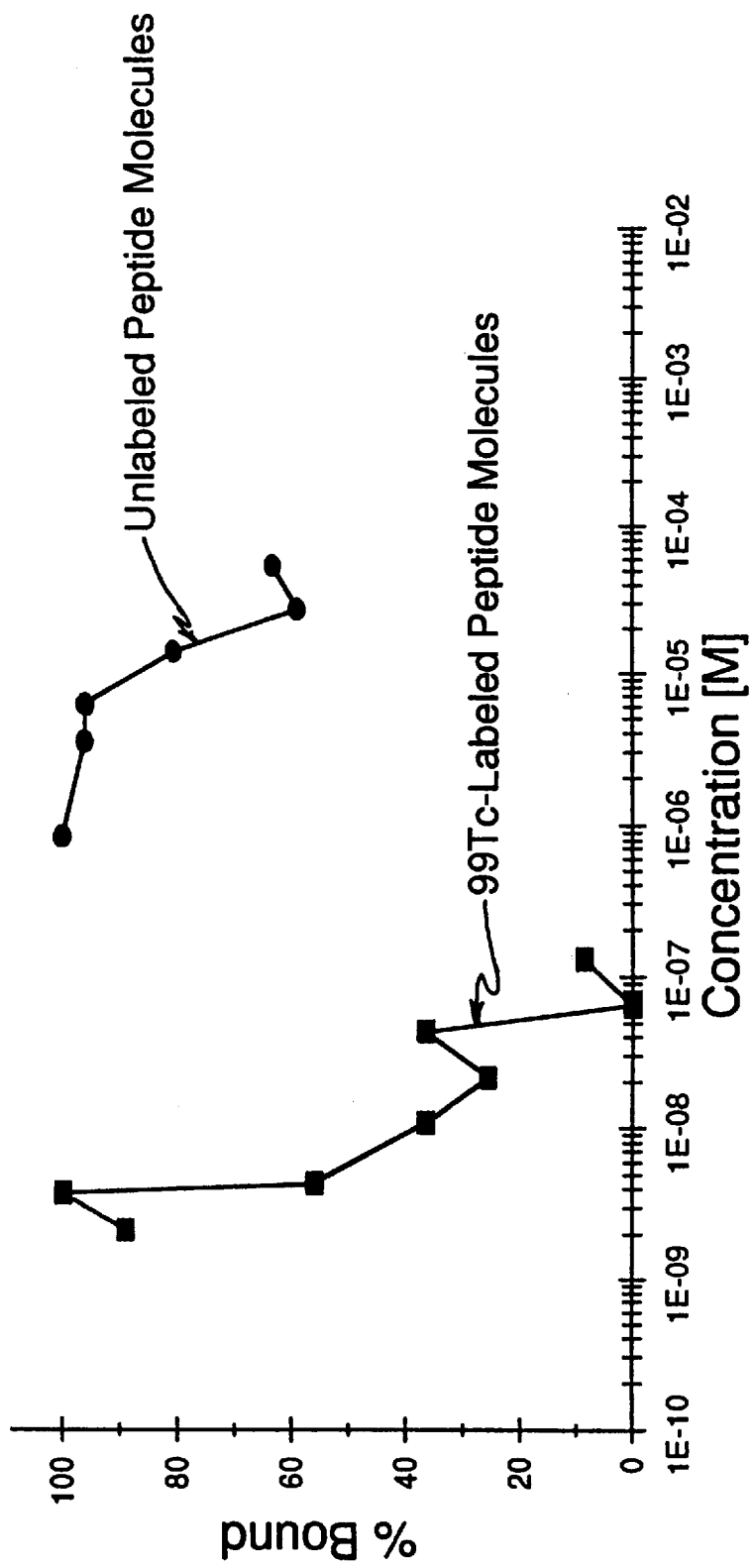
FIG. 5 shows results of competition binding of $^{99}$Tc-labeled D-Arg-Gly-D-Cys-β-Ala and unlabeled D-Arg-Gly-D-Cys-β-Ala with $^{99m}$Tc-labeled D-Arg-Gly-D-Cys-β-Ala for binding to human platelets.

Activated and formalin fixed platelets ($3 \times 10^8$ platelets/mL per assay tube), as described in Example 13, were incubated with a mixture of $^{99m}$Tc-labeled D-Arg-Gly-D-Cys-β-Ala and $^{99}$Tc-labeled D-Arg-Gly-D-Cys-β-Ala peptide. A constant but tracer amount of the $^{99m}$Tc-labeled peptide was used in this assay. The amount of $^{99}$Tc-labeled peptide, however, varied between $10^{-9}$M to $10^{-7}$M in terms of the $^{99}$Tc-labeled fraction of the total peptide molecules. Both the $^{99m}$Tc-labeled and the $^{99}$Tc-labeled peptides were prepared according to the methods of Example 5. This data demonstrates binding inhibition with the $^{99}$Tc-labeled peptide, and yields a $K_D$ in the range of 5–10 nM for the $^{99m}$Tc-peptide. FIG. 5 depicts the binding curve obtained in this experiment for $^{99}$Tc-labeled peptide.

EXAMPLE 18—COMPETITION OF D-Arg-Gly-D-Cys-β-Ala WITH $^{99m}$Tc-D-Arg-Gly-D-Cys-β-Ala IN BINDING ASSAYS

This study was conducted as set forth in Example 17, except that D-Arg-Gly-D-Cys-β-Ala peptide was employed instead of $^{99}$Tc-D-Arg-Gly-D-Cys-β-Ala. The amount of the unlabeled peptide varied between $10^{-6}$M to $10^{-4}$M. The data from this assay showed that the unlabeled peptide has substantially lower affinity, in the range of $K_D > 10^{-4}$M, in competing with the $^{99m}$Tc-labeled peptide for the receptor site. FIG. 5 depicts the binding curve obtained in this experiment for unlabeled peptide, together with the binding curve for $^{99}$Tc-labeled peptide.

EXAMPLE 19—COMPETITION OF Sn-D-Arg-Gly-D-Cys-β-Ala WITH $^{99m}$Tc-D-Arg-Gly-D-Cys-β-Ala IN BINDING ASSAYS

This study was conducted as set forth in Example 17, with D-Arg-Gly-D-Cys-β-Ala incubated in a buffer containing stannous ions (the same buffer used for $^{99m}$Tc-labeling of the peptide). The amount of presumptively Sn-labeled peptide varied between $10^{-6}$M to $10^{-4}$M. The data showed that the Sn-labeled peptide has substantially lower affinity in competing with the $^{99m}$Tc-labeled peptide for the receptor site. The presence of stannous does not interfere with the affinity of the peptide for its platelet receptors.

Figure 6:
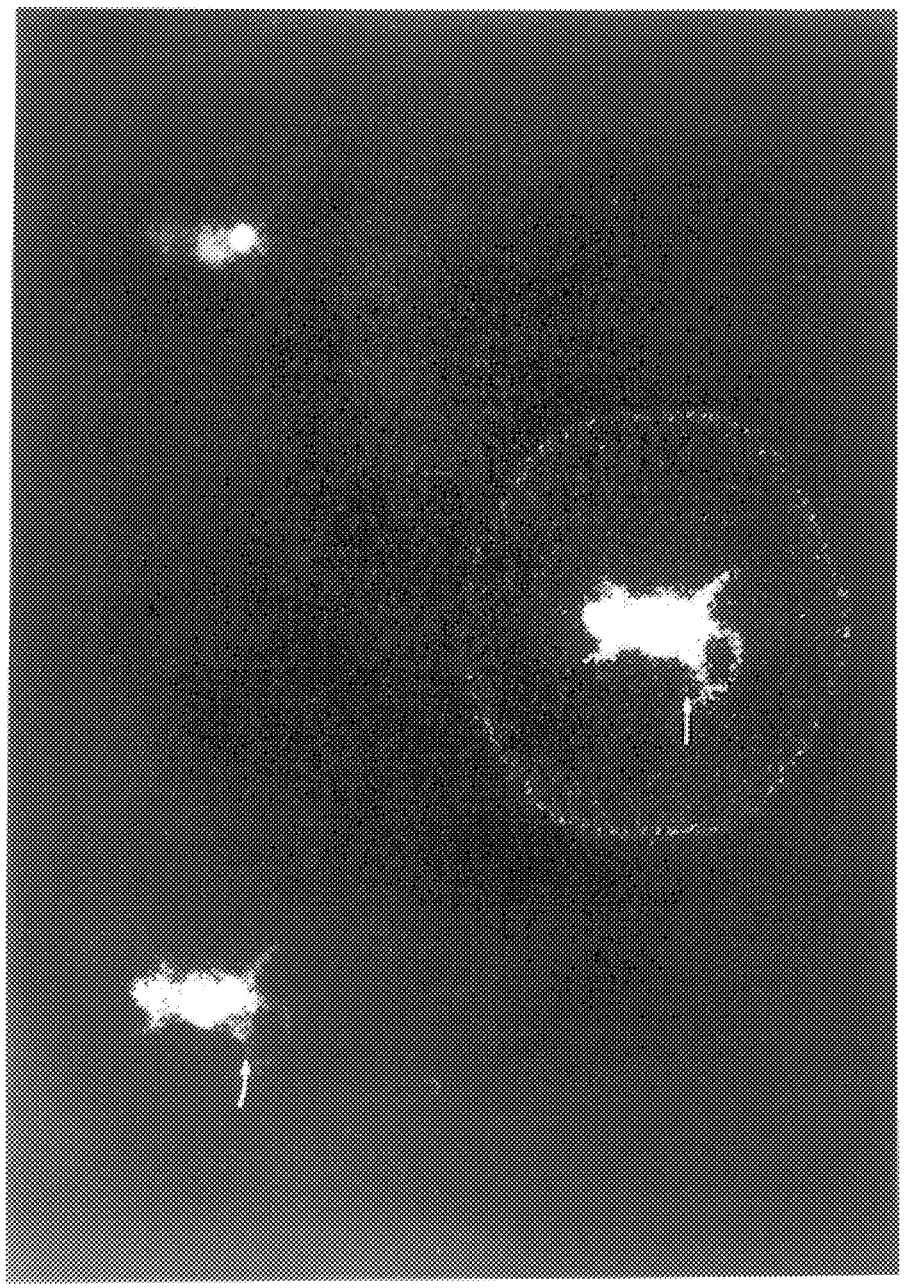
FIG. 6 shows a gamma camera image of an induced clot in a leg in an animal model using $^{99m}$Tc-labeled D-Arg-Gly-D-Cys-β-Ala.

EXAMPLE 20—IMAGING OF CLOT IN LEG USING $^{99m}$Tc-D-Arg-Gly-D-Cys-β-Ala 100 to 200 μL of a saline solution of thrombin (10–20 units) was injected intramuscularly in the upper thigh region of mice. This was done to induce formation of blood clots at the site of injection. 5–30 min. after injection of thrombin 50–200 μCi of $^{99m}$Tc-labeled D-Arg-Gly-D-Cys-β-Ala peptide prepared according to the Example 5 was injected in the animal through the tail vein. Gamma camera images were taken immediately thereafter by placing the animal on a parallel collimator attached to the camera. During the course of imaging the animal was subdued by intraperitoneal injections of ketamine. The site of clot inducement in the leg could be visualized as a result of the accumulation and localization of the $^{99m}$Tc-labeled peptide. Continual imaging was possible up to 45–60 min. post injection of the peptide or until the clot was cleared by the animal's body defense mechanisms. FIG. 6 shows a gamma camera image of a mouse obtained at 25 minutes after injection of the $^{99m}$Tc-labeled peptide, which was 38 minutes after injection of 100 μL of thrombin injected into the leg of the animal.

EXAMPLE 21—IMAGING OF LUNG CLOT USING $^{99m}$Tc-D-Arg-Gly-D-Cys-β-Ala

Figure 7:
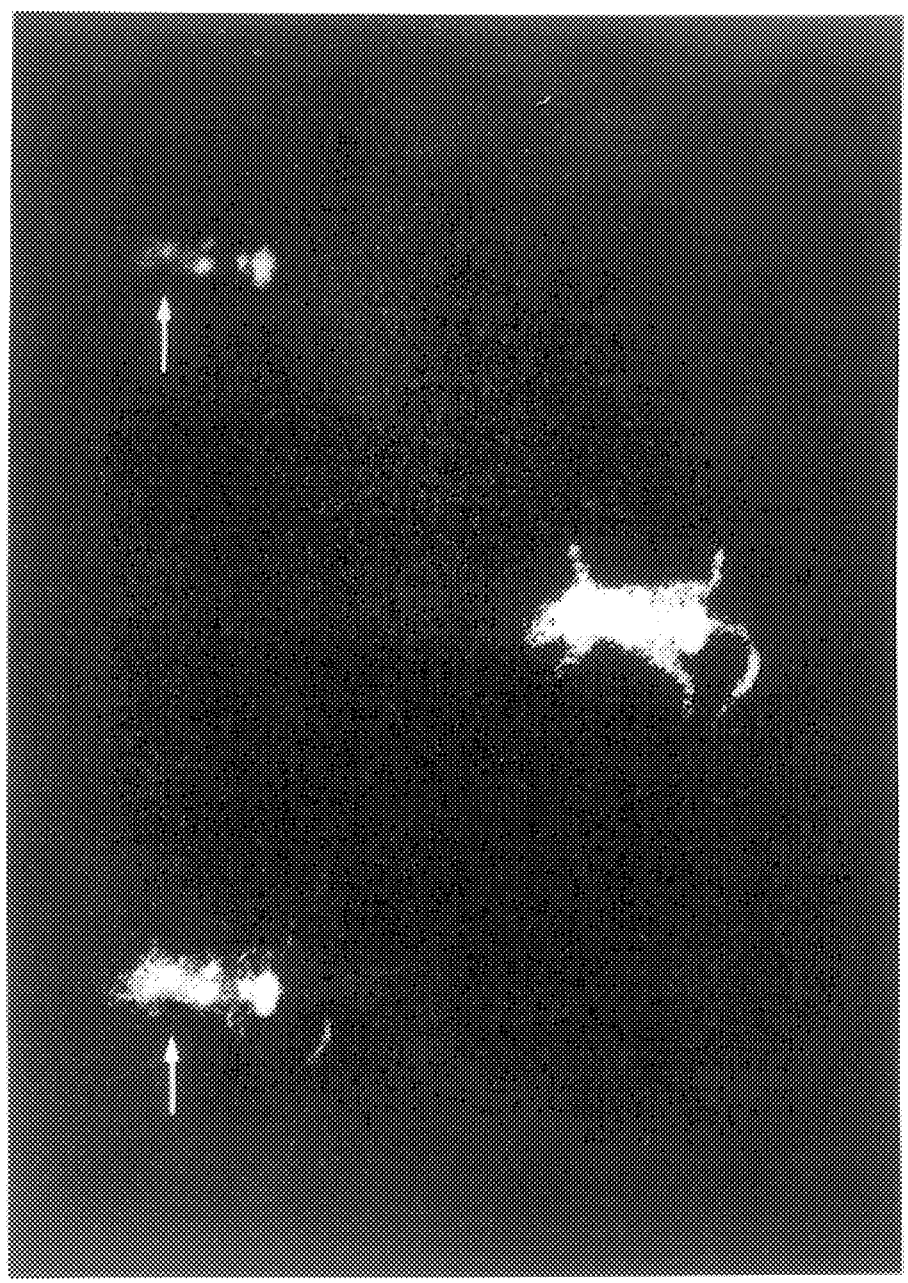
FIG. 7 shows a gamma camera image of an induced lung clot in an animal model using $^{99m}$Tc-labeled D-Arg-Gly-D-Cys-β-Ala.

300 μL of saline reconstituted thrombin (30 units) was incubated with about 100 million polyvinyl fluoridine beads (5 micron average size) for 1 hr. The beads were then recovered by centrifugation and resuspended in 300 μL of fresh saline. 100 to 200 μL of this suspension, or 100–200 μL of the original saline solution of thrombin (10–20 units), was injected in a rat through its tail vein. This process causes blood clotting, with the clots getting trapped in the lung. These pulmonary emboli were then imaged with tail-vein injected $^{99m}$Tc-labeled D-Arg-Gly-D-Cys-β-Ala prepared by the method of Example 5, injected within 5–30 min. of administration of thrombin. Gamma camera images were taken immediately thereafter by placing the animal on a parallel collimator attached to the gamma camera. During the course of imaging the animal was subdued by intraperitoneal injections of ketamine. The pulmonary emboli induced in this manner could be visualized as a result of the accumulation and localization of the $^{99m}$Tc-labeled peptide. Continual imaging was possible up to 45–60 min. post injection of the peptide, or until the clot was cleared by the animal. FIG. 7 shows the gamma camera image of a pulmonary embolism obtained at 7 minutes after injection of the $^{99m}$Tc-labeled peptide, which was 34 minutes after injection of 200 μL of thrombin-coated beads.

EXAMPLE 22—DESIGN AND SYNTHESIS OF TUFTSIN ANALOGUE

A molecule based on the receptor binding characteristics of tuftsin was designed. Using an amino acid $N_3S_1$ metal ion-binding backbone, and modifying and decorating the backbone to arrive at a construct similar to the receptor binding region of tuftsin, the sequence Thr-D-Lys-Gly-D-Cys-Arg was designed so that the peptide would bind tuftsin receptor on granulocytes after labeling with $^{99m}$Tc, or another suitable metal ion. The peptide was made by solid-phase peptide synthesis, using methods similar to the method of Example 1. In brief, Fmoc-Arg(Pmc) was coupled to 4-alkoxybenzyl alcohol resin, a peptide synthesis resin. After the removal of the Fmoc group by treatment with piperidine, the peptide chain elongated successively using Fmoc-D-Cys(Trt), Fmoc-Gly, Fmoc-D-Lys(Boc), and Fmoc-Thr(Bu$^t$). Fmoc group from the resulting peptide-resin, Fmoc-Thr(Bu$^t$)-D-Lys(Boc)-Gly-D-Cys(Trt)-Arg(Pmc)-Resin, was removed in a similar fashion. Fully unprotected peptide was released from the resin by its treatment with TFA. The peptide was purified by reversed phase HPLC and obtained as a lyophilized white powder. Fast atom mass spectrometric analysis gave correct mass for the synthesized peptide.

The peptide may also be synthesized by similar general methods of solid-phase peptide synthesis using Boc-chemistry, as well as solution-phase peptide synthesis methods analogous to those described in Examples 2 and 3.

EXAMPLE 23—PREPARATION OF Thr-D-Lys-Gly-D-Cys-Arg CONJUGATED TO HIGHER MOLECULAR WEIGHT MOLECULES

The conjugation of high molecular weight carrier molecules, such as PEG, PVA, fatty acids and others, to the peptide Thr-D-Lys-Gly-D-Cys-Arg is achieved either after the synthesis of the peptide or during the synthesis of the peptide. The attachment of these carrier molecules to the peptide is by the method of Example 4, or carrier molecules are also attached to the peptide during its synthesis by solid-phase or solution-phase methods of peptide synthesis. The carrier molecules is attached either at the N-terminus or C-terminus or at both termini.

EXAMPLE 24—RADIOLABELING AND FORMULATION OF RADIOPHARMACEUTICALS USING Thr-D-Lys-Gly-D-Cys-Arg

Direct labeling of the peptide: The peptide Thr-D-Lys-Gly-D-Cys-Arg synthesized according to Example 22 was labeled with $^{99m}$Tc in the presence of stannous as reducing agent that was pre-stabilized in a succinate-EDTA buffer. 100 μg of the peptide was mixed with generator eluted $^{99m}$Tc-sodium pertechnetate (1–35 mCi of radioactivity in up to 500 μL volume). To this was added a nitrogen purged solution (200–400 μL) of Stannous-Succinate-EDTA buffer (1 mM-20 mM-1.1 mM, pH 6.2). The head space of the vial was purged with nitrogen and the solution placed in a boiling water bath for 25 min. The solution after cooling can be diluted further with saline. A small aliquot of this $^{99m}$Tc labeled peptide was analyzed by reversed phase HPLC on a C-18 column (VYDAC, Cat. No. 218TP104). A gradient of 0–30% acetonitrile completed in 30 min. at a flow rate of 1.5 mL/min was employed. The radioelution profile was generated by a radio-detection flow cell system attached to the HPLC. The profile indicated that the $^{99m}$Tc-labeled peptide eluted as a major peak that split into a doublet of peaks at its apex (retention times of 12.9 and 13.1 min.). These doublets seemed to represent two isomers of the labeled species due to an isomerism in the $^{99m}$TcO[V] core. A sample of the peptide labeled in a similar fashion but not placed in boiling water bath exhibited additional peaks centered at 14.8 and 16.2 min. which might be due to multimeric species of the peptide-$^{99m}$Tc complex which on heating collapse to the major peak representing a 1:1 peptide-$^{99m}$Tc complex. The elution profile also indicated that the detectable amount of reduced $^{99m}$Tc (not complexed to the peptide) that elutes with the solvent peak (retention time 2.2 min.), if any, was no more than 4%. A 10 μCi sample of the labeled preparation was spotted on an instant thin layer chromatography (ITLC) strip (1.5×10 cm silica gel impregnated strips, Gelman Science, Ann Arbor, Mich.) and developed with 150 mM NaCl. Radioactivity measurements on this strip revealed that the origin had only 2–4.5% of radioactivity which corresponds to the amount of $^{99m}$Tc colloid present in the preparation. The labeled preparation, when stored at room temperature for up to 36 hrs., did not show any change in its HPLC and ITLC profiles. The HPLC and ITLC results together demonstrate a very good $^{99m}$Tc labeling profile for this peptide.

Radiopharmaceutical kit formulation: The peptide Thr-D-Lys-Gly-D-Cys-Arg was also formulated in a kit form to facilitate a convenient $^{99m}$Tc labeling. To achieve this 100 μg of the peptide taken in a 5 mL serum vial was mixed with 400 μL of nitrogen purged stannous-succinate-EDTA buffer (1 mM-20 mM-1.1 mM EDTA, pH 6.2). The head space of the vial was immediately purged with nitrogen. The contents were then lyophilized, filled with argon or nitrogen and sealed. The lyophilized kits can be stored for longer periods of time at 4° C. For technetium labeling a generator eluted $^{99m}$Tc-sodium pertechnetate (1–35 mCi of radioactivity in up to 500 μL volume) was injected into the vial. The contents of the vial were thoroughly mixed, vial vented with an injection needle and placed in a boiling water bath for 25 min. After cooling the contents can be diluted with saline or PBS. Examination of an aliquot by HPLC and ITLC techniques as described above gave results identical to those that were obtained under direct labeling of the peptide.

The peptide Thr-D-Lys-Gly-D-Cys-Arg was also formulated in a kit form with each vial containing 5 μg of the peptide and 400 μL of nitrogen purged stannous-succinate-EDTA buffer (1 mM-20 mM-1.1 mM EDTA, pH 6.2). Kits with 5 μg of peptide were labeled with 2 mCi of $^{99m}$Tc and the equivalent of 50 mCi of $^{99m}$Tc as $^{99}$Tc, for a metal ion concentration equivalent to 52 mCi of $^{99m}$Tc, with no significant radiochemical impurities. The ratio of metal ion to peptide was 1:15.4 with 52 mCi equivalent of $^{99m}$Tc. By increasing the quantity of $^{99}$Tc, successful labeling was achieved at as low as a 1:8 metal ion to peptide ratio using 5 μg kits.

EXAMPLE 25—ALTERNATE RADIOLABELING OF Thr-D-Lys-Gly-D-Cys-Arg

The peptide of Example 22 was also labeled by the direct labeling approach described in Example 24 using alternate buffers for stabilization of the stannous ions. The following alternate buffers were employed: (a) stannous-tartrate-phthalate (1 mM-10 mM-40 mM, pH 6.2), (b) stannous-tartrate-phthalate-glycylglycine (1 mM-10 mM-40 mM-50 mM, pH 6.6), and (c) stannous-tartrate-succinate (1 mM-10 mM-20 mM, pH 6.2). Labeling both at room temperature or at higher temperature (boiling water bath) was performed. HPLC profiles of these preparations were somewhat similar to those described in Example 23. However, relatively higher amounts of the multimeric product species were encountered in the HPLC profiles.

EXAMPLE 26—IMAGING SOUR MLK INDUCED ABSCESS USING $^{99m}$Tc-Thr-D-Lys-Gly-D-Cys-Arg

Figure 8:
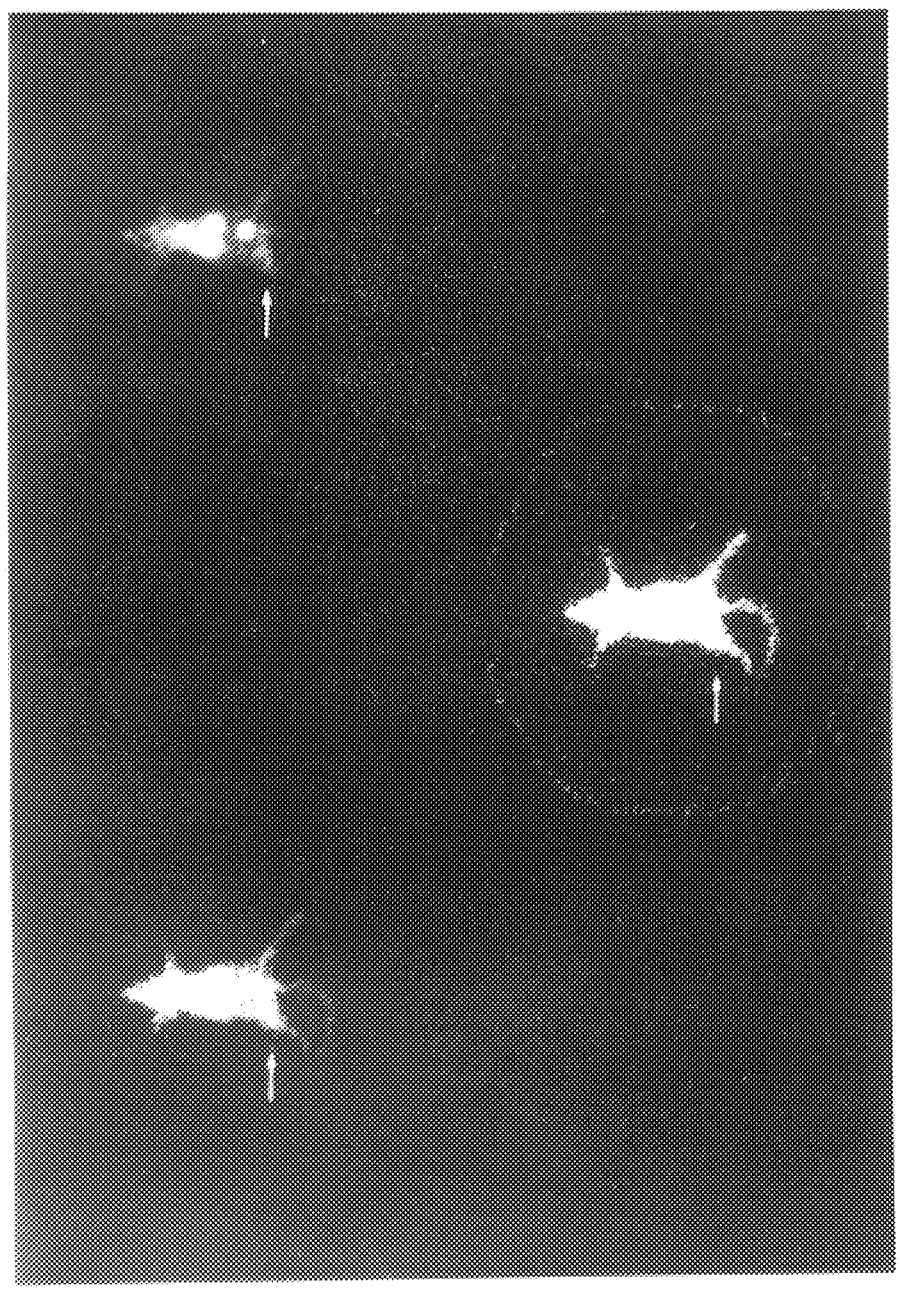
FIG. 8 shows gamma camera images of mice with sour milk induced abscesses in the leg, with the image taken 20 minutes after injection of $^{99m}$Tc-Thr-D-Lys-Gly-D-Cys-Arg.
Figure 9:
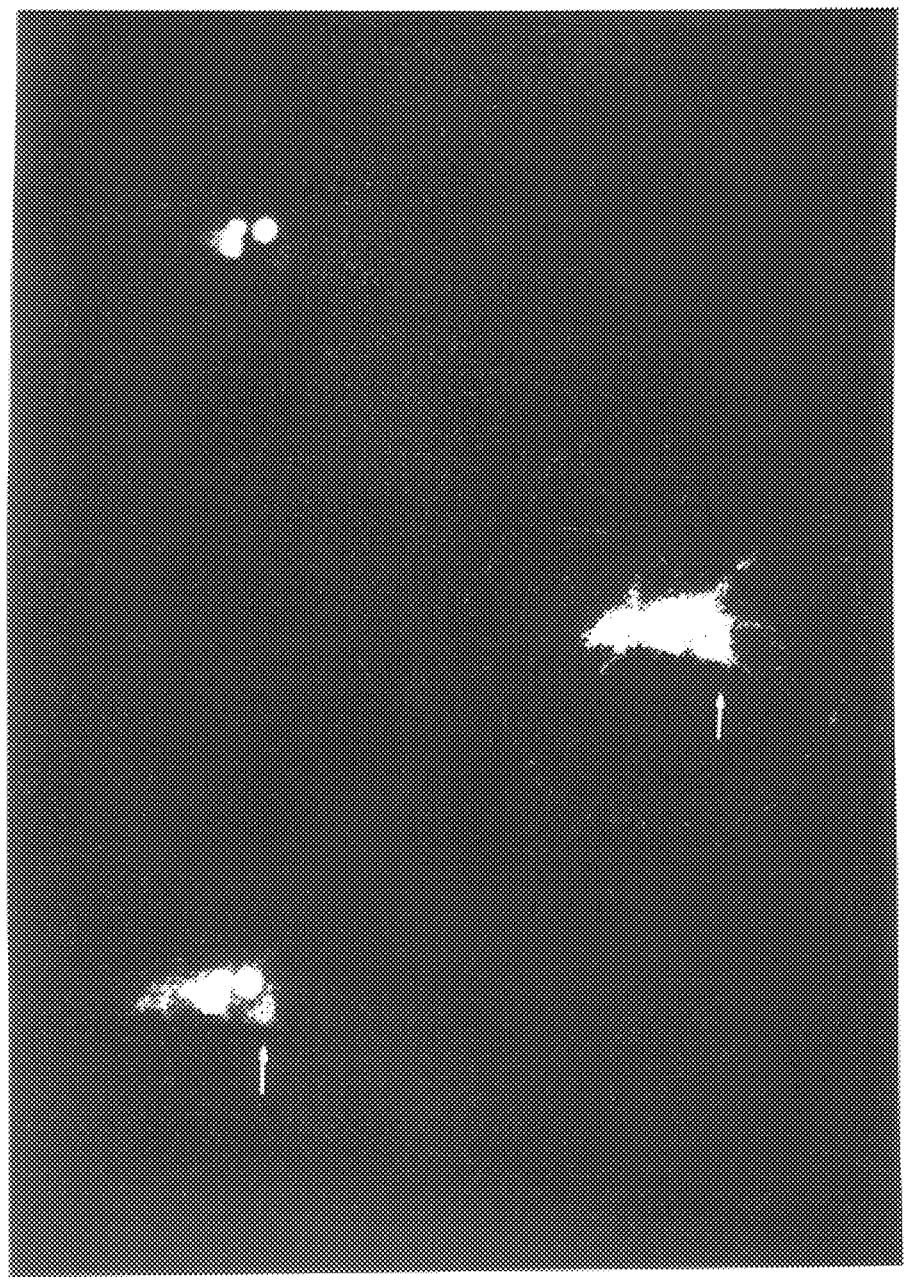
FIG. 9 shows gamma camera images of mice with sour milk induced abscesses in the leg, with the image taken 4 hours after injection of $^{99m}$Tc-Thr-D-Lys-Gly-D-Cys-Arg.

100–200 μL of sour milk (a milk sample allowed to stand at room temperature for 14 hours) was injected in the upper thigh region of a rat or mouse to cause an abscess. After 30–60 min. $^{99m}$Tc-labeled Thr-D-Lys-Gly-D-Cys-Arg preparation (50–200 μCi) of Example 24 was injected through the animal's tail vein. Gamma camera images were taken immediately thereafter by placing the animal on a parallel collimator attached to the camera. During the course of imaging the animal was subdued by intraperitoneal injections of ketamine. The site of abscess was visualized as a result of the accumulation and localization of the $^{99m}$Tc-labeled peptide. Continual imaging was possible for more than 7 hours post injection of the peptide. FIGS. 8 and 9 show gamma camera images of mice with sour milk induced abscesses in the leg. The $^{99m}$Tc-labeled peptide was injected 55 minutes after injection of the sour milk. The image in FIG. 8 was taken 20 minutes after injection of the $^{99m}$Tc-labeled peptide, and the image in FIG. 9 was taken 4 hours after injection of the $^{99m}$Tc-labeled peptide.

EXAMPLE 27—IMAGING KETAMINE INDUCED ABSCESS USING $^{99m}$Tc-Thr-D-Lys-Gly-D-Cys-Arg

100 μL of a saline solution of ketamine (100 mg/mL) was injected in the upper thigh region of a rat or mouse to cause an inflammation. After 30–60 min. a $^{99m}$Tc-labeled Thr-D-Lys-Gly-D-Cys-Arg preparation (50–200 μCi) of Example 24 was injected through the animal's tail vein. Gamma camera images were taken immediately thereafter as described in Example 26. The site of inflammation was visualized as a result of the accumulation and localization of the $^{99m}$Tc-labeled peptide. Continual imaging was possible for more than 2 hours post injection of the peptide.

EXAMPLE 28—STABILITY OF $^{99m}$Tc-Thr-D-Lys-Gly-D-Cys-Arg

100 μL of $^{99m}$Tc-labeled Thr-D-Lys-Gly-D-Cys-Arg peptide labeled with 2 mCi of $^{99m}$Tc and prepared according as described in Example 24 was mixed with an equal volume of human platelet poor plasma (PPP). This was then incubated for one hour at 37° C. An aliquot of this mixture was then analyzed by HPLC under exactly the conditions described in Example 24. A comparison of the generated profile with that of sample not incubated with PPP revealed no difference in the two HPLC profiles. This was suggestive of high stability of the labeled peptide in the plasma.

EXAMPLE 29—SATURATION BINDING OF HUMAN POLYMORPHONUCLEAR CELLS USING $^{99m}$Tc-Thr-D-Lys-Gly-D-Cys-Arg

Figure 10:
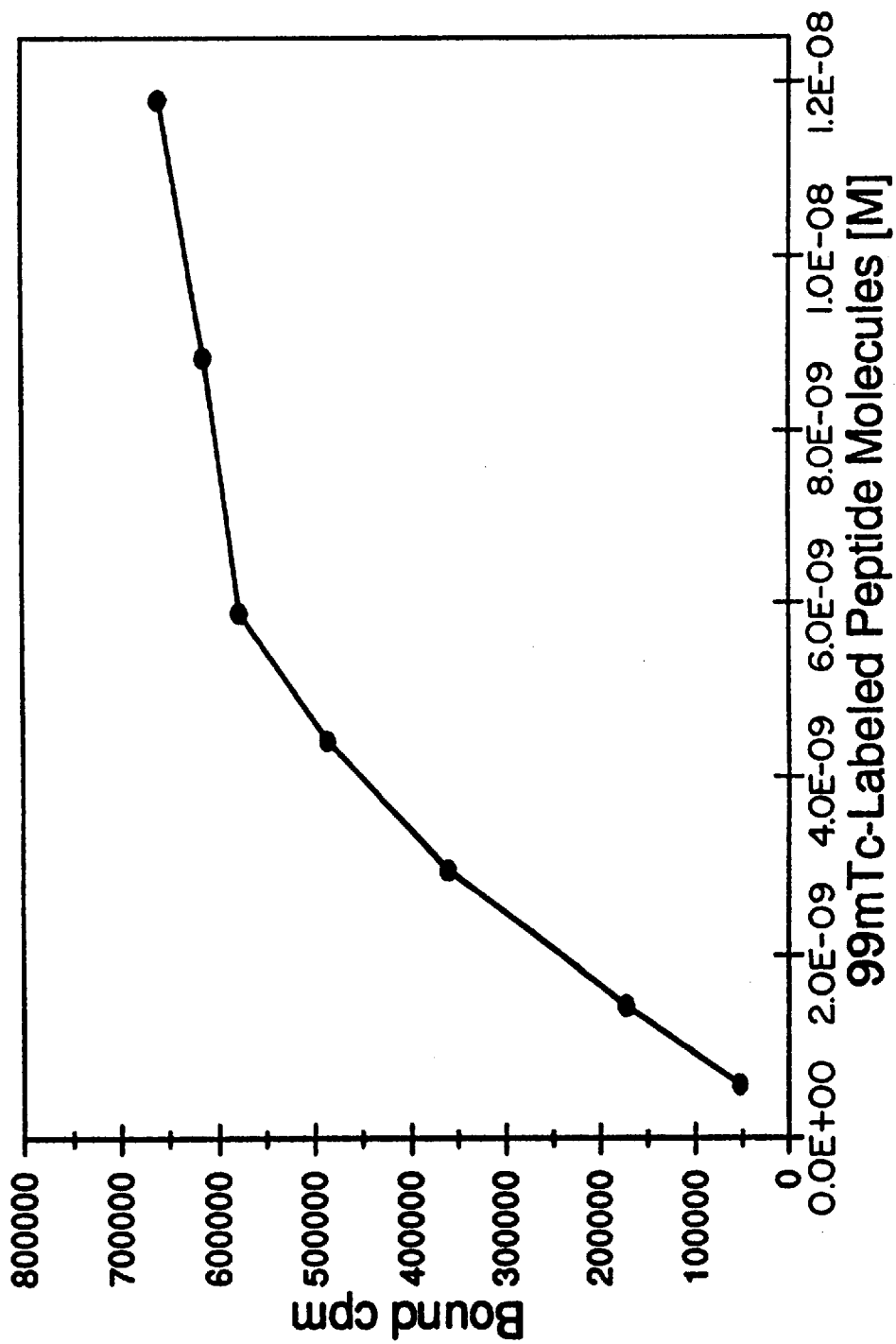
FIG. 10 shows saturation binding isotherm of binding of $^{99m}$Tc-labeled Thr-D-Lys-Gly-D-Cys-Arg with human polymorphonuclear leukocytes.

Saturation binding of $^{99m}$Tc-labeled Thr-D-Lys-Gly-D-Cys-Arg peptide prepared by the method of Example 24 to human PMN leukocytes was demonstrated using both freshly collected PMN leukocytes from human blood as well as formalin fixed PMN leukocytes. The concentration of PMN cells in the PBS as incubation medium was $2.5\times10^6$ cells/mL per one assay tube. Increasing amounts of $^{99m}$Tc-labeled peptide was added to constant amounts of cells taken in different assay tubes. Similar volumes of PBS were used at each concentration of the $^{99m}$Tc-labeled peptide as a measure of the non-specific binding component under the experimental conditions. The binding was allowed to take place for 30 min. after which the tubes were transferred to an ice bath. A 200 µL aliquot corresponding to $0.5\times10^6$ cells was filtered through a glass fiber filter that was presoaked in 50% calf serum in PBS for 30 min. The filters were then washed three times with 1 mL of PBS and counted in a gamma counter for the bound radioactivity. The data was normalized to account for the decay of $^{99m}$Tc and plotted. The results reveal saturation binding kinetics of the peptide for its receptor on PMN cells. An analysis of the data gave an value for $K_D$ in the range of 1–5 nM. FIG. 10 shows the binding curve obtained in this experiment.

EXAMPLE 30—SATURATION BINDING OF HL-60 CELLS USING $^{99m}$Tc-Thr-D-Lys-Gly-D-Cys-Arg

Saturation binding of $^{99m}$Tc-labeled Thr-D-Lys-Gly-D-Cys-Arg peptide prepared by the method of Example 24 to HL-60 cells (a human leukemic cell line) was demonstrated using both freshly cultured HL-60 cells as well as formalin fixed HL-60 cells. The assay was performed as described for PMN leukocytes in Example 29. An analysis of the data gave an value for $K_D$ in the range of 1–5 nM.

EXAMPLE 31—COMPETITION BINDING TO HUMAN POLYMORPHONUCLEAR CELLS USING $^{99m}$Tc-Thr-D-Lys-Gly-D-Cys-Arg AND $^{99}$Tc-Thr-D-Lys-Gly-D-Cys-Arg

Figure 11:
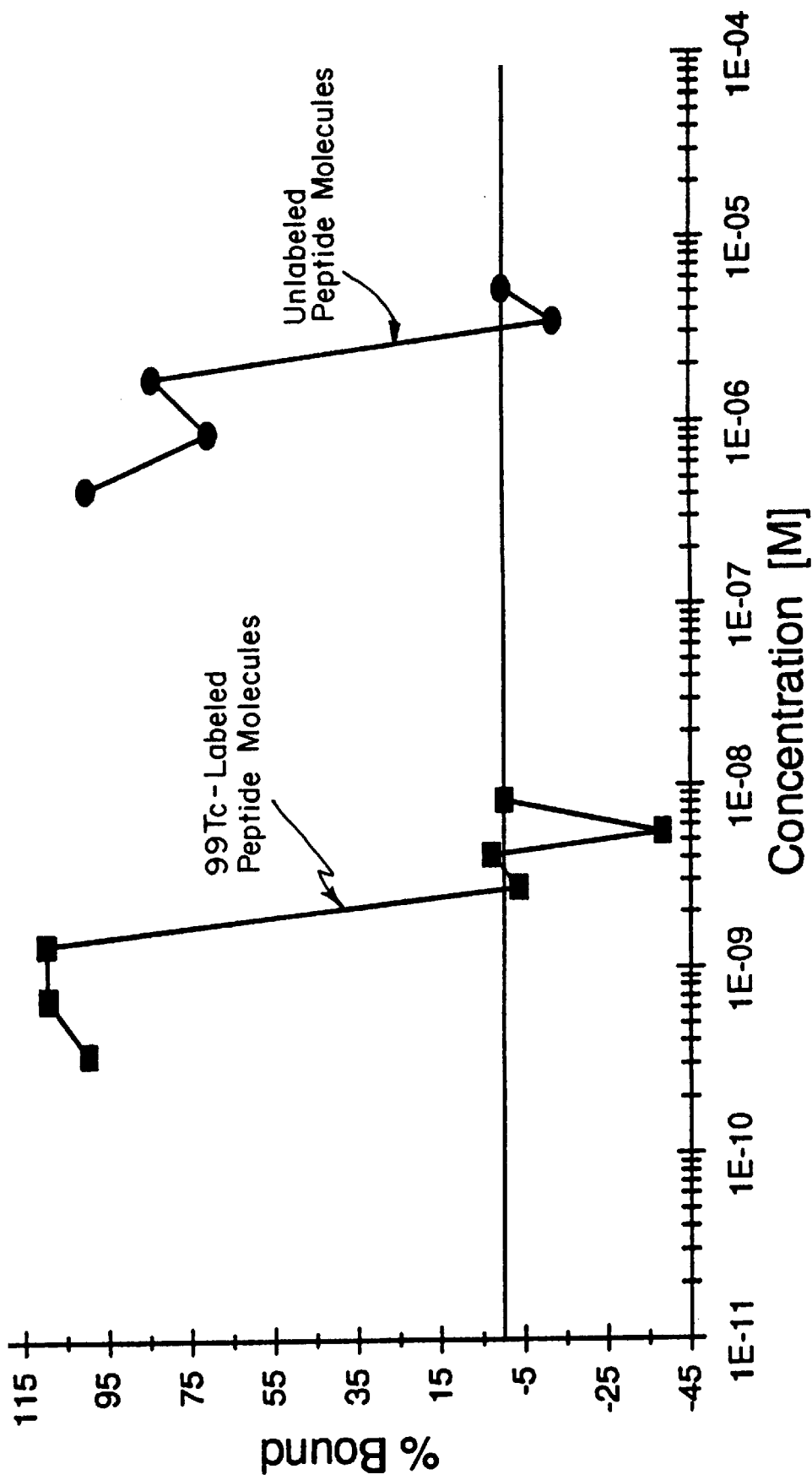
FIG. 11 shows results of competition binding of $^{99}$Tc-labeled Thr-D-Lys-Gly-D-Cys-Arg and unlabeled Thr-D-Lys-Gly-D-Cys-Arg with $^{99m}$Tc-labeled Thr-D-Lys-Gly-D-Cys-Arg for binding to human polymorphonuclear leukocytes.

Formalin fixed PMN leukocytes ($2.5\times10^6$ cells in a final volume of one mL per assay tube), as generally discussed in Example 29, were incubated with a mixture of $^{99m}$Tc-labeled Thr-D-Lys-Gly-D-Cys-Arg and $^{99}$Tc-labeled Thr-D-Lys-Gly-D-Cys-Arg peptide. A constant but tracer amount of the $^{99m}$Tc labeled peptide was used in this assay. The amount of $^{99}$Tc-labeled peptide, however, varied between $10^{-9}$M to $10^{-7}$M in terms of the $^{99}$Tc labeled fraction of the peptide molecules. For this experiment, both the $^{99m}$Tc-labeled as well as the $^{99}$Tc-labeled peptides were prepared according to the methods of Example 24, with the assay performed as described in Example 29. The data from this assay showed that the $K_D$ value for the $^{99m}$Tc-labeled peptide was in the range of 1–5 nM, while the. This value is similar to the ones obtained in various saturation binding experiments described in Examples 28. FIG. 11 shows the binding curves obtained in this experiment for $^{99}$Tc-labeled peptide.

EXAMPLE 32—COMPETITION BINDING TO HUMAN POLYMORPHONUCLEAR CELLS USING $^{99m}$Tc-Thr-D-Lys-Gly-D-Cys-Arg AND UNLABELED Thr-D-Lys-Gly-D-Cys-Arg

This experiment was conducted using the methods of Example 31, except that unlabeled Thr-D-Lys-Gly-D-Cys-Arg peptide, in concentrations from $10^{-10}$M to $10^{-4}$M, was used. The unlabeled peptide did not effectively compete with the $^{99m}$Tc-labeled peptide. The calculated $K_D$ value for unlabeled peptide was over $10^{-5}$M, substantially higher than the $K_D$ value for the $^{99m}$Tc-labeled peptide. This results indicates that the $^{99m}$Tc and $^{99}$Tc-labeled peptide molecules are biologically active, while the unlabeled peptide has marginal biological activity. FIG. 11 shows the binding curves obtained in this experiment for unlabeled peptide, together with the binding curve for $^{99}$Tc-labeled peptide.

EXAMPLE 33—COMPETITION BINDING TO HUMAN POLYMORPHONUCLEAR CELLS OF $^{99m}$Tc-Thr-D-Lys-Gly-D-Cys-Arg USING NATURAL TUFTSIN

Formalin fixed PMN leukocytes ($2.5\times10^6$ cells in a final volume of one mL per assay tube), as described in Example 29, were incubated with a mixture of $^{99m}$Tc-labeled Thr-D-Lys-Gly-D-Cys-Arg and natural tuftsin Thr-Lys-Pro-Arg (SEQ. ID NO. 5) peptide. A constant but tracer amount of the $^{99m}$Tc-labeled peptide was prepared as described in Example 29. The amount of the unlabeled peptide, however, varied between $10^{-10}$M to $10^{-5}$M. The assay was performed according to the description in Example 29. The results yielded a $K_D$ for natural tuftsin in the range of 100 nM, which is consistent with the results obtained by earlier investigators. The results also demonstrated that $^{99m}$Tc-Thr-D-Lys-Gly-D-Cys-Arg binds the same receptor as the naturally occurring tuftsin molecule.

EXAMPLE 34—COMPETITION BINDING TO HL-60 CELLS USING $^{99m}$Tc-Thr-D-Lys-Gly-D-Cys-Arg AND $^{99}$Tc-Thr-D-Lys-Gly-D-Cys-Arg

Competition binding of $^{99m}$Tc-labeled Thr-D-Lys-Gly-D-Cys-Arg and $^{99}$Tc-labeled Thr-D-Lys-Gly-D-Cys-Arg for the tuftsin receptor on HL-60 cells was also performed according to the method of Example 29, using HL-60 cells as described in Example 30. The $K_D$ value of 1–5 nM for $^{99}$Tc-labeled Thr-D-Lys-Gly-D-Cys-Arg obtained was similar to that obtained for the corresponding $^{99m}$Tc-labeled peptide in saturation binding experiment of Example 30.

EXAMPLE 35—COMPETITION BINDING TO HL-60 CELLS USING $^{99m}$Tc-Thr-D-Lys-Gly-D-Cys-Arg AND UNLABELED Thr-D-Lys-Gly-D-Cys-Arg

Competition binding of $^{99m}$Tc-labeled Thr-D-Lys-Gly-D-Cys-Arg and Thr-D-Lys-Gly-D-Cys-Arg peptide for the tuftsin receptor on HL-60 cells was performed according to the method of Example 32. A $K_D$ value of $>10^{-5}$M for Thr-D-Lys-Gly-D-Cys-Arg peptide was obtained, confirming that the corresponding $^{99m}$Tc- or $^{99}$Tc-labeled species was the biologically active species.

EXAMPLE 36—COMPETITION BINDING TO HL-60 CELLS OF $^{99m}$Tc-Thr-D-Lys-Gly-D-Cys-Arg USING NATURAL TUFTSIN

Competition binding of $^{99m}$Tc-labeled Thr-D-Lys-Gly-D-Cys-Arg and naturally occurring tuftsin Thr-Lys-Pro-Arg (SEQ. ID NO. 5) peptide for the tuftsin receptor on HL-60 cells was also performed according to the method of Example 33. A similar $K_D$ value of 100 nM for natural Thr-Lys-Pro-Arg (SEQ. ID NO. 5) peptide was obtained from this experiment, as was the observation that the $^{99m}$Tc-labeled Thr-D-Lys-Gly-D-Cys-Arg binds to the same receptor as natural tuftsin, but the $^{99m}$Tc-labeled peptide has higher affinity for its receptor than does the natural peptide.

EXAMPLE 37—IMAGING RABBIT WITH TURPENTINE-INDUCED STERILE ABSCESS USING $^{99m}$Tc-Thr-D-Lys-Gly-D-Cys-Arg

Figure 12:
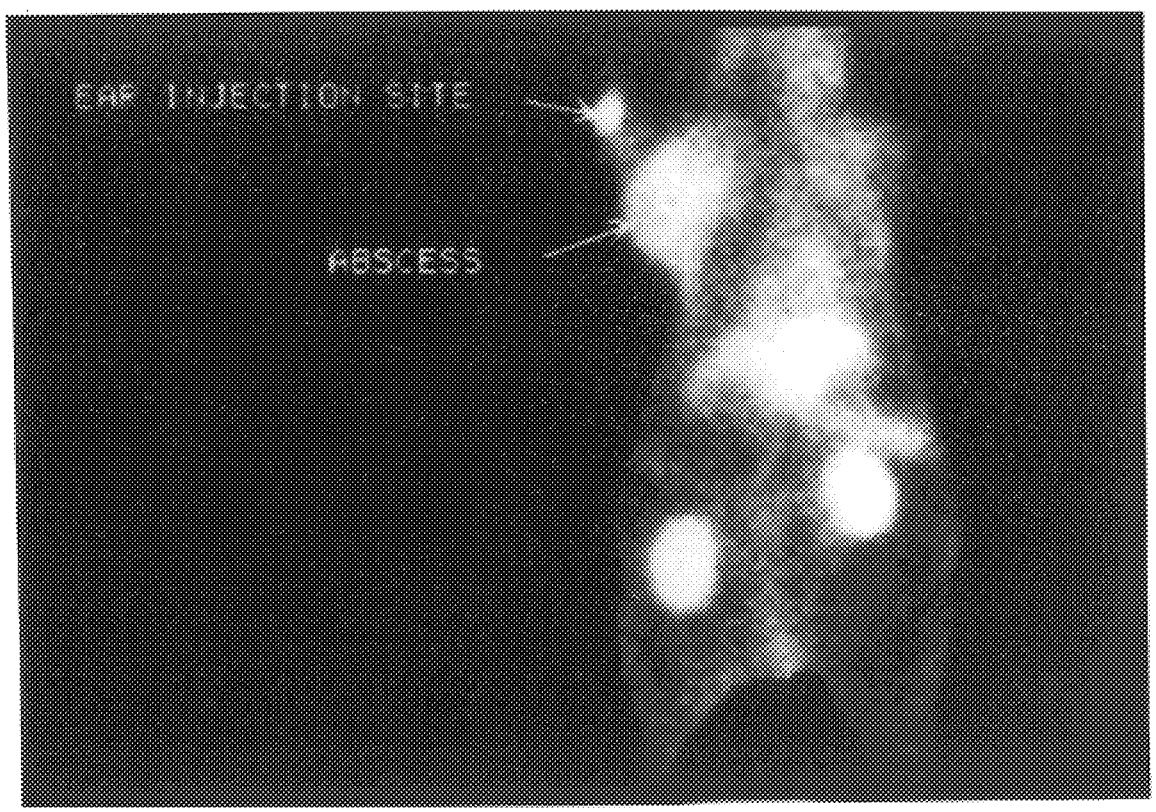
FIG. 12 shows gamma camera images of a turpentine-induced abscess in a rabbit, with the image taken 15 minutes after injection of $^{99m}$Tc-Thr-D-Lys-Gly-D-Cys-Arg.

Turpentine was injected into the left hind thigh of a rabbit, according to a previously described animal model (Tsan M F: Studies of gallium accumulation in inflammatory lesions: III Role of polymorphonuclear leukocytes and bacteria, *J. Nucl. Med.* 19:492–495, 1978). Four day later an injection of 0.5 mCi $^{99m}$Tc-Thr-D-Lys-Gly-D-Cys-Arg prepared according to Example 24 was administered to the rabbit through its ear vein. Scintigraphic images were obtained that visualized the abscess site within 10 min. post injection of the peptide. FIG. 12 shows the results obtained at 15 minutes post injection. The abscess could be visualized for the course of the study period, four hours post injection.

EXAMPLE 38—IMAGING RABBIT WITH WHIFFLE BALL-INDUCED INFLAMMATION USING $^{99m}$Tc-Thr-D-Lys-Gly-D-Cys-Arg

A whiffle ball was implanted subcutaneously in the left hind thigh of a rabbit using a reported model (Tsan MF, supra). Seven days later an injection of casein was made into the whiffle ball to cause a localized inflammation which was followed by an injection of 0.5 mCi $^{99m}$Tc-Thr-D-Lys-Gly-D-Cys-Arg prepared by the method of Example 24 and administered to the rabbit through its ear vein. Scintigraphic images were obtained that visualized the inflammation site within the whiffle ball 10 min. post injection, and the images persisted for the course of the study period, four hours post injection.

EXAMPLE 39—IMAGING HL-60 TUMORS IN MOUSE MODEL USING $^{99m}$Tc-Thr-D-Lys-Gly-D-Cys-Arg 500,000 HL-60 cells were mixed with 100 μL of a solution of Matrigel®, a basement membrane maxtrix product distributed by Becton Dickinson Labware (Bedford, Mass.), in saline (0.1% in saline). This was injected subcutaneously in the left hind thigh of a nude mouse, forming a visible and palpable tumor xenograft within 10 to 20 days. Between 20 and 40 μCi of $^{99m}$Tc-Thr-D-Lys-Gly-D-Cys-Arg prepared according to Example 24 was injected through the tail vein of the mouse. Whole body scintigraphic images of the mouse were taken starting 10 min. post peptide injection. The localization of the peptide to the xenograft was visualized within 10 min. and was observed throughout the experimentation period of six hours.

EXAMPLE 40—IMAGING TUMORS USING $^{99m}$Tc-Thr-D-Lys-Gly-D-Cys-Arg

Patients with tumors of various types, including small cell lung cancer, mammary cancer, prostrate cancer, and melanoma, are injected with 5–20 mCi of $^{99m}$Tc-Thr-D-Lys-Gly-D-Cys-Arg prepared according to Example 24 or 25. Periodic whole body scintigraphic images are obtained starting 10 min. post injection to observe the localization of the radiolabeled peptide to the sites of cancer. The effectiveness of the labeled peptide to image these tumors is noted.

EXAMPLE 41—IMAGING ABSCESSES AND INFLAMMATION USING $^{99m}$Tc-Thr-D-Lys-Gly-D-Cys-Arg

Patients with suspected sites of abscess or inflammation are injected with 5–20 mCi of $^{99m}$Tc-Thr-D-Lys-G ly-D-Cys-Arg prepared according to Example 24 or 25. Periodic whole body scintigraphic images are obtained starting 10 min. post injection to observe the localization of the radiolabeled peptide to the sites of abscess or inflammation. The effectiveness of the labeled peptide to image these sites is noted.

EXAMPLE 42—ISOSTERIC REPLACEMENT OF A DISULFIDE, LACTAM OR LACTONE BRIDGE IN A CYCLIC PEPTIDE

A precursor molecule was designed that consists of a well designed metal binding domain to replace a disulfide, lactam, or a lactone bridge in a parent peptide. The isoster moiety is designed to be placed at the location of two cysteines forming a disulfide in a peptide or the two amino acids forming a lactam or lactone bridge in a peptide. The presence of the precursor molecule not bound to the requisite metal ion affords a much higher conformational freedom than the original disulfide, or lactam or lactone bridge thereby making them either biologically inactive or less potent. However, upon binding the metal ion the molecule gets in a conformational restriction similar to that afforded by the disulfide, or lactam, or a lactone bridge. In a biologically active molecule where these bridges are known to be crucial for bioactivity this approach of metal complexation to the precursor molecule is designed to restore the conformation and the topography of the key receptor recognizing and activating elements. The general structure of the precursor molecule and its placement in a peptide chain is as follows:

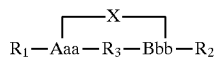

Where:
  X=A complexing backbone for complexing metal ion containing two or more amino acids, so that all of said valances of the metal ion are satisfied upon complexation of the metal ion with X,
  $R_1$ and $R_2$=Each include from 0 to about 20 amino acids,
  $R_3$=From 1 to about 20 amino acids,
  Aaa and Bbb=Each comprise an amino acid connected to X through an amide, thioether or ester bond.

The sequence X can be made of amino acids containing at least one nitrogen, sulfur or oxygen atom available for complexing with the available valences of the metal ion. If less than all of the valances of the metal ion are satisfied upon complexation of the metal ion with the amino acids included in X, then X also includes a derivatized peptide or spacer sequence, which includes at least one nitrogen, sulfur or oxygen atom available for complexing with the available valences of the metal ion, so that all of said valences of the metal ion are satisfied upon complexation of the metal ion with X. The sequence X can be an amino acid sequence of the formula Ccc-Ddd-Eee or Eee-Ddd-Ccc. In this case, each of Ccc and Ddd can be an amino acid or dipeptide with uncharged side chains, and Eee can be a L- or D-isomer of Cys, HomoCys, or Pen, or other synthetic or derivatized amino acid containing an S, and preferably containing an S and an N, available for binding to a metal ion. Aaa can be a L- or D-isomer of an amino acid terminating in a carboxyl group or in an amine group. Bbb is a L- or D-isomer of an amino acid terminating in a carboxyl group or in an amino group, selected such that if Bbb has a side chain terminating in a carboxyl group, Eee has a side chain terminating in an amino group, and if Bbb has a side chain terminating in an amino group, Eee has a side chain terminating in a carboxyl group.

The precursor molecule for isosteric replacement of a disulfide, lactam or lactone bridge thus includes constructs on the following models:

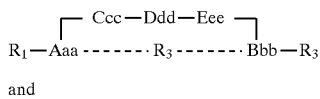

and

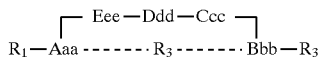

Where: Aaa and Bbb=An amino acid with its side chain terminating either in a carboxyl group (Asp, Glu or similar synthetic amino acid), or in an amino group (Orn, Lys, or similar unnatural amino acid). Both L and D isomers of these amino acids could be substituted at this position. If Aaa is a carboxyl group, then Bbb is an amino group, and if Aaa is an amino group, then Bbb is a carboxyl group.

Ccc and Ddd=L- or D-isomers of Gly, Ala, Aib, Val, Nle, Leu, or a similar amino acids with un-charged side chains, or a dipeptide comprising any of these amino acids. Aaa is also a dipeptide composed of a combination of these amino acids.

Eee=L-Cys, D-Cys, L-HomoCys, D-HomoCys, L-Pen, D-Pen, or a similar synthetic or derivatized peptide containing a S for complexing with a metal ion, and preferably a S and a N for complexing with a metal ion.

$R_1$, $R_2$ and $R_3$=$R_1$ and $R_2$ are from 0 to about 20 amino acid residues, and $R_3$ is from 1 to about 20 amino acid residues, all or any portion of which makes up all or part of the biological-function domain. The biological-function domain may be sychnological or rhegnylogical.

EXAMPLE 43—ISOSTERIC REPLACEMENT OF A DISULFIDE BRIDGE IN A CYCLIC SOMATOSTATIN PEPTIDE

A Somatostatin Analogue with a Disulfide Bridge Isoster: The biological activity of somatostatin and its analogues depend on the integrity of its disulfide bond. Reduction of this bond that opens up the ring structure is known to be detrimental to its biological activity. A typical and known somatostatin molecule is of the formula:

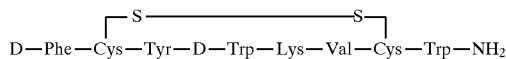

Following is a molecule of somatostatin designed according to Example 42 that has a $^{99m}$Tc, $^{99}$Tc, $^{188}$Re, or $^{186}$Re binding domain that replaces a disulfide bridge in the above mentioned parent somatostatin analogue:

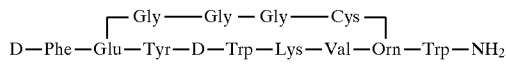

This molecule after binding to the requisite metal ion gains biological activity, and bind to the somatostatin receptor.

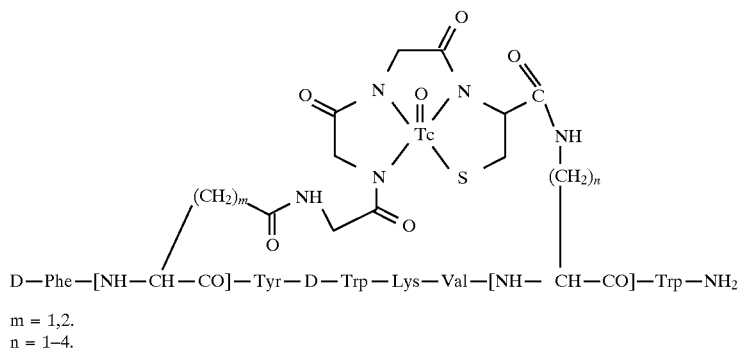

m = 1,2.
n = 1–4.

This molecule can be easily synthesized by well known methods of solid-phase peptide synthesis. The labeling of this molecule with metal ions can be achieved easily by methods described in Examples 5–10, or modifications thereof.

EXAMPLE 44—ISOSTERIC REPLACEMENT OF A LACTAM BRIDGE IN A CYCLIC MELANOTROPIN PEPTIDE

A Melanotropin Analogue with a Lactam Bridge Isoster: The high potency of the following melanotropin analogue depends on the integrity of its lactam bridge. Absence of this bridge and resulting conformational constraint is known to be detrimental to its biological activity. A melanotropin cyclic peptide of the general formula

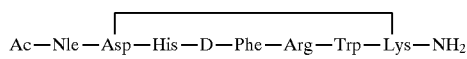

was used as the starting material.

The following molecule is designed according to the method of Example 42, and has a $^{99m}$Tc, $^{99}$Tc, $^{188}$Re, or $^{186}$Re binding domain that replaces the lactam bridge in the parent melanotropin analogue:

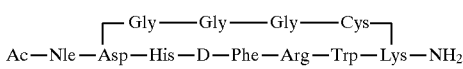

This precursor molecule, after binding to the requisite metal ion, has biological activity at the melanotropin receptor.

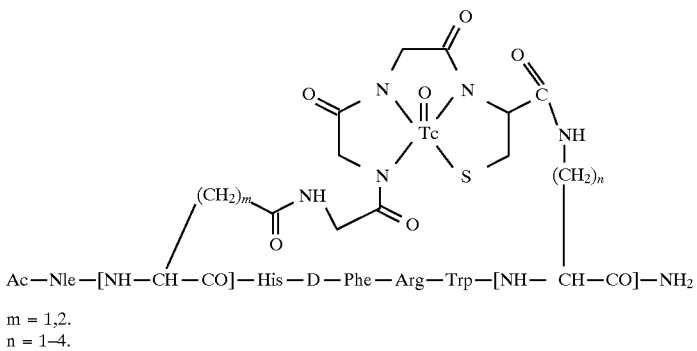

Ac—Nle—[NH—CH—CO]—His—D—Phe—Arg—Trp—[NH—CH—CO]—NH₂ m = 1,2.
n = 1–4.

This molecule can been easily synthesized by well known methods of solid-phase peptide synthesis. The labeling of this molecule with metal ions can be achieved easily by methods described in Examples 5–10, or modifications thereof.

EXAMPLE 45—SOMATOSTATIN ANALOGUE PEPTIDE FOR $^{111}$IN LABELING

A linear peptide D-Phe-Lys(N$^\epsilon$ bis carboxymethyl)-Tyr-D-Trp-Lys-Val-Lys(N$^\epsilon$ bis carboxylmethyl)-Trp-NH$_2$ is synthesized according to well established methods of solution phase or solid phase peptide synthesis. This sequence, after complexation with $^{111}$In, binds to somatostatin receptors. A solution of the peptide is made in an appropriate buffer and is mixed with $^{111}$InCl$_3$ to yield a $^{111}$In labeled peptide species in which the conformation of the peptide is folded and fixed by the complexation of an $^{111}$In metal ion to the carboxymethyl groups placed on the $\epsilon$-amino groups of the two lysine residues in the peptide sequence. Those peptide molecules which are not complexed to $^{111}$In do not bind the somatostatin receptor.

EXAMPLE 46—MELANOTROPIN ANALOGUE PEPTIDE FOR $^{111}$IN LABELING

A peptide Ac-Nle-Lys(N$^\epsilon$ bis carboxymethyl)-His-D-Phe-Arg-Trp-Lys(N$^\epsilon$ bis carboxylmethyl)-NH$_2$ is synthesized according to well established methods of solution phase or solid phase peptide synthesis. After complexation with $^{111}$In this peptide binds to melanotropin receptors. A solution of the peptide is made in an appropriate buffer and is mixed with $^{111}$InCl$_3$ to yield a $^{111}$In labeled peptide species in which the conformation of the peptide is fixed by the complexation of an $^{111}$In metal ion to the carboxymethyl groups placed on the $\epsilon$-amino groups of the two lysine residues in the peptide sequence. The portion of the peptide molecules that remain uncomplexed to $^{111}$In do not bind melanotropin receptors.

EXAMPLE 47—ESTROGEN ANALOGUE PEPTIDE FOR Tc or Re LABELING

A peptide derivative, Tic(7-OH)-Thr-NH(CH$_2$)$_2$SH or D-Tic(7-OH)-D-Thr-NH(CH$_2$)$_2$SH, is synthesized according to the well established methods of peptide synthesis as a ligand designed to mimic estrogen upon its complexation with $^{99m}$TcO[V] or ReO[V]. The peptide derivative Tic(7-OH)-Thr-NH(CH$_2$)$_2$SH has biological activity as an estrogen analogue after labeling with a metal ion, and has the following structure:

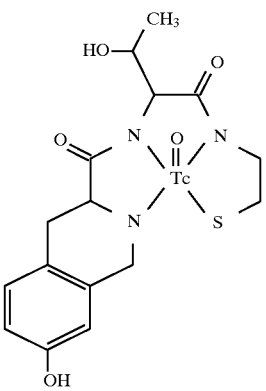

The peptide is labeled according to the methods similar to those described in Examples 5–10, or 24–25, or modifications thereof. The labeled molecule binds the estrogen receptor whereas the unlabeled molecule has little or no affinity for this receptor.

EXAMPLE 48—ALTERNATE ESTROGEN ANALOGUE PEPTIDE FOR Tc or Re LABELING

A peptide derivative with the structure Tic(7-OH)-Ser-Cys or D-Tic(7-OH)-D-Ser-Cys is synthesized according to well established methods of peptide synthesis as another ligand designed to bind estrogen receptor after its complexation with $^{99m}$TcO[V] or ReO[V]. The peptide derivative Tic(7-OH)-Ser-Cys has biological activity as an estrogen analogue after labeling with a metal ion, and has the following structure:

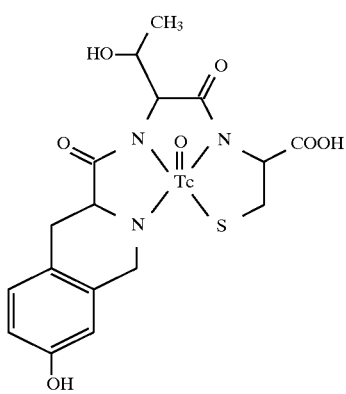

The peptide is labeled according to the methods similar to those described in Examples 5–10, or 24–25, or modifications thereof. The labeled molecule binds the estrogen receptor whereas the unlabeled molecule has little or no affinity for this receptor.

EXAMPLE 49—LAMININ-DERIVED YIGSR PEPTIDE ANALOGUE FOR Tc or Re LABELING

Platelets contain a 67 kDa receptor which binds to laminin-derived peptide sequences containing Tyr-Ile-Gly-Ser-Arg (YIGSR) (SEQ. ID NO. 3) (Tandon N N, Holland E A, Kralisz U, Kleinman H K, Robey F A, and Jamieson G A: Interaction of human platelets with laminin and identification of the 67 kDa laminin receptor on platelets, *Biochem J* 274(1991) 535–542). This platelet receptor appears to play an important role in the interaction of platelets with the intact laminin molecule. Platelet adherence to laminin via this receptor does not in itself result in platelet activation (Ill C R, Engvall E, and Ruoslahti E: Adhesion of platelets to laminin in the absence of activation. *J Cell Biol* 99(1984) 2140–2145).

Peptides containing the YIGSR (SEQ. ID NO. 3) peptide sequence have been proposed as anti-metastatic agents. Schasteen C S, U.S. Pat. No. 5,039,662, Peptide with Anti-Metastatic Activity; Yamada Y, Graf J O, Iwamoto Y, Rober F, Kleinman H K, Sasaki M and Martin G R, U.S. Pat. No. 5,092,885, Peptides with Laminin Activity; and Saiki I, Nishi N, Azuma I, Tokura S, U.S. Pat. No. 5,236,903 Polypeptide Comprising Repeated Cell-Adhesive Core Sequences. These patents involve longer sequences containing the YIGSR (SEQ. ID NO. 3) peptide sequence, acylated YIGSR peptide sequences, cyclic YIGSR (SEQ. ID NO. 3) sequences, and repeated YIGSR linear sequences.

A peptide derivative, Tyr-Ile-Gly-Ser-Cys-Arg (SEQ. ID NO. 6), is synthesized according to the well established methods of peptide synthesis as a ligand designed to mimic the adhesive pentapeptide sequence, YIGSR (SEQ. ID NO. 3), of laminin upon its complexation with $^{99m}$TcO[V] or ReO[V]. The peptide is labeled according to the methods similar to those described in Examples 5–10, or 24–25, or modifications thereof. The labeled molecule binds the laminin receptor, while the unlabeled molecule has little or no affinity for this receptor.

EXAMPLE 50—USE OF SOMATOSTATIN ANALOGUES FOR CANCER IMAGING

The somatostatin analogues of any of Examples 43 or 45 are labeled with between 5 and 20 mCi of $^{99m}$Tc, or in the case of Example 45, with between 2 and 10 mCi of $^{111}$In, using methods similar to those described in Examples 5–10, or 24–25, or modifications thereof. The labeled somatostatin analogues are administered, by i.v. injection or regional delivery, to patients suspected of having somatostatin-receptor positive cancers, and periodic whole body scintigraphic images are obtained starting 10 min. post injection to determine the localization of the radiolabeled peptide to the tumor site or sites. The effectiveness of the labeled peptide to image these tumors is noted.

EXAMPLE 51—USE OF MELANOTROPIN ANALOGUES FOR CANCER IMAGING

The melanotropin analogues of any of Examples 44 or 46 are labeled with between 5 and 20 mCi of $^{99m}$Tc, or in the case of Example 46, with between 2 and 10 mCi of $^{111}$In, using methods similar to those described in Examples 5–10, or 24–25, or modifications thereof. The labeled melanotropin analogues are administered, by i.v. injection or regional delivery, to patients suspected of having melanotropin-receptor positive cancers, such as melanomas, and periodic whole body scintigraphic images are obtained starting 10 min. post injection to determine the localization of the radiolabeled peptide to the tumor site or sites. The effectiveness of the labeled peptide to image these tumors is noted.

EXAMPLE 52—USE OF ESTROGEN ANALOGUES FOR CANCER IMAGING

The estrogen analogues of any of Examples 47 and 48 are labeled with between 5 and 20 mCi of $^{99m}$Tc using methods similar to those described in Examples 5–10, or 24–25, or modifications thereof. The labeled estrogen analogues are administered, by i.v. injection or regional delivery, to patients suspected of having estrogen-receptor positive cancers, such as breast cancer, and periodic whole body scintigraphic images are obtained starting 10 min. post injection to determine the localization of the radiolabeled peptide to the tumor site or sites. The effectiveness of the labeled peptide to image these tumors is noted.

EXAMPLE 53—USE OF SOMATOSTATIN ANALOGUES FOR CANCER THERAPY

The somatostatin analogues of Example 43 is labeled with between 1 and 100 mCi of either $^{186}$Re or $^{188}$Re, using methods similar to those described in Examples 5–10, or 24–25, or modifications thereof, with increased Sn (II) concentrations as required to reduce the perrhenate. Patients are optionally selected who have demonstrated somatostatin-receptor positive tumors, which may conveniently be done by diagnostic imaging of Example 50. The labeled somatostatin analogues are administered, by i.v. injection or regional delivery, to patients suspected of having somatostatin-receptor positive cancers, with repeat administrations given as necessary to obtain the desired therapeutic effect. Since both $^{186}$Re or $^{188}$Re emit both gamma and beta radiation, periodic whole body gamma scintigraphic images may be obtained starting as soon as 10 min. post injection to determine the localization of the radiolabeled peptide to the tumor site or sites. The effectiveness of the labeled peptide to treat these tumors is noted.

EXAMPLE 54—USE OF MELANOTROPIN ANALOGUES FOR CANCER THERAPY

The melanotropin analogues of Example 44 is labeled with between 1 and 100 mCi of either $^{186}$Re or $^{188}$Re, using methods similar to those described in Examples 5–10, or 24–25, or modifications thereof, with increased Sn (II) concentrations as required to reduce the perrhenate. Patients with melanoma are optionally selected who have demonstrated melanotropin-receptor positive tumors, which may conveniently be done by diagnostic imaging of Example 51. The labeled melanotropin analogues are administered, by i.v. injection or regional delivery, to patients suspected of having melanoma or melanotropin-receptor positive cancers, with repeat administrations given as necessary to obtain the desired therapeutic effect. Since both $^{186}$Re or $^{188}$Re emit both gamma and beta radiation, periodic whole body gamma scintigraphic images may be obtained starting as soon as 10 min. post injection to determine the localization of the radiolabeled peptide to the tumor site or sites. The effectiveness of the labeled peptide to treat these tumors is noted.

EXAMPLE 55—USE OF ESTROGEN ANALOGUES FOR CANCER THERAPY

The estrogen analogues of any of Examples 47 and 48 are labeled with between 1 and 100 mCi of either $^{186}$Re or $^{188}$Re, using methods similar to those described in Examples 5–10, 24–25, or modifications thereof, with increased Sn (II) concentrations as required to reduce the perrhenate. Patients are optionally selected who have demonstrated breast cancer or other estrogen-receptor positive tumors, which may conveniently be done by diagnostic imaging of Example 52. The labeled estrogen analogues are administered, by i.v. injection or regional delivery, to patients suspected of having estrogen-receptor positive cancers, with repeat administrations given as necessary to obtain the desired therapeutic effect. Since both $^{186}$Re or $^{188}$Re emit both gamma and beta radiation, periodic whole body gamma scintigraphic images may be obtained starting as soon as 10 min. post injection to determine the localization of the radiolabeled peptide to the tumor site or sites. The effectiveness of the labeled peptide to treat these tumors is noted.

EXAMPLE 56—IMAGING OF THROMBOSIS USING $^{99m}$Tc-D-Arg-Gly-D-Cys-β-Ala

The RGD analogue D-Arg-Gly-D-Cys-β-Ala of any of Examples 1–4 is radiolabeled by any of the methods of Example 5–10, or modifications thereof, with between 5 and 20 mCi of $^{99m}$Tc. The labeled RGD analogue is administered by i.v. injection to patients suspected of having thrombosis or a blood clot, and periodic whole body scintigraphic images are obtained starting 10 min. post injection to determine the localization of the radiolabeled peptide to accumulations of platelets, including sites of thrombosis or blood clots. The effectiveness of the labeled peptide to image thrombosis is noted.

EXAMPLE 57—IMAGING OF TUMORS USING $^{99m}$Tc-D-Arg-Gly-D-Cys-β-Ala

The RGD analogue D-Arg-Gly-D-Cys-β-Ala of any of Examples 1–4 is radiolabeled by any of the methods of Example 5–10, or modifications thereof, with between 5 and 20 mCi of $^{99m}$Tc. The labeled RGD analogue is administered, by i.v. injection or regional delivery, to patients suspected of having metastatic or other tumors, and periodic whole body scintigraphic images are obtained starting 10 min. post injection to determine the localization of the radiolabeled peptide to the tumor site or sites. The effectiveness of the labeled peptide to image these tumors is noted.

EXAMPLE 58—DESIGN AND SYNTHESIS OF TETRADENDATE METAL ION RGD ANALOGUE

A peptide derivative D-Arg-Gly-His-β-Ala is synthesized according to the well established methods of peptide synthesis, such as the methods of Examples 1 to 3 or modifications thereof. The peptide derivative D-Arg-Gly-His-β-Ala is complexed with a tetradendate metal ions, such as Cu, Co, Zn, Ni, or Mn. Upon complexation to the metal ion, the peptide binds specifically to the heterodimeric receptor GP IIb/IIIa on activated platelets. This peptide-metal ion complex therefore is able to bind thrombus in vivo and may find use as an anti-thrombus agent and as an therapeutic agent for myocardial infraction. A complex of this peptide with Mn may also be utilized for locating deep vein thrombus or pulmonary emboli in mammals by magnetic resonance imaging techniques. The peptide molecules without the metal ion are either inactive or extremely weak ligands for the platelet receptor.

EXAMPLE 59—DESIGN AND SYNTHESIS OF TETRADENDATE METAL ION TUFTSIN ANALOGUE

A peptide derivative Thr-D-Lys-Gly-His-Arg is synthesized according to the well established methods of peptide synthesis, such as the methods of Examples 1 to 3 or modifications thereof. The peptide derivative Thr-D-Lys-Gly-His-Arg is complexed with a tetradendate metal ions, such as Cu, Co, Zn, Ni, or Mn. Upon complexation to the metal ion, the peptide binds specifically to the tuftsin receptor on polymorphonuclear leukocytes and macrophages and stimulates phagocytosis in these cells. This peptide-metal ion complex therefore may be utilized to enhance the biological actions that are mediated through PMN leukocytes and macrophages in fighting infection and antigen processing and presentation. A complex of this peptide with Mn may also be utilized for locating infection and inflammation foci in mammals by magnetic resonance imaging techniques. The peptide molecules without the metal ion are either inactive or extremely weak ligands for the tuftsin receptor.

All of the foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A manufactured peptide and pharmaceutically acceptable salts thereof with a conformationally constrained secondary structure upon complexing with a metal ion, the resulting conformationally constrained secondary structure comprising a member of a ligand and receptor pair, said peptide being of the general formula:

$$R_1-X-R_2$$

wherein X is a complexing backbone for complexing a metal ion comprising two or more amino acids, so that substantially all of said valences of the metal ion are satisfied upon complexation of the metal ion with X;

wherein X has, upon complexing with the metal ion, a specific regional secondary structure forming a part of the secondary structure;

wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure; and wherein the conformationally constrained secondary structure comprising X comprises, upon forming the conformationally constrained secondary structure, a ligand forming a member of a ligand and receptor pair.

2. The peptide of claim 1 wherein X comprises two or more contiguous amino acids containing at least one nitrogen, sulfur or oxygen atom available for complexing with the available valences of the metal ion.

3. The peptide of claim 1 wherein if less than all of the valences of the metal ion are satisfied upon complexation of the metal ion with the amino acids comprising X, then X also comprises a derivatized peptide or spacer sequence, which derivatized peptide or spacer sequence comprises at least one nitrogen, sulfur or oxygen atom available for complexing with the available valences of the metal ion, so that all of said valences of the metal ion are satisfied upon complexation of the metal ion with X.

4. The peptide of claim 1, wherein the affinity of the conformationally constrained secondary structure comprising a ligand for its receptor upon complexing with a metal ion is substantially higher than the affinity of the peptide which is not conformationally constrained in a secondary structure with a metal ion.

5. The peptide of claim 1, wherein at least a portion of the conformationally constrained secondary structure mimics a known biological-function domain.

6. The peptide of claim 1, wherein the peptide further comprises a metal ion complexed to X.

7. The peptide of claim 6, wherein the metal ion is an ionic form of the element selected from the group cosisting of iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium or astatine.

8. The peptide of claim 6, wherein the metal ion is a medically useful metal ion.

9. The peptide of claim 6, wherein the metal ion is radioactive or paramagnetic.

10. The peptide of claim 1, wherein X comprises at least one amino acid containing at least one nitrogen atom available for complexing with the available valences of the metal ion.

11. The peptide of claim 1, wherein X comprises at least one amino acid containing at least one sulfur atom available for complexing with the available valences of the metal ion.

12. The peptide of claim 1, wherein X comprises at least one amino acid containing at least one oxygen atom available for complexing with the available valences of the metal ion.

13. A method of making a peptide and pharmaceutically acceptable salts thereof with a conformationally constrained secondary structure obtained upon complexing with a metal ion, the method comprising the steps of:

a) providing a peptide of the general formula:

$R_1$—X—$R_2$ wherein X is a complexing backbone for complexing metal ion comprising two or more amino acids, so that substantially all of said valences of the metal ion are satisfied upon complexation of the metal ion with X, wherein X has, upon complexing with the metal ion, a specific regional secondary structure forming a part of the secondary structure, and wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure; and b) complexing a metal ion to the peptide.

14. The method of claim 13 wherein X comprises two or more contiguous amino acids containing at least one nitrogen, sulfur or oxygen atom available for complexing with the available valences of the metal ion.

15. The method of claim 13 wherein if less than all of the valances of the metal ion are satisfied upon complexation of the metal ion with the amino acids comprising X, then X also comprises a derivatized peptide or spacer sequence, which derivatized peptide or spacer sequence comprises at least one nitrogen, sulfur or oxygen atom available for complexing with the available valences of the metal ion, so that all of said valences of the metal ion are satisfied upon complexation of the metal ion with X.

16. A method of making a peptide or pharmaceutically acceptable salts thereof that comprises a conformationally constrained secondary structure comprising a ligand forming a member of a ligand and receptor pair, the method comprising the steps of:

a) providing a peptide of the general formula:

$R_1$—X—$R_2$ wherein X is a complexing backbone for complexing metal ion comprising two or more amino acids, so that substantially all of said valences of the metal ion are satisfied upon complexation of the metal ion with X, wherein X has, upon complexing with the metal ion, a specific regional secondary structure forming a part of the conformationally constrained secondary structure, wherein $R_1$ and $R_2$ each comprise from 0 to about 20 amino acids, said amino acids being selected so that upon complexing the metal ion with X at least a portion of either $R_1$ or $R_2$ or both have a structure forming the balance of the conformationally constrained secondary structure, and wherein the conformationally constrained secondary structure comprising at least a part of X, $R_1$ or $R_2$ comprises a ligand capable of forming a member of a ligand and receptor pair; and b) complexing a metal ion to the peptide;

whereby the metal ion causes X to form a specific regional secondary structure, thereby causing the peptide to be configured with a conformationally constrained secondary structure comprising a ligand forming a member of a ligand and receptor pair.

17. The method of claim 16, wherein the affinity of the peptide with a conformationally constrained secondary structure comprising a ligand for its receptor is substantially higher than the affinity of the peptide which is not conformationally constrained in a secondary structure with a metal ion.

18. A manufactured peptide and pharmaceutically acceptable salts thereof comprising a metal ion-binding backbone including two or more contiguous amino acids available for complexing with a metal ion and a determined biological-function domain, which biological-function domain is conformationally constrained and substantially biologically active only upon complexing the metal ion-binding backbone with a metal ion.

19. The peptide of claim 18, wherein at least a portion of the peptide is conformationally constrained in a secondary structure upon complexing the metal ion-binding backbone with the metal ion.

20. The peptide of claim 19, wherein the peptide has a conformationally constrained secondary structure upon complexing the metal ion-binding backbone with a metal ion.

21. The peptide of claim 18, wherein the metal ion-binding backbone comprises two or more amino acids each containing at least one nitrogen, sulfur or oxygen atom available for complexing with the available valences of the metal ion.

22. The peptide of claim 18 wherein if less than all of the valences of the metal ion are satisfied upon complexation of the metal ion with the amino acids comprising the metal ion-binding backbone, then the metal ion-binding backbone also comprises a derivatized peptide or spacer sequence, which derivatized peptide or spacer sequence comprises at least one nitrogen, sulfur or oxygen atom available for complexing with the available valences of the metal ion, so that all of said valences of the metal ion are satisfied upon complexation of the metal ion.

23. The peptide of claim 18, wherein the biological-function domain comprises a ligand forming a member of a ligand and receptor pair.

24. The peptide of claim 23, wherein the affinity of the biological-function domain comprising a ligand for its receptor is substantially higher when the metal ion-binding backbone is complexed with a metal ion than the affinity of the biological-function domain when the metal ion-binding backbone is not complexed with a metal ion.

25. The peptide of claim 18, wherein the metal ion-binding backbone is labeled with a metal ion.

26. The peptide of claim 25, wherein the metal ion is an ionic form of the element selected from the group consisting of iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium or astatine.

27. The peptide of claim 25, wherein the metal ion is a medically useful metal ion.

28. The peptide of claim 25, wherein the metal ion is radioactive or paramagnetic.

29. The peptide of claim 18 wherein upon labeling the metal ion-binding backbone with a metal ion the biological-function domain is sychnological.

30. The peptide of claim 18 wherein upon labeling the metal ion-binding backbone with a metal ion the biological-function domain is rhegnylogical.

31. The peptide of claim 18, wherein the determined biological-function domain, upon being conformationally constrained in a secondary structure by complexing the metal ion-binding backbone with a metal ion, is specific for the tuftsin receptor.

32. The peptide of claim 31 of the formula:

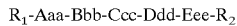

R₁-Aaa-Bbb-Ccc-Ddd-Eee-R₂ wherein

Aaa is a L- or D-isomer of Thr, Cys, Pen, or Ser and corresponding des-amino derivatives;

Bbb is an amino acid with a positively charged side chain and containing a N which is available for binding a metal ion;

Ccc is an amino acid with an un-charged side chain and containing a N which can be available for binding a metal ion;

Ddd is an amino acid containing a S or a S and a N which is available for binding a metal ion;

Eee is an amino acid with a positively charged side chain;

$R_1$ is H, alkyl, aryl, alkylcarbonyl, arylcarbonyl, alkyloxycarbonyl, aryloxycarbonyl, or a polymer attached directly or through a carbonyl group, unless Aaa is a des-amino amino acid, in which case $R_1$ does not exist; and $R_2$ is, an amide, substituted amide, ester, or a polymer unless Eee is a des-carboxyl amino acid, in which case $R_2$ does not exist.

33. The peptide of claim 32 which is Thr-D-Lys-Gly-D-Cys-Arg.

34. The peptide of claim 32 wherein the metal ion-binding backbone is complexed with a gamma emitting metal ion.

35. The peptide of claim 32 for diagnostic imaging of sites of infection or inflammation.

36. A peptide-based pharmaceutical composition suitable for administration to a patient comprising a peptide comprising a metal ion-binding backbone including two or more contiguous amino acids available for complexing with a metal ion and a determined biological-function domain, which biological-function domain is conformationally constrained and substantially biologically active only upon complexing the metal ion-binding backbone with a metal ion; and a metal ion complexing agent.

37. The peptide of claim 36, wherein at least a portion of the peptide is conformationally constrained in a secondary structure upon complexing the metal ion-binding backbone with a metal ion.

38. The peptide of claim 36, wherein the biological-function domain is substantially not biologically active until the metal ion-binding backbone is complexed with a metal ion.

39. The peptide of claim 36, wherein the metal ion-binding backbone comprises two or more amino acids each containing at least one nitrogen, sulfur or oxygen atom available for complexing with the available valences of the metal ion.

40. The peptide of claim 36 wherein if less than all of the valences of the metal ion are satisfied upon complexation of the metal ion with the amino acids comprising the metal ion-binding backbone, then the metal ion-binding backbone also comprises a derivatized peptide or spacer sequence, which derivatized peptide or spacer sequence comprises at least one nitrogen, sulfur or oxygen atom available for complexing with the available valences of the metal ion, so that all of said valences of the metal ion are satisfied upon complexation of the metal ion.

41. The peptide-based pharmaceutical composition of claim 36 wherein said metal ion complexing agent comprises a stannous ion agent.

42. The peptide-based pharmaceutical composition of claim 41 wherein said stannous ion agent is selected from the group consisting of stannous tartrate, stannous glucoheptonate, stannous gluconate, stannous phosphonate, stannous chloride, stannous sulfate, stannous acetate, or stannous fluoride.

43. The peptide-based pharmaceutical composition of claim 41 wherein said stannous ion agent is present in a solution comprising alkali metal tartrate.

44. The peptide-based pharmaceutical composition of claim 41 wherein the stannous ion agent is present in a solution comprising dicarboxylic acid.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
        ( D ) OTHER INFORMATION: Xaa is N- formyl-Met ( x i ) SEQUENCE DESCRIPTION: SEQ ID NO: 1:

Xaa  Leu  Phe
1

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 2:

Lys  Cys  Thr  Cys  Cys  Ala
1                   5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 3:

Tyr  Ile  Gly  Ser  Arg
1                   5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Peptide (iii) HYPOTHETICAL: No (iv) ANTI-SENSE: No (xi) SEQUENCE DESCRIPTION: SEQ ID NO: 4:

Gly Gly Gly Gly
1

(2) INFORMATION FOR SEQ ID NO:5:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: Peptide (iii) HYPOTHETICAL: No (iv) ANTI-SENSE: No (xi) SEQUENCE DESCRIPTION: SEQ ID NO: 5:

Thr Lys Pro Arg
1

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: Peptide (iii) HYPOTHETICAL: No (iv) ANTI-SENSE: No (xi) SEQUENCE DESCRIPTION: SEQ ID NO: 6:

Tyr Ile Gly Ser Cys Arg
1               5